(12) United States Patent
Edwards et al.

(10) Patent No.: US 8,214,566 B2
(45) Date of Patent: Jul. 3, 2012

(54) CONFIGURABLE HEALTH-CARE EQUIPMENT APPARATUS

(75) Inventors: Ian K. Edwards, Skaneateles, NY (US); Raymond A. Lia, Auburn, NY (US); Scott A. Martin, Warners, NY (US); Jon R. Salvati, Skaneateles, NY (US); Robert L. Vivenzio, Auburn, NY (US); Thaddeus J. Wawro, Auburn, NY (US); Robert J. Wood, Syracuse, NY (US)

(73) Assignee: Welch Allyn, Inc., Skaneateles, NY (US)

( * ) Notice: Subject to any disclaimer, the term of this patent is extended or adjusted under 35 U.S.C. 154(b) by 0 days.

(21) Appl. No.: 12/842,528

(22) Filed: Jul. 23, 2010

(65) Prior Publication Data
US 2011/0022748 A1 Jan. 27, 2011

Related U.S. Application Data

(60) Provisional application No. 61/228,249, filed on Jul. 24, 2009.

(51) Int. Cl.
*G06F 13/38* (2006.01)
*G06F 13/00* (2006.01)

(52) U.S. Cl. ............ 710/63; 710/62; 710/100; 709/208; 709/227

(58) Field of Classification Search .................... None
See application file for complete search history.

(56) References Cited

U.S. PATENT DOCUMENTS

| | | | |
|---|---|---|---|
| 4,284,849 A * | 8/1981 | Anderson et al. | 379/38 |
| 5,261,080 A | 11/1993 | Khoyi et al. | |
| 5,307,262 A | 4/1994 | Ertel | |
| 5,446,880 A | 8/1995 | Balgeman et al. | |
| 5,708,828 A | 1/1998 | Coleman | |
| 5,710,908 A | 1/1998 | Man | |
| 5,721,895 A | 2/1998 | Velissaropoulos et al. | |
| 5,734,907 A | 3/1998 | Jarossay et al. | |
| 5,857,195 A | 1/1999 | Hayashi et al. | |
| 5,892,925 A | 4/1999 | Aditya et al. | |
| 5,999,979 A | 12/1999 | Vellanki et al. | |
| 6,026,392 A | 2/2000 | Kouchi et al. | |
| 6,057,509 A * | 5/2000 | Simmons | 174/53 |

(Continued)

FOREIGN PATENT DOCUMENTS

EP 0707824 4/1996

(Continued)

OTHER PUBLICATIONS

International Search Report and Written Opinion for PCT/US2010/043104, dated Mar. 3, 2011 (8 pages).

(Continued)

*Primary Examiner* — Henry Tsai
*Assistant Examiner* — Michael Sun
(74) *Attorney, Agent, or Firm* — Hiscock & Barclay, LLP; R. S. Rosenholm

(57) ABSTRACT

An apparatus, system and method for providing health-care equipment in a plurality of customizable configurations. A configuration includes a selection and arrangement of health-care equipment modules that each provide specialized support for the provision of health care, including the measurement of physiological parameters. Various types of configurations include those adapted to be mounted upon a desk top or a wall surface, or adapted for wheel mounting or hand-carriable mobile configurations.

31 Claims, 53 Drawing Sheets

U.S. PATENT DOCUMENTS

| | | | | |
|---|---|---|---|---|
| 6,130,917 | A | 10/2000 | Monroe | |
| 6,190,313 | B1 | 2/2001 | Hinkle | |
| 6,249,668 | B1 | 6/2001 | Abe et al. | |
| 6,250,309 | B1 | 6/2001 | Krichen et al. | |
| 6,275,869 | B1 | 8/2001 | Sieffert et al. | |
| 6,400,286 | B1 | 6/2002 | Cooper | |
| 6,584,445 | B2 | 6/2003 | Papageorge | |
| 6,593,528 | B2* | 7/2003 | Franklin-Lees et al. | 174/58 |
| 6,625,617 | B2 | 9/2003 | Yarnall et al. | |
| 6,633,833 | B2 | 10/2003 | Sharma et al. | |
| 6,644,322 | B2 | 11/2003 | Webb | |
| 6,651,104 | B1 | 11/2003 | Moon | |
| 6,669,631 | B2 | 12/2003 | Norris et al. | |
| 6,697,103 | B1 | 2/2004 | Fernandez et al. | |
| 6,721,286 | B1 | 4/2004 | Williams et al. | |
| 6,766,361 | B1 | 7/2004 | Venigalla | |
| 6,792,431 | B2 | 9/2004 | Tamboli et al. | |
| 6,801,331 | B1 | 10/2004 | Motoyama | |
| 6,839,717 | B1 | 1/2005 | Motoyama et al. | |
| 6,848,108 | B1 | 1/2005 | Caron | |
| 6,861,824 | B1* | 3/2005 | Liu et al. | 320/164 |
| 6,915,312 | B2 | 7/2005 | Bodnar et al. | |
| 6,940,807 | B1 | 9/2005 | Rezvani et al. | |
| 6,942,616 | B2 | 9/2005 | Kerr, II | |
| 6,951,539 | B2 | 10/2005 | Bardy | |
| 6,978,422 | B1 | 12/2005 | Bushe et al. | |
| 6,993,536 | B2 | 1/2006 | Yamanaka | |
| 7,016,963 | B1 | 3/2006 | Judd et al. | |
| 7,038,588 | B2* | 5/2006 | Boone et al. | 340/573.1 |
| 7,054,924 | B1 | 5/2006 | Harvey et al. | |
| 7,124,299 | B2 | 10/2006 | Dick et al. | |
| 7,134,994 | B2 | 11/2006 | Alpert et al. | |
| 7,336,187 | B2 | 2/2008 | Hubbard et al. | |
| 7,360,154 | B2 | 4/2008 | Gale | |
| 7,408,932 | B2 | 8/2008 | Kounavis et al. | |
| 7,979,136 | B2* | 7/2011 | Young et al. | 607/60 |
| 2001/0023315 | A1 | 9/2001 | Flach et al. | |
| 2002/0010797 | A1 | 1/2002 | Moulton | |
| 2002/0037035 | A1 | 3/2002 | Singh | |
| 2002/0072933 | A1 | 6/2002 | Vonk et al. | |
| 2002/0099854 | A1 | 7/2002 | Jorgensen | |
| 2002/0143824 | A1 | 10/2002 | Lee et al. | |
| 2002/0184384 | A1 | 12/2002 | Simmon et al. | |
| 2003/0037043 | A1 | 2/2003 | Chang et al. | |
| 2003/0074248 | A1 | 4/2003 | Braud et al. | |
| 2003/0233250 | A1 | 12/2003 | Joffe et al. | |
| 2004/0044545 | A1 | 3/2004 | Wiesmann et al. | |
| 2004/0088374 | A1 | 5/2004 | Webb et al. | |
| 2004/0143677 | A1 | 7/2004 | Novak | |
| 2004/0153543 | A1* | 8/2004 | Thomas | 709/225 |
| 2004/0172442 | A1 | 9/2004 | Ripley | |
| 2004/0176983 | A1 | 9/2004 | Birkett et al. | |
| 2004/0215830 | A1 | 10/2004 | Shenfield | |
| 2005/0054921 | A1 | 3/2005 | Katsman et al. | |
| 2005/0071316 | A1 | 3/2005 | Caron | |
| 2005/0071324 | A1 | 3/2005 | Bitsch et al. | |
| 2005/0071486 | A1 | 3/2005 | Vu et al. | |
| 2005/0091358 | A1 | 4/2005 | Mehra et al. | |
| 2005/0154855 | A1 | 7/2005 | Harris et al. | |
| 2005/0165947 | A1 | 7/2005 | Auriemma et al. | |
| 2005/0198364 | A1 | 9/2005 | Val et al. | |
| 2005/0204022 | A1 | 9/2005 | Johnston et al. | |
| 2006/0017563 | A1 | 1/2006 | Rosenfeld et al. | |
| 2006/0031545 | A1* | 2/2006 | Manders et al. | 709/230 |
| 2006/0039105 | A1* | 2/2006 | Smith et al. | 361/681 |
| 2006/0069605 | A1 | 3/2006 | Hatoun | |
| 2006/0111936 | A1* | 5/2006 | Mahesh et al. | 705/2 |
| 2006/0129435 | A1 | 6/2006 | Smitherman et al. | |
| 2006/0168513 | A1 | 7/2006 | Coulson et al. | |
| 2006/0179571 | A1* | 8/2006 | Newkirk | 5/600 |
| 2006/0229557 | A1 | 10/2006 | Fathallah et al. | |
| 2007/0061393 | A1 | 3/2007 | Moore | |
| 2007/0156726 | A1 | 7/2007 | Levy | |
| 2007/0167694 | A1 | 7/2007 | Causevic et al. | |
| 2007/0276261 | A1 | 11/2007 | Banet et al. | |
| 2008/0052384 | A1 | 2/2008 | Marl et al. | |
| 2008/0055074 | A1 | 3/2008 | Gao et al. | |
| 2008/0082683 | A1 | 4/2008 | DelloStritto et al. | |
| 2008/0103375 | A1 | 5/2008 | Kiani | |
| 2008/0131761 | A1 | 6/2008 | Liu et al. | |
| 2008/0133699 | A1 | 6/2008 | Craw et al. | |
| 2008/0134133 | A1 | 6/2008 | DelloStritto et al. | |
| 2008/0140770 | A1* | 6/2008 | DelloStritto et al. | 709/203 |
| 2008/0249377 | A1 | 10/2008 | Molducci et al. | |
| 2008/0281168 | A1 | 11/2008 | Gibson et al. | |
| 2009/0005651 | A1* | 1/2009 | Ward et al. | 600/300 |
| 2009/0037514 | A1 | 2/2009 | Lankford et al. | |
| 2009/0093687 | A1* | 4/2009 | Telfort et al. | 600/300 |
| 2009/0143652 | A1 | 6/2009 | Warburton et al. | |
| 2009/0149927 | A1 | 6/2009 | Kneuer et al. | |
| 2009/0240116 | A1* | 9/2009 | Bluth | 600/300 |
| 2009/0267772 | A1* | 10/2009 | Dehnadi | 340/572.8 |
| 2009/0275810 | A1 | 11/2009 | Ayers et al. | |
| 2009/0306488 | A1* | 12/2009 | Al-Ali et al. | 600/324 |
| 2010/0005448 | A1 | 1/2010 | DelloStrito et al. | |
| 2010/0162017 | A1* | 6/2010 | Testin et al. | 713/320 |
| 2011/0069453 | A1* | 3/2011 | Campbell et al. | 361/700 |

FOREIGN PATENT DOCUMENTS

| | | |
|---|---|---|
| WO | WO 03/067842 | 8/2003 |
| WO | WO 2006/105139 | 10/2006 |

OTHER PUBLICATIONS

Colin Prodigy Press-Mate Prodigy II® Portable Vital Signs Monitors, DRE, Copyright 2009, accessed at: http://www.dremed.com/catalog/product_info.php/products_id/1181; 5 pages.

Fingertip Pulse Oximeter SPO2 Monitor Oxygen Oximeter; Copyright 1995-2010, accessed at: http://74.125.45.132/search?q=cache:ANfHne9je7gJ:cgi.ebay.com.sg/ws/eBayISAPI,dl1%3FViewItem%26item%3D260412542031+"Fingertip+Pulse+Oximeter+SPO2+Monitor+Oxygen+Oximeter"&cd=2&hl=en&ct=clnk&gl=us; 6 pages.

Handheld Pulse Oximeter PM-60A, Contec Medical System Co. Ltd., Jul. 31, 2009; accessed at: http://www.tradeindia.com/selloffer/1858593/Handheld-Puise-Oximeter-PM-60A.html; 5 pages.

International Search Report and Written Opinion for International Application No. PCT/US2006/011373, mailed Feb. 6, 2008 (12 pages).

Multiple Vital Signs from One Non-invasive Sensor, Starr™ Life Sciences Corp., Copyright 2009, accessed at: http://www.starrlifesciences.com/mouseox.html; 1 page.

NTIA Handheld Pulse Oximeter, Frontline Systems; Dec. 31, 2009, accessed at: http://www.tradeindia.com/fp385774/NTIA-Handheld-Pulse-Oximeter.html; 3 pages.

Portable Patient Monitors, Welch Allyn, Copyright 2005-2006 MedDirect, Copyright 2005-2006, accessed at: http://www.meddirect.co.nz/Product.aspx?ProductId=3476; 1 page.

U.S. Appl. No. 12/751,602, filed Mar. 31, 2010.

U.S. Appl. No. 29/353,090, filed Dec. 31, 2009.

\* cited by examiner

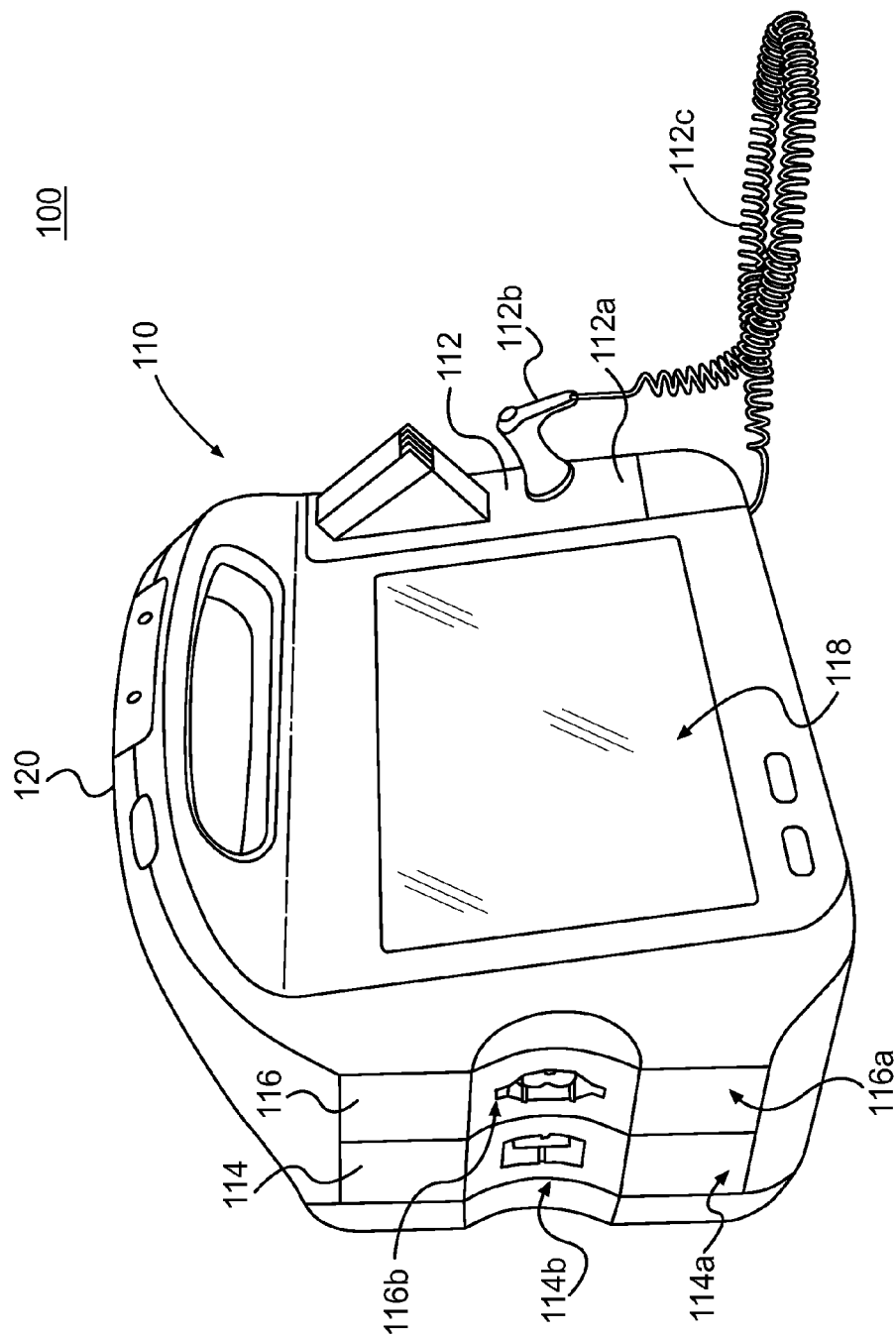

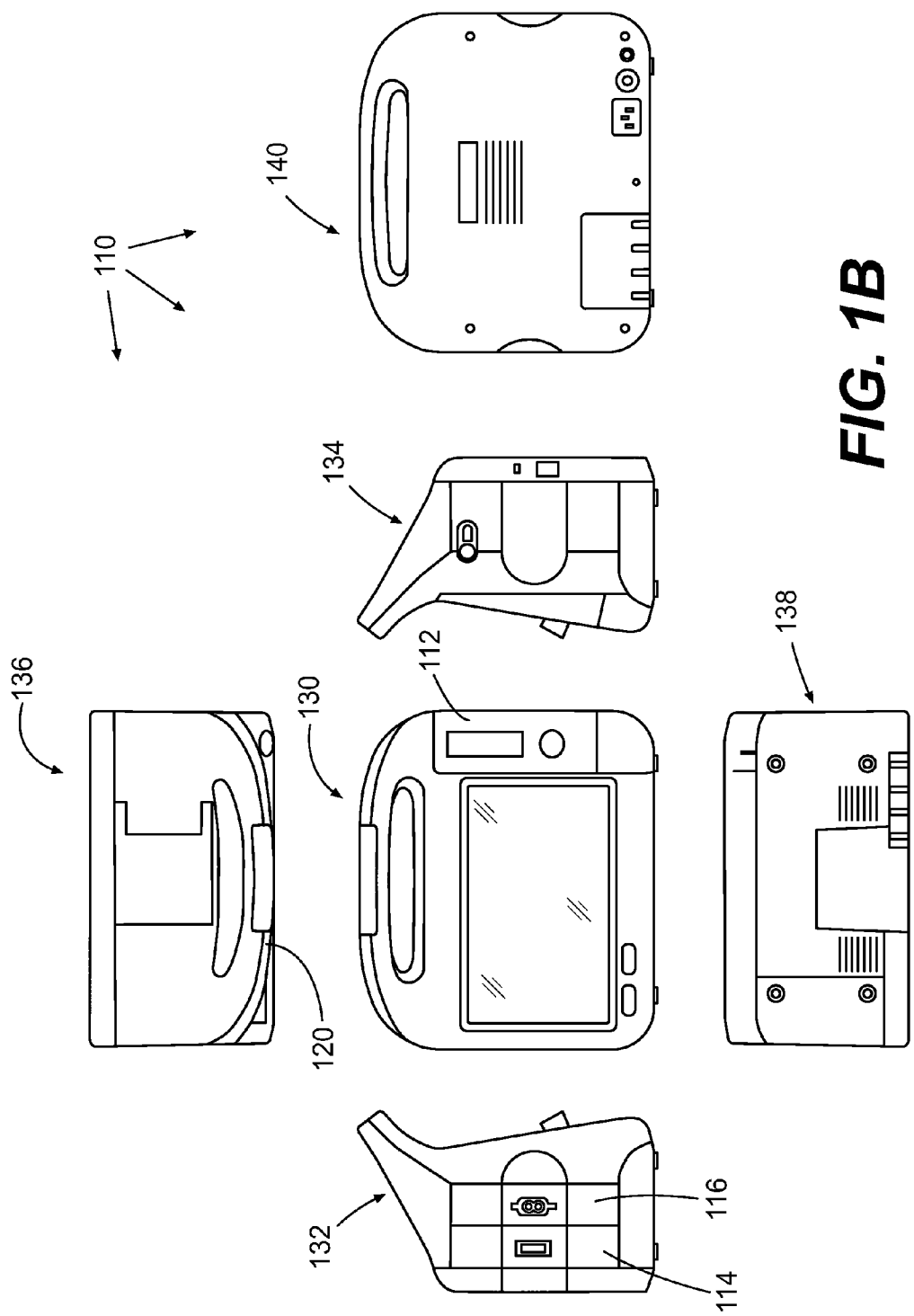

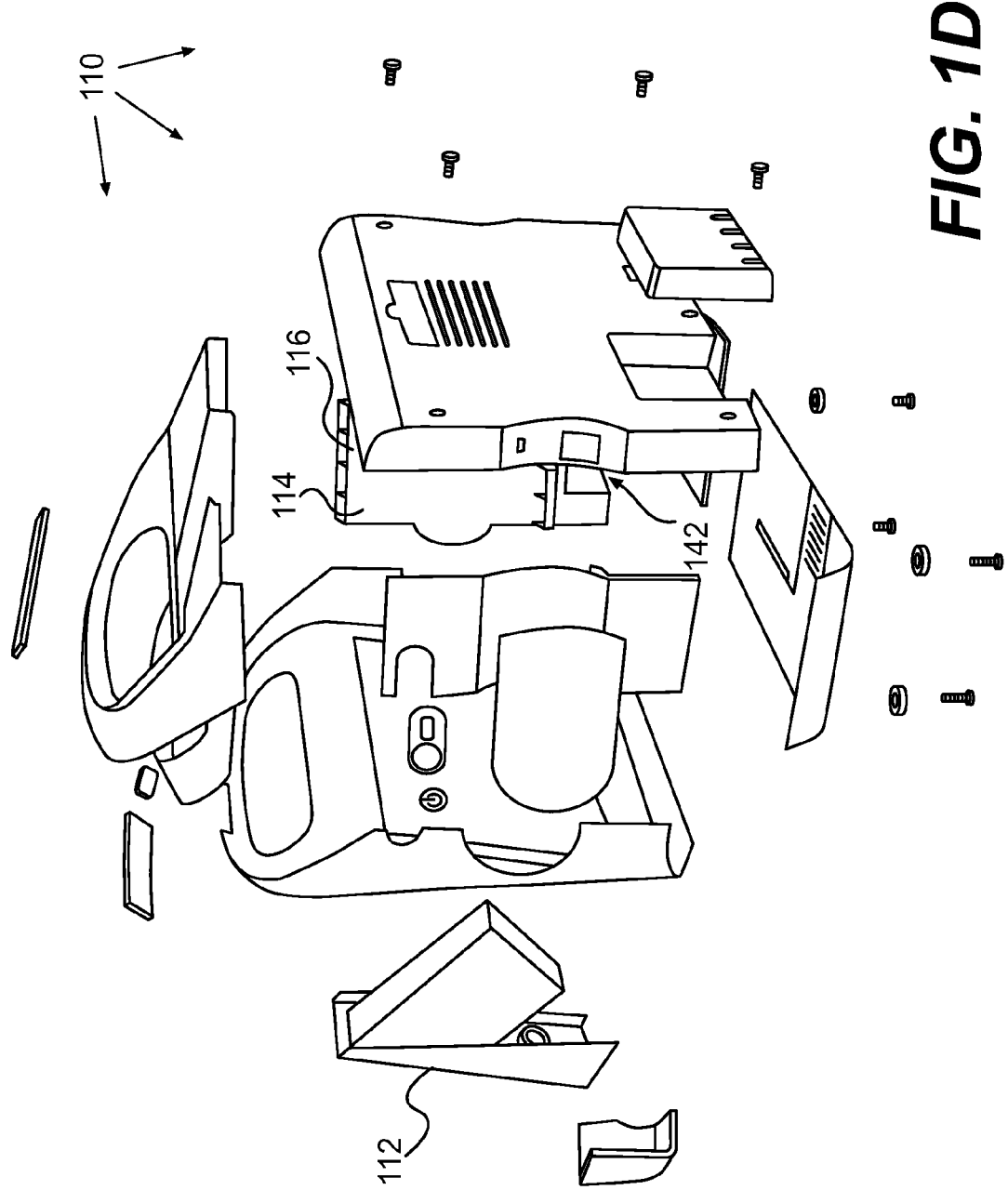

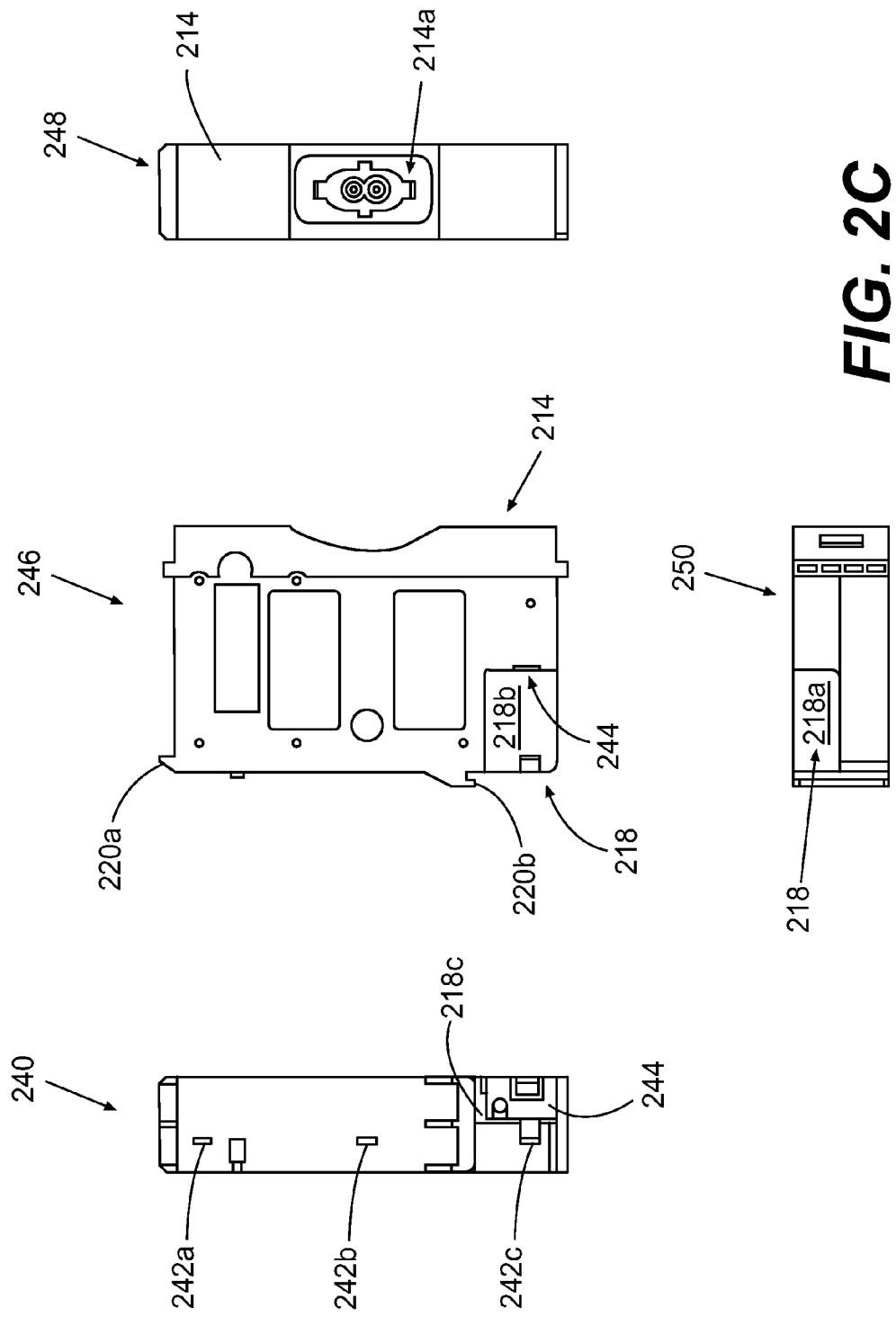

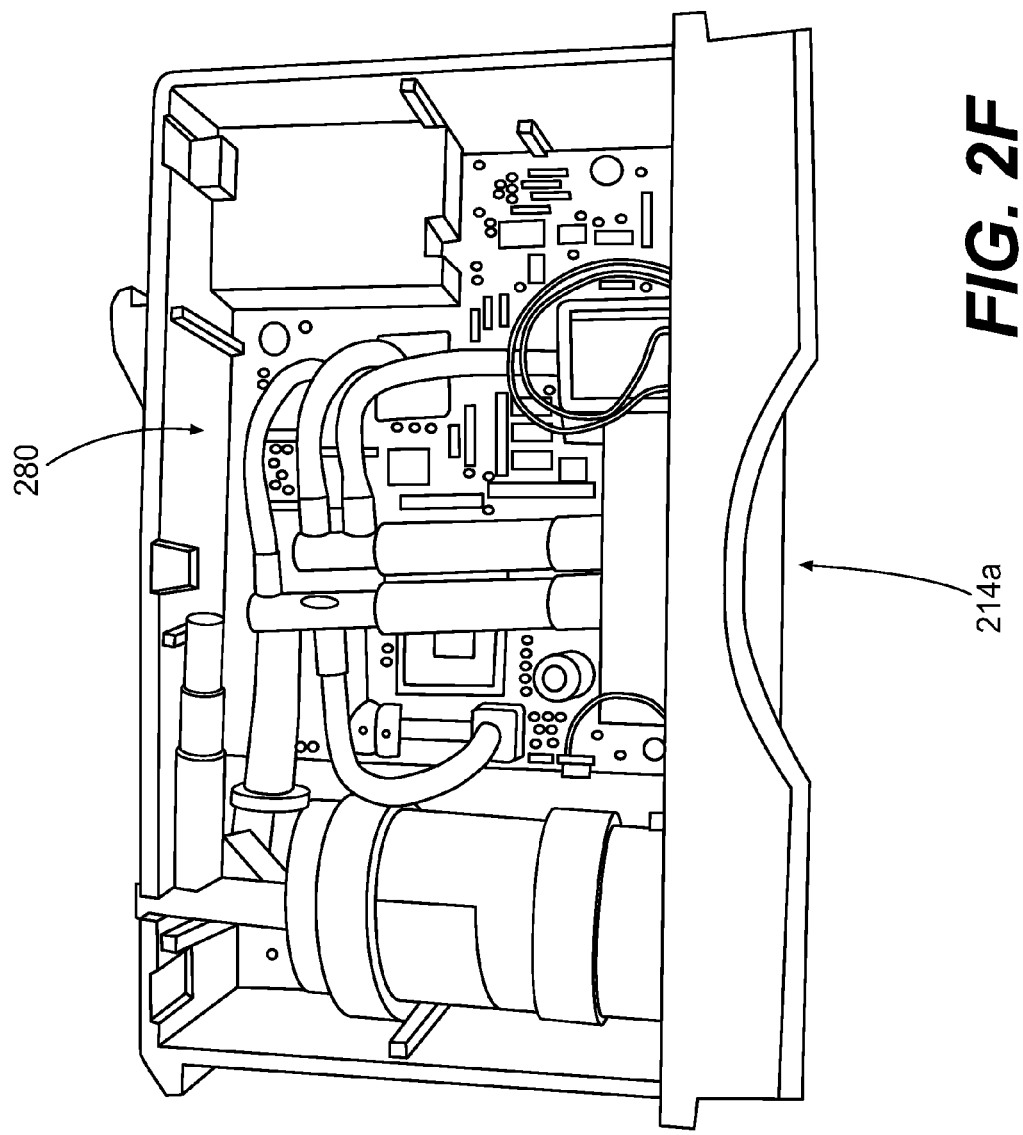

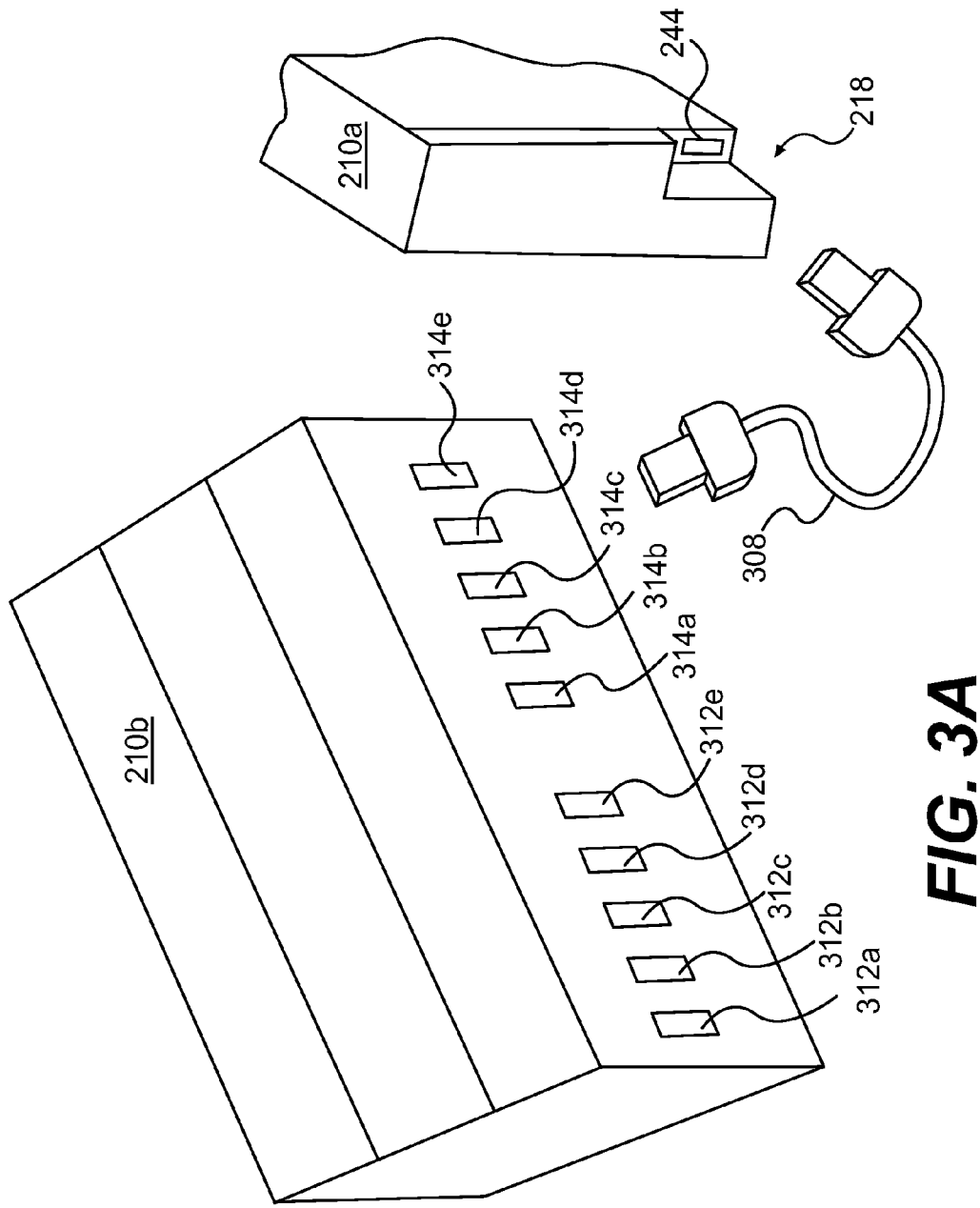

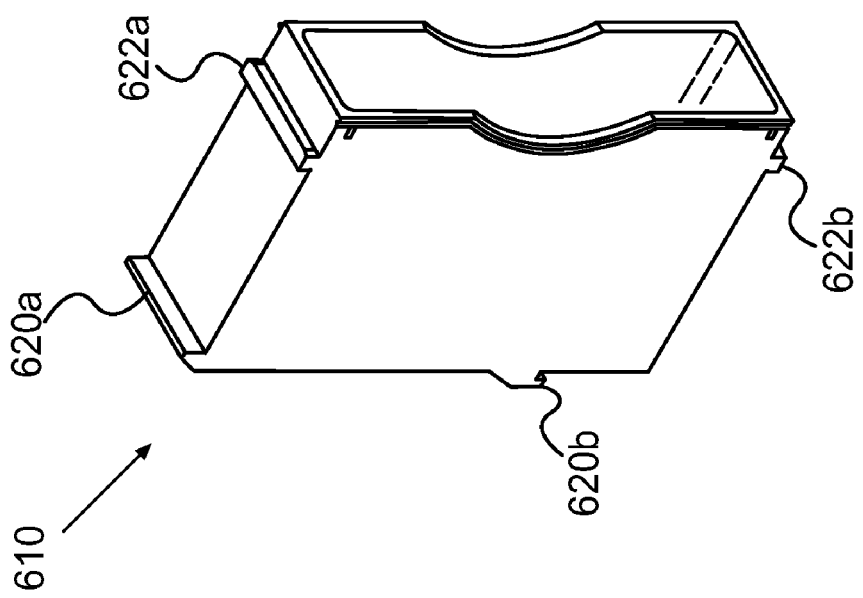

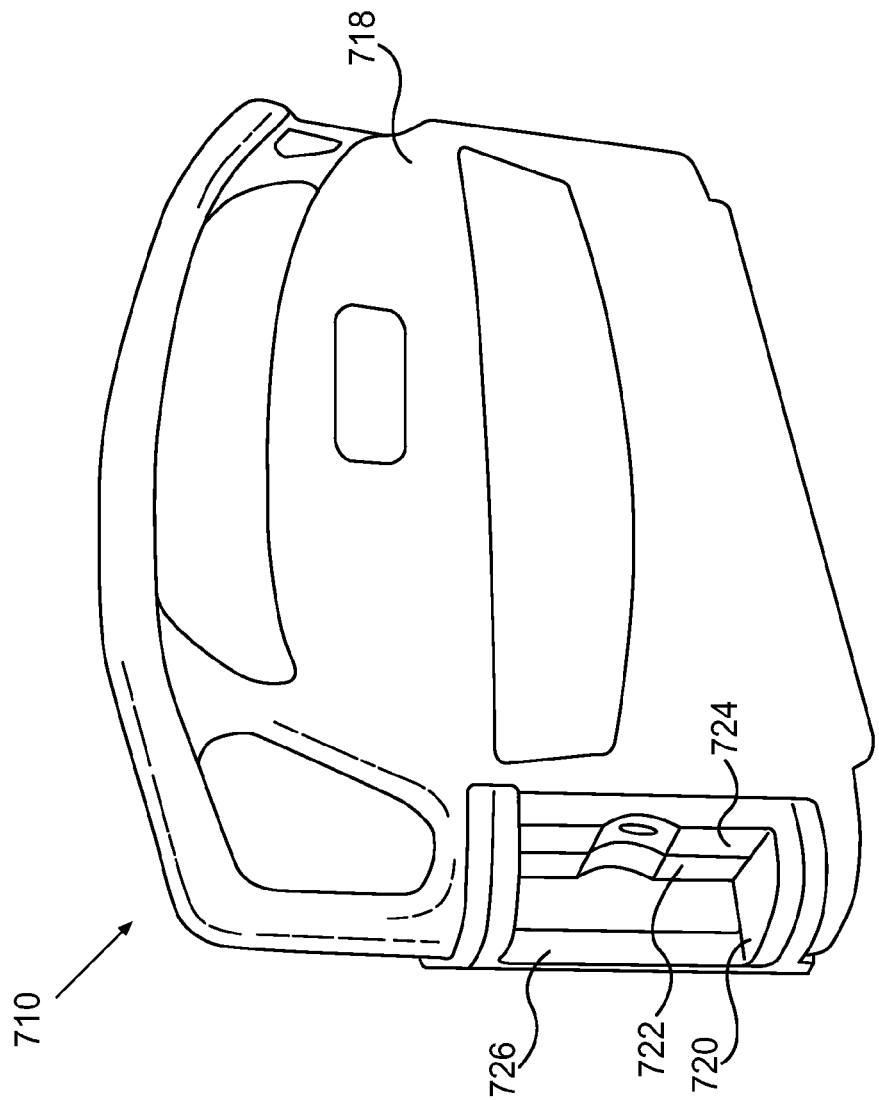

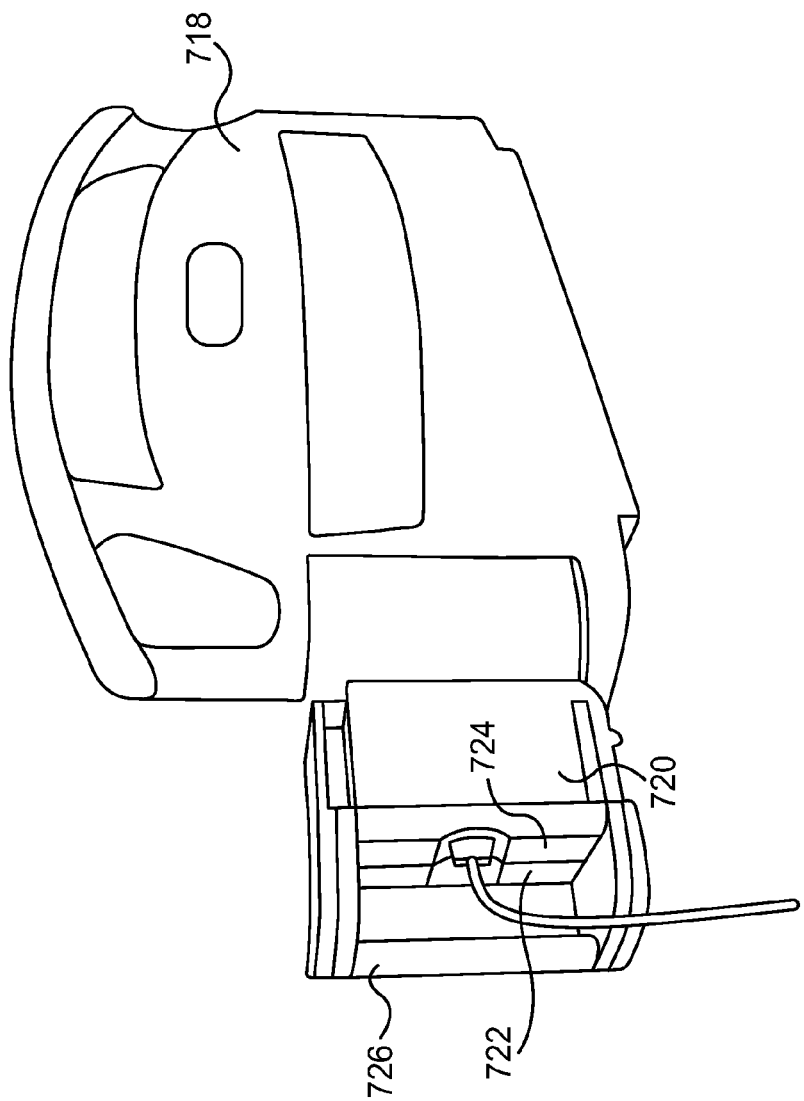

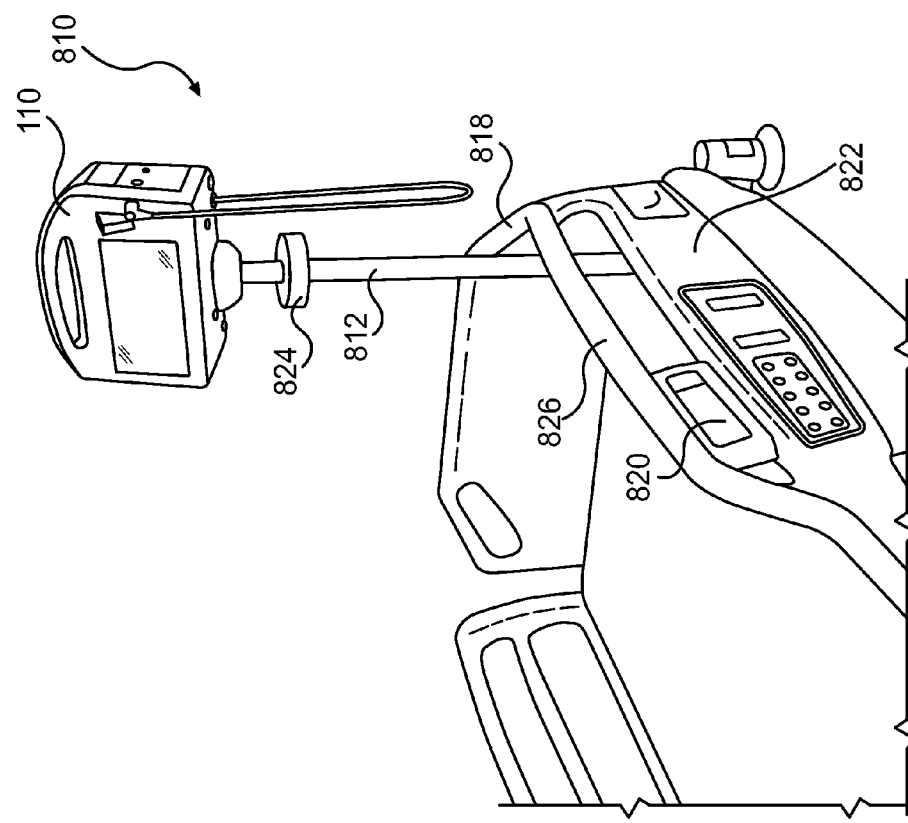

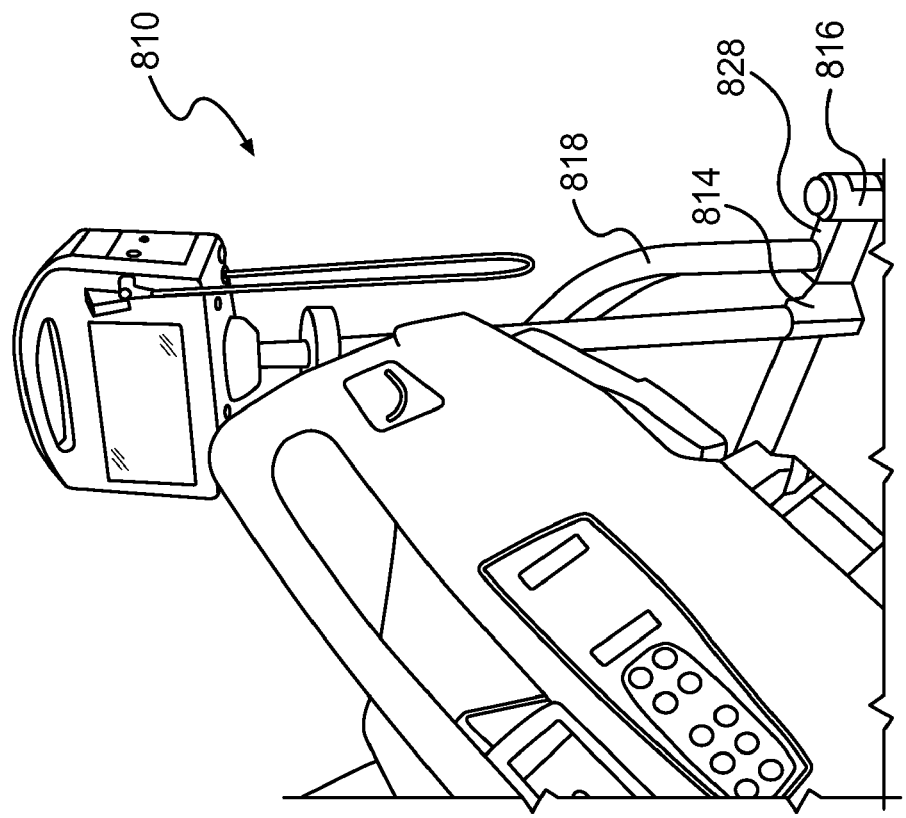

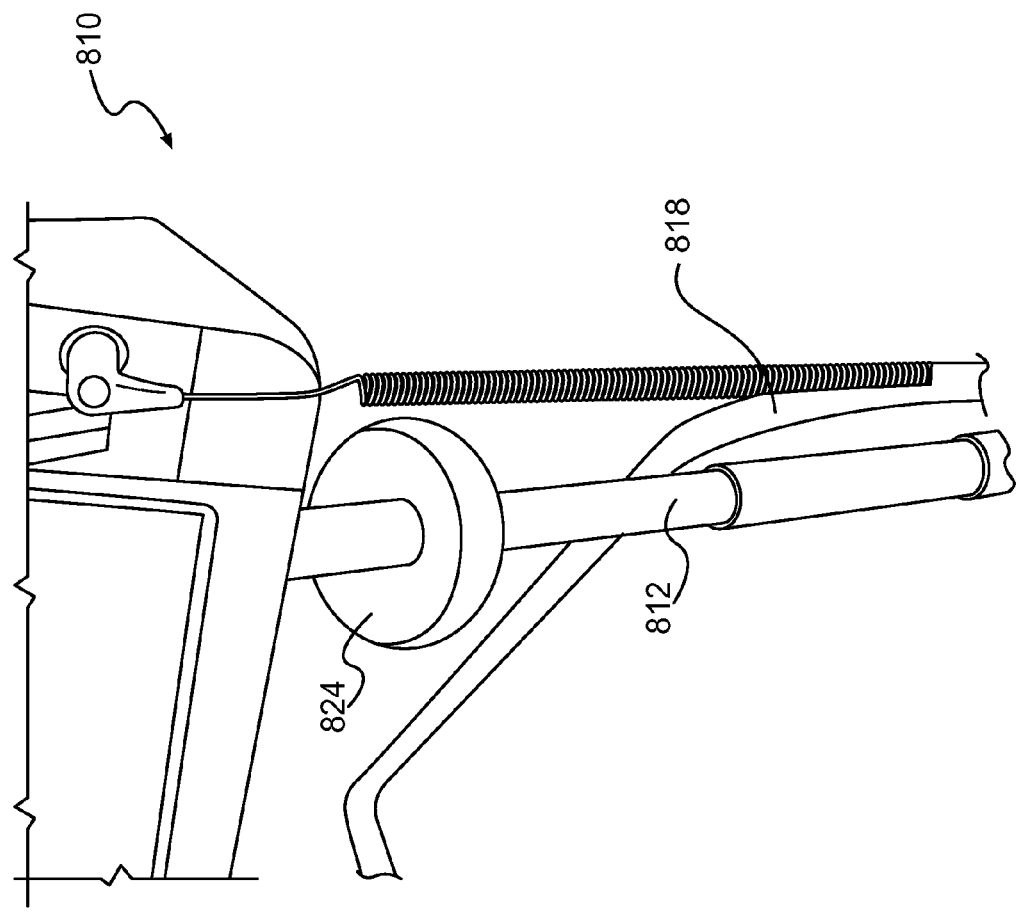

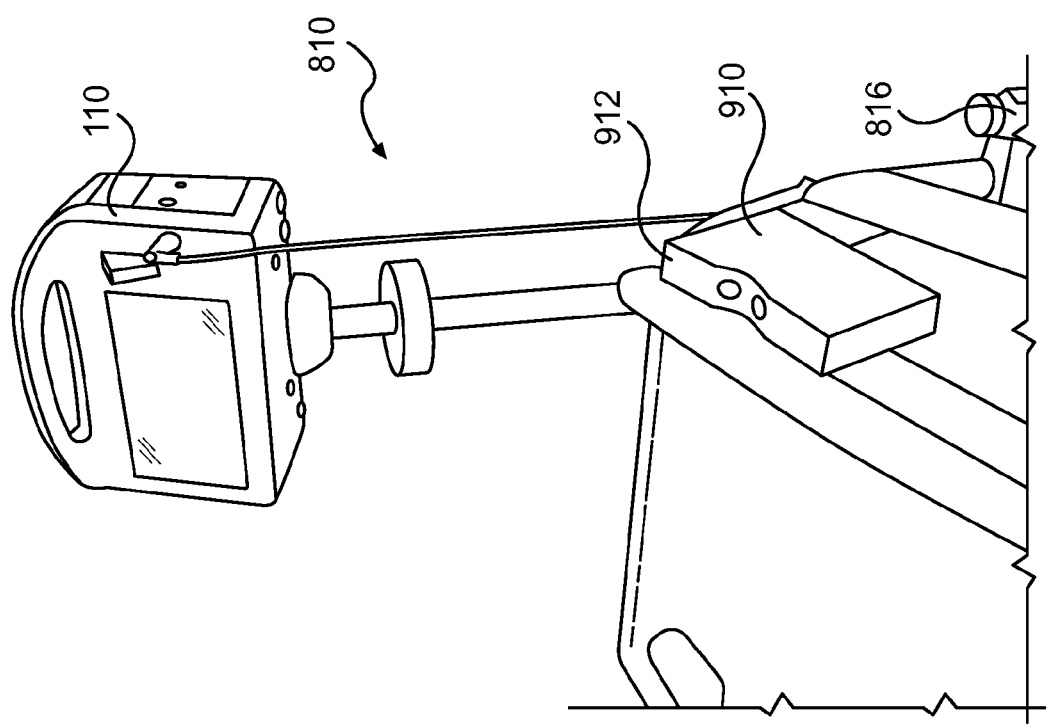

CONFIGURABLE HEALTH-CARE EQUIPMENT APPARATUS

CROSS-REFERENCE TO RELATED APPLICATIONS

This is a non-provisional patent application that claims priority and benefit to, U.S. provisional patent application Ser. No. 61/228,249 that was filed on Jul. 24, 2009 and entitled "Configurable Health-Care Equipment Apparatus", the aforementioned (61/228,249) patent application is incorporated herein by reference in its entirety.

CROSS-REFERENCE TO PATENT APPLICATIONS INCLUDING RELATED SUBJECT MATTER

This patent application includes subject matter related to U.S. non-provisional patent application Ser. No. 11/663,395 published as U.S. Publication No. 2010/0005448, to U.S. non-provisional patent application Ser. No. 11/905,811 published as U.S. Publication No. 2008/0082683, to U.S. non-provisional patent application Ser. No. 11/905,828 published as U.S. Publication No. 20080140770, to U.S. non-provisional patent application Ser. No. 11/905,829 published as U.S. Publication No. 20080133699, and to U.S. non-provisional patent application Ser. No. 11/905,830 published as U.S. Publication No. 20080134133. All of the aforementioned patent applications are incorporated herein by reference in their entirety.

FIELD OF THE INVENTION

This invention relates to an apparatus, system and method for providing health-care equipment in a plurality of customizable configurations. A configuration includes a selection and arrangement of health-care equipment modules that each provide specialized support for the provision of health care, including the measurement of physiological parameters. Various types of configurations include, but are not limited to, those adapted to be mounted upon a desk top, bed frame or a wall surface, or adapted for wheel mounting or hand carriable mobile configurations.

BACKGROUND OF THE INVENTION

Health care practitioners, such as nurses and physicians, use various types of health-care equipment to assist with the task of providing health care to a patient. A patient is also referred to herein as a health-care recipient. Some health-care equipment, referred to as single-function equipment, is designed to perform a particular function, such as to perform temperature measurement of a health-care recipient. Some health-care equipment, referred to as multi-function equipment, is designed to implement the performance of more than one function, such as the performance of temperature measurement and blood pressure measurement of a health-care recipient. Such multi-function equipment may impose excess bulk and/or weight upon a user if such multi-function equipment is used for only one function or a subset of the functions implemented by the multi-function equipment.

SUMMARY OF THE INVENTION

The invention provides an apparatus, system and method for providing health-care equipment in a plurality of customizable configurations. A configuration includes a selection and arrangement of health-care equipment modules that each provide specialized support for the provision of health care, including the measurement of physiological parameters. Various types of configurations include those adapted to be mounted upon a desk top, a bed frame or a wall surface, or adapted for wheel mounting and/or adapted to be hand carriable as a mobile configuration.

In one aspect, the invention provides a frame for integrating a plurality of health-care equipment modules. The frame includes a supporting structure providing a mechanical interface for supporting each of a plurality of modules at one time, each of the plurality of modules including an embedded component, and an electrical interface providing a data transfer mechanism between a computing component and the embedded component, and where the computing component is configured for providing a software interface enabling a software connection between the computing component and the embedded component, the software interface configured to establish interoperation between the computing component and the embedded component, and where at least one of electrical power and data is configured to be transferred between the computing component and the embedded component via at least one of the electrical interface and the software interface.

In some embodiments, the data transfer mechanism includes a universal serial bus (USB), a universal serial bus (USB) host and a universal serial bus (USB) hub, and a universal serial bus (USB) module end-point connection. Optionally, the universal serial bus (USB) module end-point connection is designed for connection to the embedded component. One implementation is where a universal serial bus (USB) cable provides the universal serial bus (USB) module end point connection. The universal serial bus (USB) cable having a first end electrically attached to the universal serial bus (USB) host via the universal serial bus (USB) hub and a second end electrically attached to the universal serial bus (USB) module end-point connection.

Regardless of the design of the data transfer mechanism, in some embodiments, at least one module is configured to input information from a sensory device. Optionally, the sensory device is configured for measurement of a physiological parameter and/or the sensory device is a hand-held device. Also, in some embodiments, the hand-held device is a medical diagnostic instrument.

In some embodiments, the universal serial bus (USB) module end-point connection supplies voltage within universal serial bus (USB) standards while supplying current substantially in excess of universal serial bus (USB) standards. Optionally, the computing component is electrically attached to a non-module universal serial bus (USB) hub connection accessible from an exterior of the frame and from an exterior of a module mechanically attached to the frame via the supporting structure.

Optionally, within the aforementioned type of embodiment, the non-module universal serial bus (USB) hub connection supplies voltage and current within universal serial bus (USB) standards and wherein the universal serial bus (USB) module end-point connection supplies voltage within universal serial bus (USB) standards while simultaneously supplying current substantially in excess of universal serial bus (USB) standards.

Optionally, the aforementioned type of embodiment, the computing component transmits a command at least through one of a non-module universal serial bus (USB) host to an external component or the universal serial bus (USB) to the embedded component, to transition to a sleep mode. Optionally, the universal serial bus (USB) module end-point connection supplies voltage at about 4.75 volts to about 5.25 volts and supplies current at about 0.1 amperes to about 1.5 amperes. Optionally, the computing component and the universal serial bus (USB) end-point module connection is isolated via a five-volt to five-volt isolation transformer. Optionally, enclosure includes an external recessed portion being sized to provide an available volume within which the universal serial bus (USB) cable can pass through while attached to the universal serial bus (USB) connector. In some embodiments, the electrical interface is provided as a standard feature of a commercially available computer, whereby the computer can function as the computing component.

Regardless of the amount of current supplied, the software interface executes a protocol communicating at least one of a vendor-identification value and product-identification value from the embedded component to the computing component via the universal serial bus (USB) module end point connection, and interoperation can be permitted or denied based upon said at least one of said vendor identification value and said product identification value. Optionally, the software interface executes a WACP communication protocol that includes communication of a global unique identifier from the module embedded component to the power and computing component via the power and data connection, and wherein interoperation is permitted or denied based upon a value of the global unique identifier.

In some embodiments, the frame is further configured to be one of a desktop configuration, a wall configuration, a mobile configuration, a hand-carriable configuration, or a bed configuration. Each of the desktop configuration, the wall configuration, the mobile configuration, the hand-carriable configuration, and the bed configuration interoperate with equipment modules without modification to the mechanical interface, the electrical interface, or the software interface of the module. The module is configured to be attached and detached from any one of the desktop configuration, the wall configuration, the mobile configuration, the hand-carriable configuration, and the bed configuration. The frame as a supporting structure has means for enabling mechanical attachment to each of a plurality of health-care equipment modules at one time.

Optionally, the enclosure includes a detachable panel, the removal of the panel creating an opening within the enclosure, the opening providing access to enable at least one module embedded component to be transferred into and out of said cavity. The enclosure can include a front panel having a first configuration, the front panel being one of a plurality of differently configured front panels that each have a configuration that may be unique and different from the first configuration. The front panel can provide a user interface between said module and a user of the module. Each of a plurality of differently configured front panels can be further configured for attachment, detachment, and re-attachment to an enclosure.

In another aspect, the invention includes an enclosure for the module, the enclosure having a discrete width corresponding to an integer number of multiple units of width, the discrete width corresponding to a width of the module. Optionally, the module is designed as a docking station for a hand-held device.

As a docking station, it is designed for at least one of an otoscope, an ophthalmoscope, a rhinoscope, a laryngoscope, an anoscope, an audiometer, a tympanometric instrument, a thermometer, and a vaginoscope. Optionally, the module is at least one of a blood pressure measuring module and a pulse oximetry measurement module. Optionally, the module performs printing of information that is collected and/or stored within another module. Also, a module can be designed as a dispenser, a storage unit, or a cup holder.

In another aspect, the invention provides an enclosure including an interior cavity, an embedded component disposed therein, and a mechanical interface enabling attachment relative to a supporting structure, and where the interior cavity is dimensioned to surround the embedded component, and where the embedded component is configured for electrical interoperation with a computing component located external to the enclosure, and where the enclosure includes a data connection providing an electrical interface enabling an electrical attachment between the computing component and the embedded component, and where the embedded component being configured for software interoperation with the computing component, and where the embedded component includes software providing a software interface enabling a software connection between the computing component and the embedded component; and where at least one of electrical power and data configured to be transferred between the computing component and the embedded component via at least one of the electrical interface and the software interface.

In another aspect, the invention provides a method for providing health-care equipment in a plurality of customizable configurations. The method includes steps of providing at least one enclosure including an embedded component configured for measurement of a physiological parameter, the enclosure including a mechanical interface and including an electrical interface, providing a supporting structure frame for providing physical support for the at least one enclosure via the mechanical interface, providing a computing component configured for providing a software interface enabling a software connection between the computing component and the embedded component, the software interface configured to establish interoperation between the computing component and the embedded component via the electrical interface, and where at least one of electrical power and data is configured to be transferred between the computing component and the embedded component via at least one of the electrical interface and the software interface, and where the supporting structure is configured to be incorporated into a desktop configuration, a wall configuration, a mobile configuration, a hand-carriable configuration, or a bed configuration.

In some embodiments of this method, the electrical interface is provided as a standard electrical interface feature of a commercially available computer and the computer functions as the computing component. Optionally, the software interface establishes interoperation upon successful execution of a protocol communicating at least one of a vendor-identification value and product-identification value from the embedded component to the computing component. Optionally, at least one of said universal serial bus (USB) module end point connections is implemented as a standard universal serial bus (USB) connector that is configured to transfer current that may be substantially in excess of universal serial bus (USB) standards, and wherein said connector is accessible and attachable to a standard universal serial bus (USB) cable from outside of said enclosure, but not necessarily from outside of a module assembly.

In another aspect of the invention, a system for providing health-care equipment in a plurality of customizable configurations. The system includes at least one enclosure including an embedded component configured for measurement of a physiological parameter, the enclosure including a mechanical interface and including an electrical interface, a supporting structure providing physical support for the at least one enclosure via the mechanical interface, a computing component configured for providing a software interface enabling a software connection between the computing component and the embedded component, the software interface configured to establish interoperation between the computing component and the embedded component via the electrical interface, and where at least one of electrical power and data is configured to be transferred between the computing component and the embedded component via at least one of the electrical interface and the software interface; and where the supporting structure is configured to be incorporated into a desktop configuration, a wall configuration, a mobile configuration, a hand-carriable configuration, or a bed configuration.

BRIEF DESCRIPTION OF THE DRAWINGS

The objects and features of the invention can be better understood with reference to the claims and drawings described below. The drawings are not necessarily to scale, and the emphasis is instead being generally placed upon illustrating the principles of the invention. Within the drawings, like reference numbers are used to indicate like parts throughout the various views. Differences between like parts may cause those like parts to be each indicated by different reference numbers. Unlike parts are indicated by different reference numbers.

FIGS. 1A-1F illustrate a plurality of views of an assembled mobile frame apparatus configuration including three health-care equipment modules.

FIGS. 2A-2F illustrate various views of a module structure.

FIGS. 3A-3E each illustrate an aspect of an embodiment of a power and computing component (PACC).

FIGS. 6A-6H each illustrate embodiments of a socket module structure shown in various states of assembly.

FIGS. 7A-7F illustrate views of an integrated bed mounted module apparatus configuration 710.

FIGS. 8A-8E illustrate views of a pole mounted and bed frame attached module apparatus configuration.

FIGS. 9A-9E illustrate views of a side rail attached module apparatus.

DETAILED DESCRIPTION OF THE INVENTION

Figure 1C:
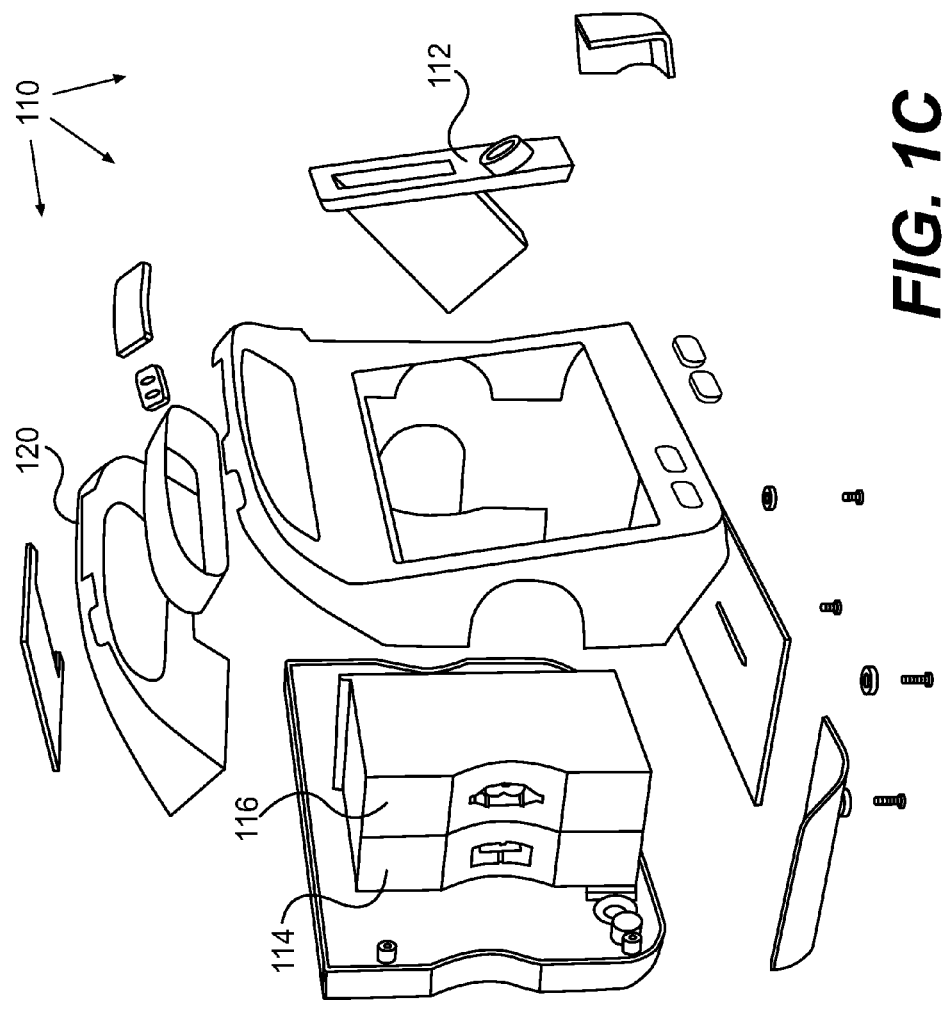

FIGS. 1A-1F illustrate views of an integrated mobile frame (MF) apparatus configuration including three (3) health-care equipment (HCE) modules. Health-care equipment modules, also referred to herein as HCE modules or modules, are designed to integrate into and operate within other and different types of apparatus configurations in addition to that of the MF apparatus configuration shown here.

The three HCE modules, shown in various viewing perspectives in FIGS. 1A-1D, are configured (designed) to be detached and removed from one type of apparatus configuration, such as from the integrated MF apparatus configuration (FIG. 1A), and attached to and integrated within another and different type of apparatus configuration, such as integrated within a desk top mounted type of apparatus configuration (FIG. 4A), or integrated within a wall mounted type of apparatus configuration (FIG. 5A), for example.

The three HCE modules referred to above, are also characterized as being cross configuration interoperable (CCI), because these modules are designed to be operable within more than one type of apparatus configuration. The HCE modules having CCI characteristics are also referred to herein as CCI types of HCE modules, or simply CCI modules. An HCE module not designed to be interoperable within more than one type of apparatus configuration, is characterized as being a non-CCI type of HCE module. All HCE modules referred to herein will refer to a CCI type of HCE module, unless explicitly stated otherwise.

FIG. 1A illustrates a front perspective view 100 of a mobile frame (MF) apparatus configuration 110 optionally including three CCI health-care equipment (HCE) modules 112-116. A temperature measurement module 112 is accessible from the front side, and a pulse oximetry (SPO2) measurement module 114 and a non-invasive blood pressure module (NIBP) 116 are accessible from a left hand side of the MF apparatus configuration 110. An upper handle portion 120 is also visible from this viewing perspective 100. The handle portion 120 enables the MF 100 to be hand carriable with relative ease.

A front side of the MF apparatus 110 includes a user interface display 118 and an outer surface of a temperature measurement module 112, also referred to as "SureTemp" module 112. The Sure Temp module 112, is also commercially known as the Welch Allyn Sure Temp Thermometer. A "module" refers to a combination of a module structure and optionally one or more peripheral and/or embedded components associated with the module structure. A module structure is also referred to herein as a module enclosure. The outer surface, seen as a front panel 112a of a temperature measurement module 112 (shown in FIG. 1A) is actually the outer surface of a module structure, like the outer surface of another module structure 210 shown in FIG. 2A.

Figure 2A:
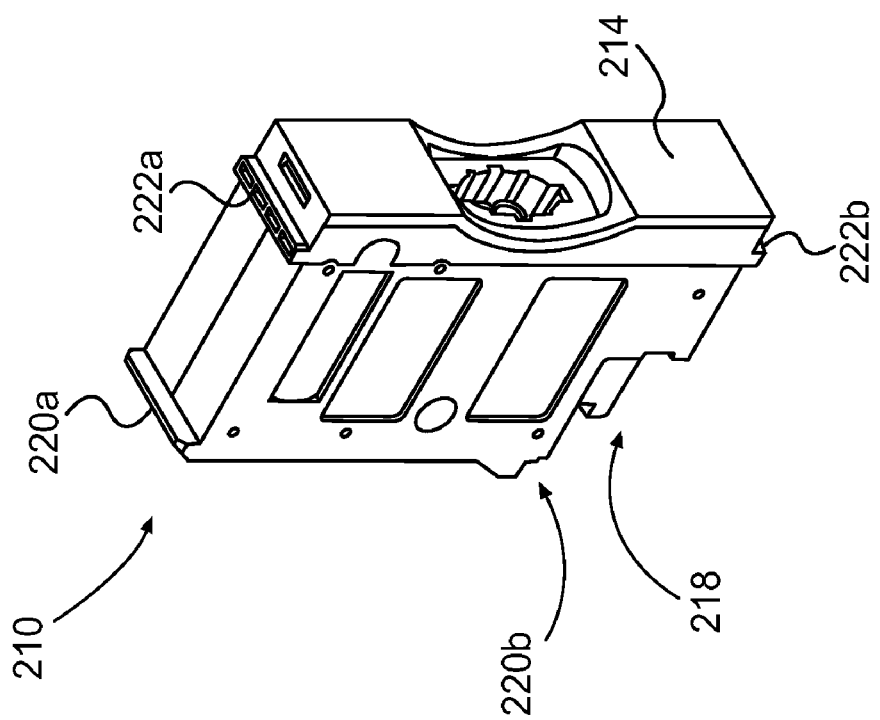

The module 210 of FIG. 2A includes a different front panel than that of module 112 and accordingly module 210 performs different functionality (blood pressure measurement) than functionality performed by module 112 (temperature measurement). The temperature measurement module 112 is designed to measure body temperature of a health-care recipient.

The temperature measurement module 112 includes a module structure including a front panel 112a, also referred to herein as a face plate 112a. The front panel 112a having an outer surface accessible from the front side of the MF apparatus configuration 110. The front panel 112a includes access to a well (not shown) storing a removable probe (not shown) attached to a probe handle 112b (shown). The probe and its attached probe handle 112b are tethered to the module 112 via an insulated conductor 112c. The probe is designed to make physical contact with a patient in order to sense a body temperature of the patient.

A left hand side of the MF apparatus configuration 110 includes an outer surface of each of the HCE modules 114-116. An SPO2 type of HCE module 114 is designed to measure oxygen content, within the blood of a patient. A non-invasive blood pressure (NIBP) type of HCE module 116 is designed to measure blood pressure of a patient.

As shown, the SPO2 module 114 includes a module structure including a front panel 114a, also referred to herein as a face plate 114a. The front panel 114a includes an outer surface accessible from the left side of the MF apparatus configuration 110. The front panel 114a includes a connector 114b that enables a connection between other peripheral SPO2 component(s) (not shown) and the SPO2 module 114 residing within the MF apparatus 110. The other peripheral SPO2 component(s) reside external to the MF apparatus 110 and the SPO2 module enclosure 114 and are configured to interoperate with the SPO2 module 114 when connected to the SPO2 module via connector 114b.

As shown, the NIBP module 116 includes a front panel (face plate) 116a having an outer surface accessible from the left side of the MF apparatus configuration 110. The front panel 116a includes a connector 116b that enables a connection between other peripheral NIBP component(s) (not shown) and the NIBP module itself 116 residing within the MF apparatus 110. Other peripheral NIBP component(s) that reside external to the MF 110 and the NIBP module 116 and are configured to interoperate with the NIBP module 116 when connected to the NIBP module via connector 116b.

FIG. 1B illustrates a variety of exterior views of a mobile frame (MF) apparatus configuration 110. View 130 illustrates the front side of the MF 110 as shown without a probe and handle inserted within the temperature measuring module. View 132 illustrates the left side of the MF 110 that includes access to the front panel of each of the HCE module 114 and the HCE module 116. View 134 illustrates a right side of the MF 110 while view 136 illustrates an upper side of the MF 110 including a handle portion 120. View 138 illustrates a bottom side of the MF 110 and view 140 illustrates a rear side of the MF 110.

FIG. 1C illustrates a left side perspective and exploded view of the MF 110. As shown, the SPO2 module 114 and the NIBP module 116 as they are oriented and integrated within the MF 110. The embedded surface of the temperature measurement module 112 is also shown.

During operation, both modules 114 and 116 are electrically connected to a power and computing component (PACC) (not shown here) located inside of the MF 110. In some embodiments, the PACC is connected to each module 114 and 116 via a power and/or data cable, such as a universal serial bus (USB) cable (not shown here). An embodiment of the PACC and a power and/or data cable is shown in FIGS. 2E and 3A.

FIG. 1D illustrates an exploded view of the MF 110 from a right side perspective. A partial rear perspective view of the SPO2 module structure 114 and of the NIBP module structure 116 as they are oriented and integrated within the MF 110 are shown. Also shown is a partial rear perspective view of a recessed portion 142 of the module enclosure 114 (also seen as 218 of FIG. 2A) and a rear perspective view of the temperature measurement module 112. The recessed portion 142 provides a volume of space within which a USB cable can occupy and pass through while the USB cable is attached to a USB connector (not shown) attached to an inner surface within the recessed portion 142 of the module structure 114.

Figure 1E:
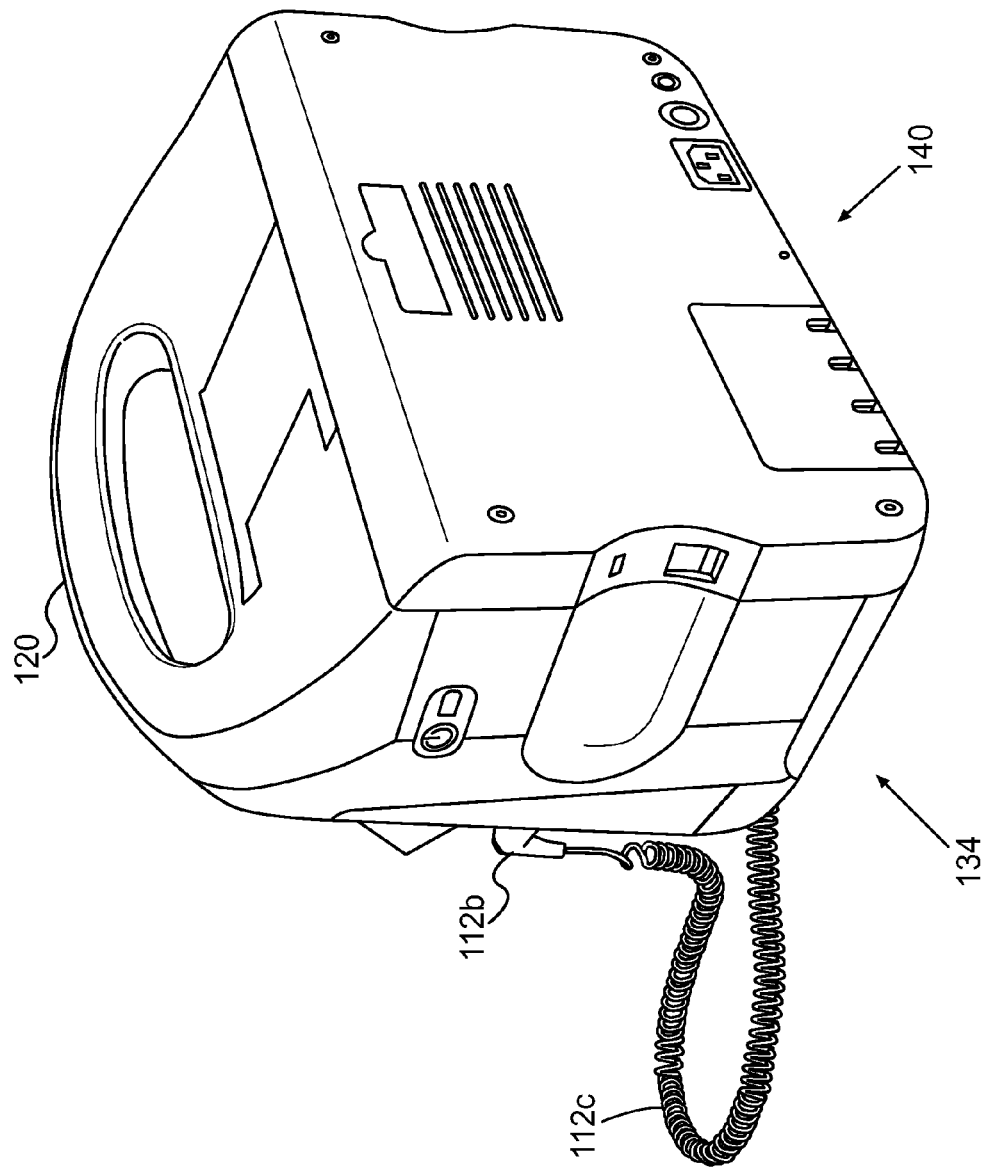

FIG. 1E illustrates a rear perspective view of the MF 110. Within this view, the rear-side view 140 and the right hand side 134 view of the MF are visible. A rear perspective view of the probe handle 112b and the insulated conductor 112c are visible. Also visible is the handle portion 120 of the MF 110.

Figure 1F:
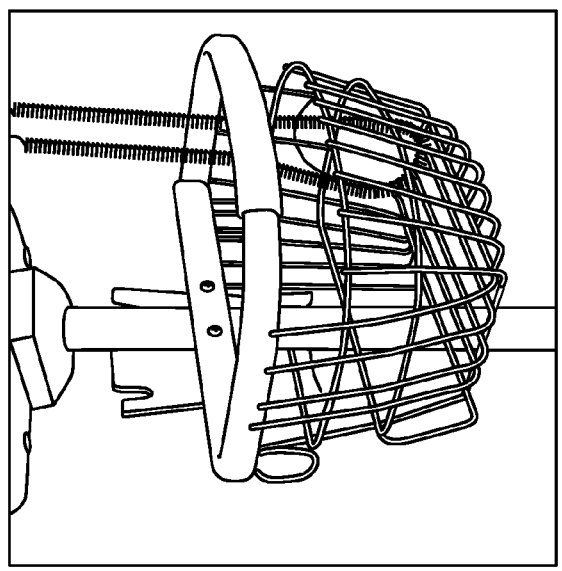
Figure 1F:
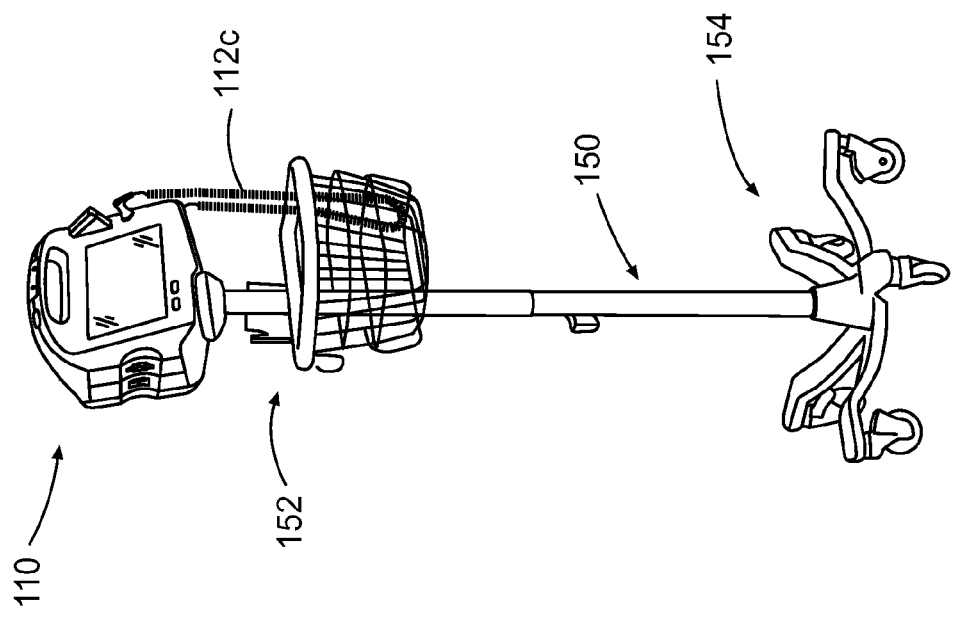

FIG. 1F illustrates the MF 110 as it is mounted onto a mobile stand 150 to function as an embodiment of a mobile configuration. As shown, the mobile stand 150 includes an attached utility basket 152 and is supported by a plurality of wheels 154 that enable the MF 110 to be transported along a floor surface. A lower portion of the insulated conductor 112c is shown as being disposed within the utility basket 152. As shown, the utility basket 152 can be used to constrain the displacement of the insulated conductor 112c, also referred to as a cord.

The design of an HCE module, such as the modules 112-116 illustrated within FIGS. 1A-1D, allows for one design and method of manufacture that can be employed to manufacture one type of HCE module capable of being attached to and integrated within a plurality of different types of health care apparatus configurations. Upon integration, the interoperation of the HCE module with each type of configuration is indistinguishable across different types of apparatus configurations.

Such a design of an HCE module allows for separate inventories of each type of HCE module that do not need to be created or maintained based upon what particular type of apparatus configuration the HCE module is later attached to and integrated into. The aforementioned benefits alone yield improved design, manufacturing and quality control efficiency for a variety of HCE modules.

Further, such a design allows for quality control testing that can be performed for that module regardless of what type or particular apparatus configuration the HCE module is later integrated into. Also, such testing of the HCE module, can be performed, in whole or in part, while the HCE module is not attached to an apparatus configuration, but instead attached to another type of device, such as a personal computer, for example.

Furthermore, the functions performed by HCE modules typically require some form of federal drug administration (FDA) testing, and such FDA testing and approval can typically be performed upon each specific type of HCE module design and manufacture, regardless of what types of apparatus configurations that HCE module will later be integrated within. Hence, a CCI type of HCE module design, in some circumstances, can satisfy the FDA testing and approval requirements for a type of HCE module, regardless of how that HCE module is later integrated into a variety of different types of apparatus configurations, and without requiring separate and/or further FDA testing and approval of that HCE module, while it is integrated into each type of apparatus configuration.

FIGS. 2A-2F each illustrate a view of an embodiment of a module structure 210, also referred to herein as a module enclosure 210, shown in various states of assembly. These figures also illustrate an embodiment of a frame structure 260 that functions as the embodiment of the MF 110, in that it constitutes a supporting structure that provides a mechanical interface for supporting each of a plurality of health-care equipment modules at one time.

FIG. 2A illustrates a front perspective view of an embodiment of an assembled module enclosure 210. As shown, the module enclosure 210 has a generally rectangular shape and includes a front side having a face plate 214, also referred to as a front panel 214. The face plate 214 is designed to be detachable from the remainder of the module enclosure 210 and includes an upper forward flange 222a and a lower forward flange 222b. A rear side of the module enclosure 210 is located opposite to the front side 214 and also includes an upper rear flange 220a and a lower rear flange 220b. A recessed portion 218 can be seen from a left side perspective view of the module enclosure 210. The recessed portion 218 is also of a generally rectangular shape and is effectively notched out from the overall shape of the module enclosure 210.

Figure 2B:
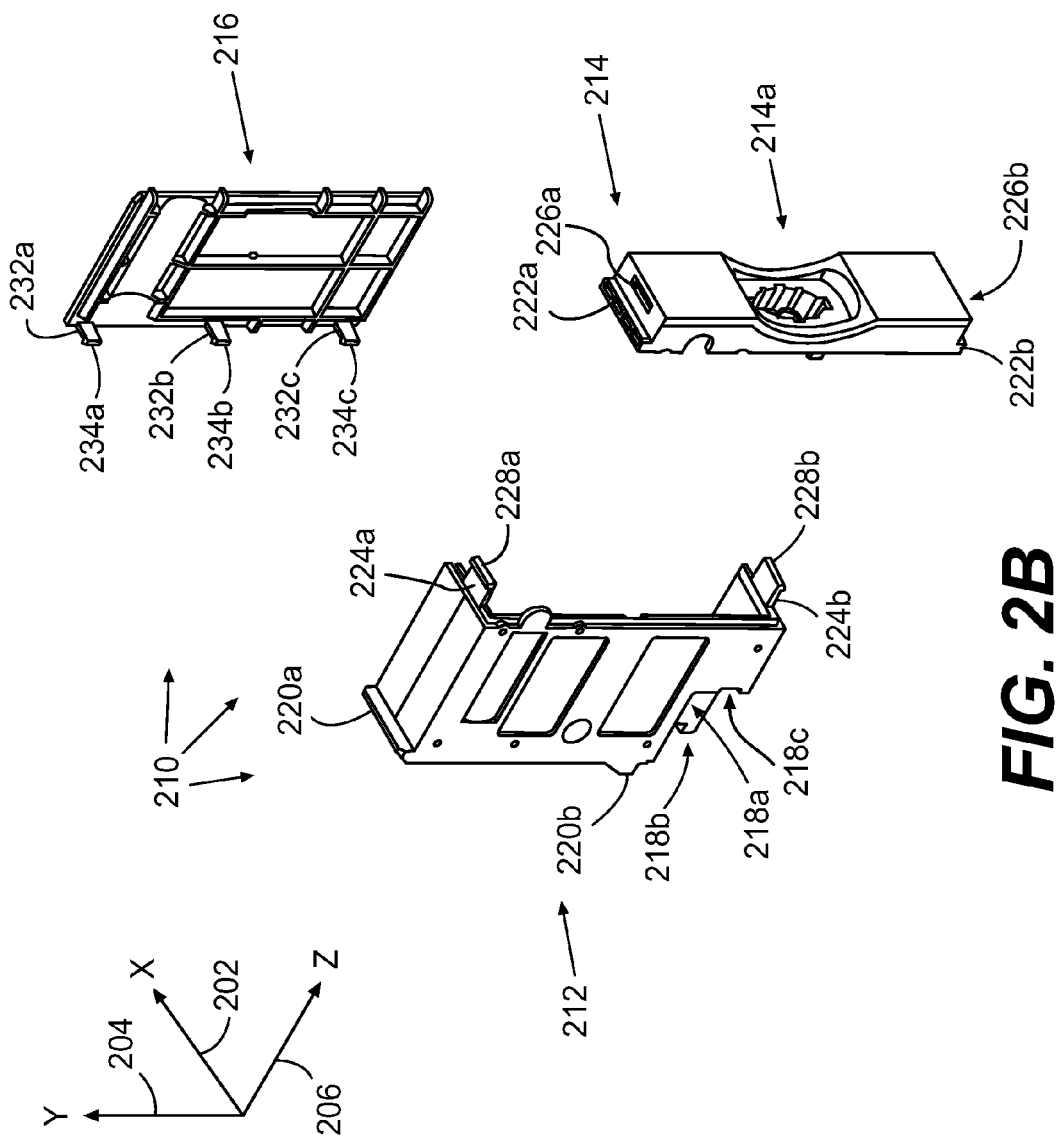

FIG. 2B illustrates a front perspective view of a disassembled module enclosure 210. As shown, the enclosure 210 is disassembled into three portions, including a main housing 212, a face plate 214 and a side panel 216. The face plate 214 is designed to attach to and detach from the main housing 212. Also, the side panel 216 is designed to attach to and detach from the main housing 212. In this embodiment, the face plate 214 is further designed so that it can attach to or detach from the main housing 212, whether or not the side panel 216 is also attached to the main housing 212. Also, the side panel 216 is further designed so that it can attach to or detach from the main housing 212, whether or not the face plate 214 is also attached to the main housing 212.

The face plate 214 shown, referred to as a first front panel configuration, can be substituted with one of a plurality of differently configured front panels that each have a configuration that may be unique and different from the first configuration shown. The first front panel configuration provides at least one of a mechanical, an electrical and a software interface between at least one module embedded component and a peripheral component located outside of the module enclosure 210, if at least one module embedded component is disposed within the module enclosure 210.

The first configuration provides at least one of a mechanical, an electrical and a software interface between at least one module embedded component and a peripheral component located outside of the module enclosure 210, if the at least one module embedded component is disposed within the module enclosure. Optionally, the peripheral component is a sensory device that interoperates with at least one module embedded component disposed within the enclosure. The front panel can, and typically does, provide a user interface between the module and a user of the module. Each of the differently configured front panels are further configured for attachment, detachment, and re-attachment to the enclosure 210.

The main housing 212 includes a recessed portion 218 bounded by an upper surface 218a (not directly shown from this view) and two side surfaces 218b (partially shown from this view) and 218c (not directly shown from this view) oriented perpendicular to each other. The upper surface 218a acts as a ceiling and the two side surfaces 218b, 218c act as walls within the recessed portion 218. The recessed portion 218 provides a cavity (volume of space) effectively notched out from the overall shape of the main housing portion 212 of the module enclosure 210.

A universal serial bus (USB) connector (not shown from this view, see 244 of FIG. 2C) is located along the side surface 218c of the recessed portion 218. A USB cable (not shown) located outside of the module enclosure 210 attaches to the module enclosure 210 while passing through the cavity of the recessed portion 218 and attaching to the (USB) connector (see 244 of FIG. 2C).

A first side surface 218b (partially shown) defines a plane oriented substantially parallel to a plane defined by the Y 204 and Z 206 axes, and is substantially perpendicular to a plane defined by the faceplate 214, as it is attached to the main housing 212 of the module enclosure 210. The second side surface 218c (not shown in FIG. 2A) defines a plane oriented substantially parallel to a plane defined by the X 202 and Y 204 axes and parallel to a plane defined by an outer surface of the faceplate 214, as the face plate 214 is attached to the main housing 212.

When attached to the main housing 212, the face plate 214 forms a front side of the enclosure 210 typically facing and physically accessible to a user of the HCE equipment. The face plate 214 includes an upper forward flange 222a and a lower forward flange 222b. A peripheral component connection port 214a resides within the face plate 214 and provides for a connection mechanism to one or more peripheral components (not shown). The peripheral components are located outside of the module enclosure 210 and are designed to interoperate with any embedded components (see 280 of FIG. 2F) located within the module enclosure 210. As shown, the connection port 214a is implemented as a mold insert into the face plate 214.

The face plate 214 is designed to be snap fit attached to the main housing 212. To implement the snap fit, the main housing 212 includes an upper protrusion 224a and a lower protrusion 224b, each dimensioned to engage an upper slot 226a and a lower slot 226b (engagement not shown from this viewing perspective) of the face plate 214. As shown, the slots 226a-226b each form a cavity within the face plate 214. The protrusions 224a-224b each include an end piece 228a-228b, respectively, designed to occupy the cavity formed by each respective slot 226a-226b when the face plate 214 is fully attached (engaged) to the main housing 212.

The side panel 216 is also designed to be snap fit attached to the main housing 212. To implement the snap fit, the side panel 216 includes an upper protrusion 232a, a middle protrusion 232b and a lower protrusion 232c dimensioned to engage an upper slot 242a, a middle slot 242b and a lower slot 242c of a rear side 240 of the main housing 212 (shown in FIG. 2C). The slots 242a-242c each form a cavity within the rear side 240 of the main housing 212. The protrusions 232a-232c each include an end piece 234a-234c designed to pass through the cavity formed by each respective slot 236a-236c of the rear side 240 of the main housing 212, when the side panel 216 is fully attached to the main housing 212.

FIG. 2C illustrates a rear-side view 240, a left-side view 246, a front-side view 248 and a bottom-side view 250 of the module enclosure 210 of FIGS. 2A-2B. The rear side 240 is substantially parallel to a plane defined by the X 202 and Y 204 axes. The viewing direction of the rear-side view 240 is substantially parallel to the Z axis 206. The viewing direction towards the left-side view 246 is substantially parallel to an X axis 202. The viewing direction towards the front-side view 248 is substantially parallel to a Z axis 206. The viewing direction towards the bottom-side view 250 is substantially parallel to a Y axis 204.

From the viewing perspective towards the rear side 240, the slots 242a-242c, the USB connector 244, recessed portion 218, the second side surface 218c bounding the recessed portion 218 and surrounding the USB connector 244 residing along the second side surface 218c, are visible. The module enclosure 210 is designed to electrically attach to a USB cable (not shown) via the USB connector 244. While attached to the USB connector 244, a portion of the USB cable occupying the cavity of the recessed portion 218 would be oriented (directed) substantially parallel to the Z axis 206 and substantially perpendicular to the second side surface 218c.

The left-side viewing perspective 246 shows the recessed portion 218 and the first side surface 218b bounding the recessed portion 218. As shown, the face plate 214 is shown from its left side and is attached to the main housing 212. From the bottom-side viewing perspective 250, the recessed portion 218 and the upper surface 218a bounding the recessed portion 218 are visible.

From the viewing perspective of the front side 248, the peripheral component connection port 214a is fully visible. The recessed portion 218 is not visible from this viewing perspective of the front side 248. While attached to the connection port 214a, a peripheral component (not shown) would attach to the module enclosure 212, typically via a tube or cable (not shown), while the attached tube or cable proximate to the connection port 214a is oriented substantially parallel to the Z axis 206.

Figure 2D:
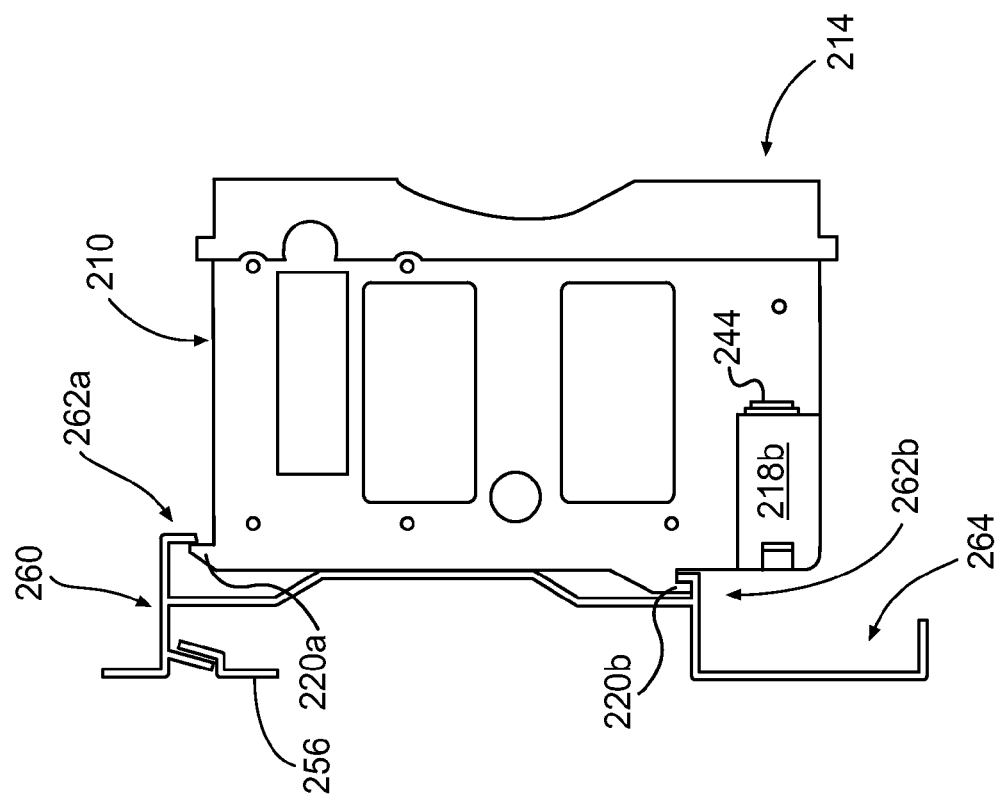
Figure 2E:
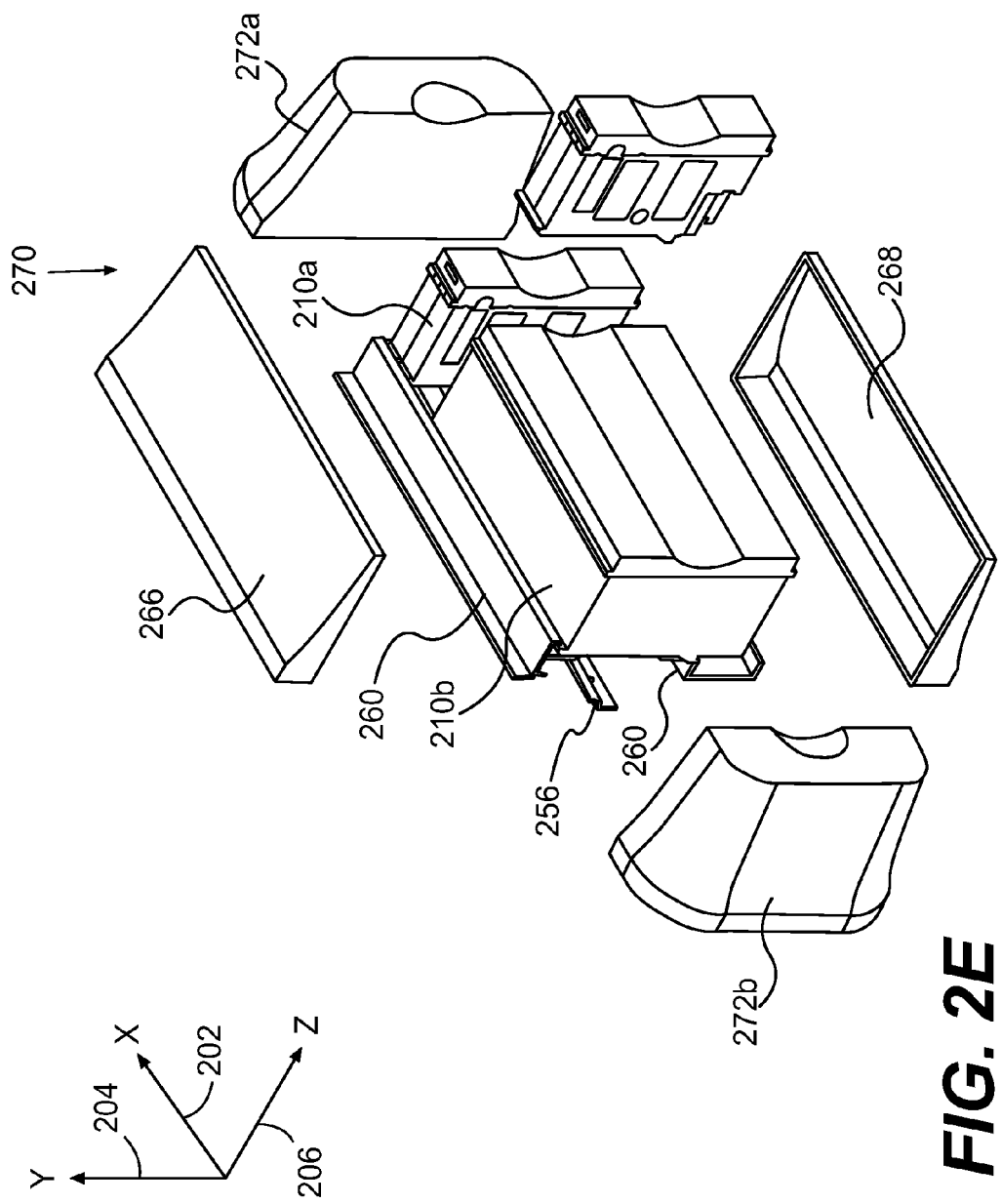

FIG. 2D illustrates a left-side view of the module enclosure 210 as it is attached to an embodiment of a frame 260. The embodiment of the frame 260 shown includes an upper rail 262a and a lower rail 262b. The module enclosure 210 includes an upper rear flange 220a and a lower rear flange 220b. As shown, the upper rear flange 220a of the module enclosure 210 is physically engaged with the upper rail 262a of the frame 260 and the lower rear flange 220a of the module enclosure is physically engaged with the lower rail 262b of the frame 260. Accordingly, a module structure (enclosure) 210 is classified as a frame attached component. A frame 260 resides within an integrated assembly (see 270 of FIG. 2E).

In this embodiment, the lower rail 262b restrains the module enclosure 210 from movement in a downward direction in response to forces of gravity. The upper rail 262a restrains the module enclosure 210 from movement in a clockwise rotational direction in response to forces of gravity. As a result, the module enclosure 210 is held stationary via physical engagement with the frame 260.

In this embodiment, the frame 260 is mounted onto a mounting rail 256 fixedly disposed onto a wall structure (not shown). As a result, the frame 260 is held stationary to the wall structure. In other embodiments, the frame 260 and portions and/or features of the frame, can be mounted onto or embedded into another type of structure.

For example, individual modules of the mobile frame of FIG. 1A each attach to a portion of the structure mobile frame 120 as if each module were attaching to the frame 260 of FIG. 2D. The flanges of each module make physical contact with structural features of the MF structure as if those MF structural features were an upper rail 262a or a lower rail 262b of a frame 260. The MF structural features each can act as a segment of an upper rail 262a or a lower rail 262b of the frame 260. Also, as a frame like structure it can be configured to be disposed stationary relative to such as a desktop or onto a mobile structure, (not shown) for example.

In this embodiment, the frame 260 is made from a rigid material, such as extruded aluminum or molded plastic having rigid properties of sufficient strength, for example, so that an insubstantial amount of deformation of the frame 260 occurs in response to the frame 260 supporting one or more module enclosures 210.

To disengage the module enclosure 210 from the frame 260, the lower rear flange 220b of the module enclosure 210 is lifted above the lower rail 262b and pulled away from the frame 260. Movement of the module enclosure 210 in the reverse direction engages the module enclosure 210 with the frame 260.

FIG. 2E illustrates a front perspective and exploded view of an integrated health care apparatus 270 including two module enclosures 210a-210b physically attached to a frame 260. The components within this view, when assembled together, form an integrated health care apparatus 270. The mechanical, electrical and software attachment between one or more modules and a frame is also referred to herein as an integrated apparatus or integrated assembly.

As shown, the mechanical interface between the frame 260 and the module enclosures 210a-210b, permits a first module enclosure 210a to be of a different width in relation to a second module enclosure 210b. Module enclosures of various widths can be arranged adjacent to each other in an ordered sequence along a long dimension of the frame 260. This type of integrated health care apparatus design provides for packing (horizontal stacking) of modules to eliminate unwanted spatial gaps between health care modules.

The module enclosure 210a is shown as having approximately the same dimensions as the module enclosure 210 shown in FIGS. 2A-2D. The width dimension of module enclosure 210b, which is defined as being a dimension parallel to the X axis 202 and a supporting rail of the frame 260, is substantially larger (wider) in dimension than the width dimension of the module enclosure 210a.

As shown, the frame 260 is designed to enable mechanical attachment to each of a plurality of health-care equipment modules 210a-210b at one time. The frame includes at least one supporting axis, co-axial with the lower rail 262b and substantially parallel to the X axis 202, and is oriented substantially orthogonal to the direction of gravity. The width dimension is measured along a dimension (axis) of the attached enclosure parallel to the supporting axis, while the enclosure is attached to the supporting rail. As a result, the mechanical interface permits an enclosure of a first module, to be of a different width in relation to a width of an enclosure of at least a second module, while both the first module and the second module are mechanically attached to the frame 260. A plurality of modules in addition to modules 210a-210b can be attached to the frame 260.

In some embodiments of the invention, each module enclosure 210 is sized in accordance with one of a set of discrete widths and where each discrete width is an integer number of multiple units of width. For example, each module enclosure can be dimensioned as a multiple of 35 mm units of width, such as 35 mm, 70 m, 105 mm etc. In these embodiments, each of the discrete widths are selected for a particular enclosure in accordance with a size of a module embedded component (not shown), also referred to herein as a module component, that can be disposed within the module enclosure 210a-210b.

In the embodiment shown, a power and computing component (PACC) (not shown here) is enclosed within the module enclosure 210b. The PACC is configured to transfer electrical power and data between itself and at least one other module embedded component via an electrical interface and a software interface. In this embodiment, the other module embedded component resides within the module enclosure 210a.

The frame 260 includes a cable passageway 264 (best shown in FIG. 2D) configured to accommodate passage of one or more universal serial bus (USB) cables (not shown). Each of the USB cables within the passageway are employed to provide an electrical pathway that enables transfer of power and data (electrical attachment/software connection) between the power and computing component 210b and a module enclosure 210a attached to the frame 260. Each of a plurality of these USB cables provide an electrical pathway to each respective one of a plurality of modules 210a attached to the frame 260 at the same time.

The integrated health care apparatus 270 includes other components, such as an upper housing panel 266 and a lower housing panel 268, and right end cap 272a and a left end cap 272b. The upper housing panel 266 and lower housing panel 268, also referred to as the upper plate 266 and the lower plate 268, are designed to make physical contact with the frame 260 and physical contact with the module enclosures 210a-210b while these plates 266-268 are attached to the frame 260. The end caps 272a-272b are designed to bound the module enclosures 210a-210b arranged adjacent to each other while attached to the frame 260. The end cap 272b also includes a power supply component (not shown) that supplies electrical power to the PACC 210b.

In this embodiment, the upper housing panel 266 snap fits over and around an upper portion of the frame 260 and an upper flange 222a of the modules 210a-210b in order to secure the modules 210a-210b into a stationary (locked) position while mechanically attached to the frame 260. When assembled, the upper housing panel 266 also contributes to a cosmetic appearance of the integrated apparatus 270.

The lower housing panel 268 snap fits under and around a lower portion of the frame 260 and a lower flange 222b of the modules 210a-210b in order to secure the modules 210a-210b into a stationary (locked) position while attached to the frame 260. The lower housing panel 268 also conceals wires, such as USB cables attached to the modules 210a-210b (see FIG. 3B) and passing through the cable passageway 264. When assembled, the lower housing panel 266 also contributes to a cosmetic appearance of the integrated apparatus 270.

When the upper housing panel 266 and the lower housing panel 268 are unattached to the integrated assembly 270, each module enclosure 210a-210b mechanically attached to the frame 260 is not attached in a locked position and can be lifted away from and detached from the frame 260 without having to move another module enclosure attached to the frame 260. When the end caps 272a-272b are unattached to the frame 260, each module 210a-210b mechanically attached to the frame 260 can be repositioned along the frame 260, simply by sliding it along the length of the upper rail 262a and lower rail 262b of the frame 260.

The frame 260, which is employed as a supporting structure for a module enclosure 210a-210b, can be incorporated into a variety of different configurations, including, for example, a desktop configuration (see FIGS. 4A-4D), a wall configuration (see FIGS. 5A-5D), a mobile configuration (see FIGS. 1A-1F), a hand-cartable configuration, or a bed configuration (see FIGS. 8A-8E, 9A-9D). A module enclosure 210a-210b can be attached, detached and re-attached into different types of configurations, such as between two or more of the aforementioned types of configurations.

FIG. 2F illustrates a view of a module enclosure 210 lacking a detached side panel 216 and including a module embedded component 280 disposed within the module enclosure 210. As shown, the side panel 216 of FIG. 2A is detached from the module enclosure 210 in order to reveal the module embedded component 280. The module embedded component 280 is designed to function as a portion of a non-invasive blood pressure measuring (NIBP) device. In operation, a peripheral tube component (not shown), also referred to as the tube, is connected between a blood pressure cuff (not shown) and the connection port 214a. Air transfers between the module embedded component 280 and a blood pressure cuff (not shown) is performed via the tube (not shown) and the connection port 214a (Shown in FIGS. 2A-2B).

As shown in the aforementioned FIGS. 2A-2F, the module structure 210 provides physical support relative to at least one module embedded component 280. The module embedded component 280 is configured to perform at least one function included within a provision of health care to a patient. The module structure 210 includes a mechanical interface that enables a mechanical attachment of the module structure 210 relative to a frame structure 260. The module embedded component 280 is configured for interoperation with a power and computing component 210b located separate from the module structure 210. The module structure 210 includes an electrical connection configured to provide a standardized electrical interface that enables transfer of at least one of standardized power and standardized data between the power and computing component and the at least one module component 280.

FIGS. 3A-3E each illustrate an aspect of an embodiment of a power and computing component. This embodiment of the power and computing component 210b, like that shown in FIG. 2D, is also referred to herein as a PACC 210b, and is implemented to deliver power and data to other components via a universal serial bus (USB). The universal serial bus (USB) is a standardized electrical interface configured (designed) to supply both electrical power and data.

FIG. 3A illustrates a simplified external view of the embodiment of the power and computing component (PACC) 210b like that shown in FIG. 2E. Like a module enclosure 210, the PACC 210b is designed as a frame attached component and when it is attached to a frame of an integrated apparatus, it resides within the integrated apparatus. As shown, the PACC 210b includes a first set of five (5) power and/or data connectors 312a-312e and a second set of five (5) power and/or data connectors, also referred to herein as the connectors 312a-312e and 314a-314e. These connectors 312a-312e and 314a-314e are physically located along an outer surface of the PACC 210b and are accessible for electrical attachment with other components via a plurality of USB cables (not shown).

In some embodiments, the connectors of the first set 312a-312e and of the second set 314a-314e are assigned for separate purposes. For example, in the embodiment shown, the connectors of the first set 312a-312e are assigned as "external device" connectors for interfacing with one or more devices that reside external to the integrated apparatus within which the PACC 210b and other modules reside. These external devices are not attached to the frame nor to any frame attached module enclosure residing within the integrated apparatus within which the PACC 210b resides. Separately, the connectors of the second set 314a-314e are assigned as "internal" connectors for interfacing with apparatus integrated components, referred to as internal components, that reside internal to the apparatus configuration within which the PACC 210b resides.

A module enclosure mechanically attached to a frame within an apparatus configuration is classified to reside internal to the apparatus configuration. Other components attached to that module enclosure, such as one or more module-embedded components that reside internal to the module enclosure, or peripheral components that reside external to the module enclosure, are classified and referred to as residing within the apparatus configuration within which the module enclosure resides.

A PACC 210b attached to the frame 260 of an apparatus configuration, also resides within (internal to) that apparatus configuration. Devices that do not reside within a particular apparatus configuration are referred to herein as "external devices" relative to that particular apparatus configuration. Alternatively, in other embodiments, the connectors 312a-312e, 314a-314e can each be assigned differently with respect to interfacing with various "internal" components or "external" devices.

Within the embodiment shown, the connectors 312a-312e, 314a-314e are implemented as universal serial bus (USB) connectors. Each connector 312a-312e, 314a-314e functions as a standard or non-standard universal serial bus (USB) end point connection 312a-312e, 314a-314e. Within this embodiment, external connectors 312a-312e, are implemented as standard USB connectors. Unlike the external connectors 312a-312e, the internal connectors 314a-314e are implemented as non-standard (extra functioning) USB connectors.

In accordance with the USB standard, each standard USB end point connection 312a-312e is configured to supply electrical power in the form of 5 volts of direct current (DC) and at a maximum supply rate of 0.5 amperes (500 milliamperes) of current, yielding a maximum of 2.5 watts of electrical power available to be received (drawn) by another USB connected component. In accordance with the invention, each non-standard USB end point connection 314a-314e is configured to supply electrical power in the form of 5 volts of direct current (DC) and at a maximum supply rate substantially in excess of 0.5 (500 milliamperes) of current, yielding a maximum of electrical power substantially in excess of 2.5 watts.

In some embodiments, the non-standard USB end points are each configured to supply a maximum of about 1.5 amperes of current. In some embodiments, a total aggregate current is limited to a maximum of about 7.5 watts of electrical power available to be received (drawn) by USB connected components.

Each USB end point connection 312a-312e, 314a-314e, whether it be a standard 312a-312e or a non-standard 314a-314e connection, is also configured to bi-directionally transfer digitized information between the PACC 210b and one or more components other than the PACC 210b, such as for example, to transfer to and/or from a module embedded component (not shown) residing inside (internal to) the module enclosure 210a.

As shown, in this embodiment, the module enclosure 210a includes a power and/or data connector 244 implemented as a USB end point connector 244. The connector 244 is disposed within a recessed portion 218 of the module enclosure 210a of a particular HCE module. The module enclosure 210a embodies a module and can enclose (include) one or more module-embedded components (not shown).

As shown, a USB cable 308 is disposed between the PACC 210b and the module enclosure 210a. The USB cable 308 is configured to be physically connected (not shown) between a PACC USB connector 312a-312e, 314a-314e and a USB connector of a component other than the PACC 210b (another component), such as the module USB connector 244 of module enclosure 210a. Alternatively, the cable 308 can be physically connected to a USB connector (not shown) of another module enclosure (not shown) residing within the apparatus configuration, or to another device (not shown) not residing within the apparatus configuration. The USB cable 308 provides an electrical connection between the PACC 210b and other components residing within an integrated apparatus, such as, for example, within the module enclosure 210a, as shown.

When connected, the USB electrical connection provides power from the PACC 210b to the other components such as to one or more module-embedded components (not shown) that reside within the module enclosure 210a (shown). The USB electrical connection further enables bi-directional transfer of information, encoded as digitized data, between the PACC 210b and other components, including for example, one or more module-embedded components residing inside (internal) to the module enclosure 210a or module-embedded components residing inside (internal) to other module enclosures (not shown) or to peripheral components residing outside of and electrically connected to a module embedded component within a module enclosure, or to devices residing outside of the apparatus configuration altogether.

Figure 3B:
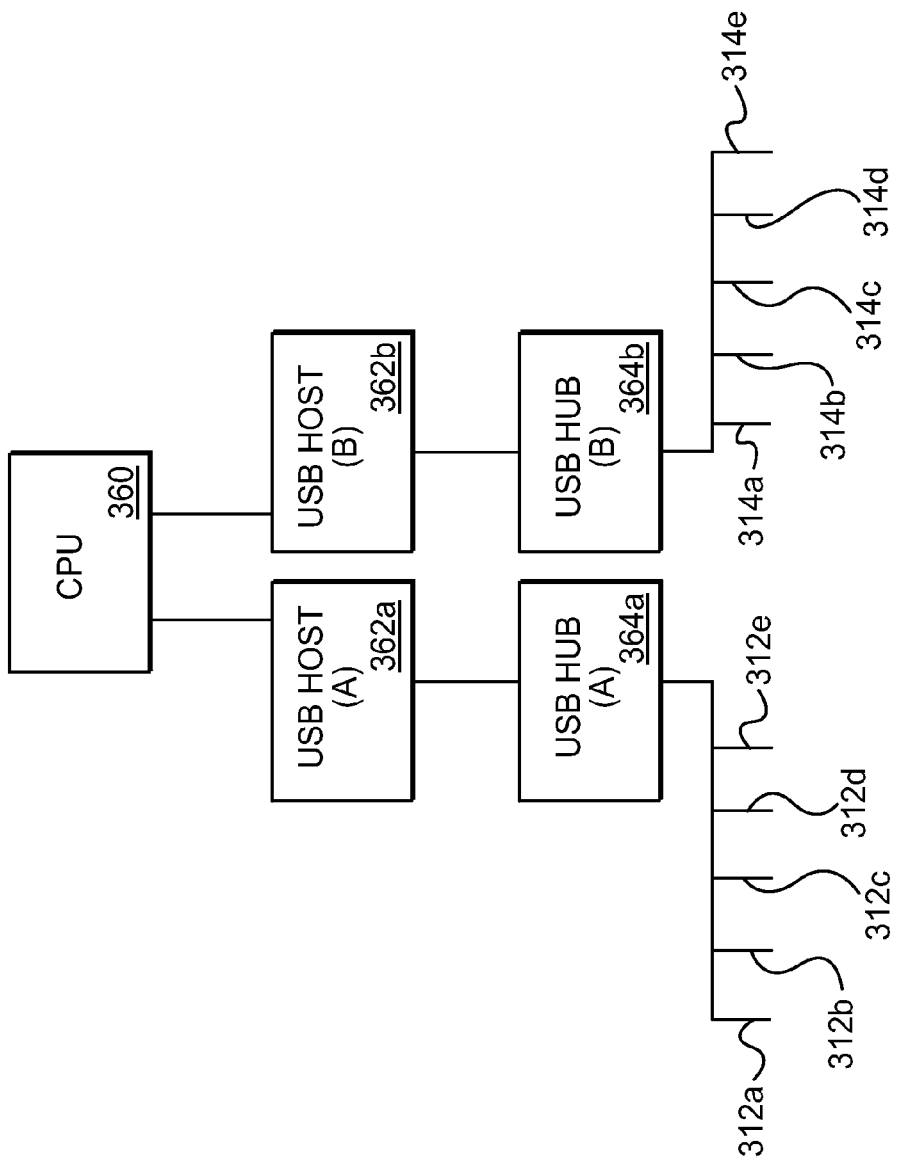

FIG. 3B illustrates a simplified block diagram of some of the internal components of the power and computing component (PACC) 210b. As shown, a central processing unit (CPU) 360 interfaces (communicates) with each of two (2) USB host components 362a-362b. The non-module USB host component 362a is configured to interface (communicate) with a USB hub component 364a. The USB hub component 364a is configured to interface (communicate) with each of the five (5) USB end point connectors 312a-312e. The USB host component 362b is configured to interface (communicate) with a USB hub component 364b. The USB hub component 364b is configured to communicate with each of the five (5) USB end point connectors 314a-314e.

Figure 3C:
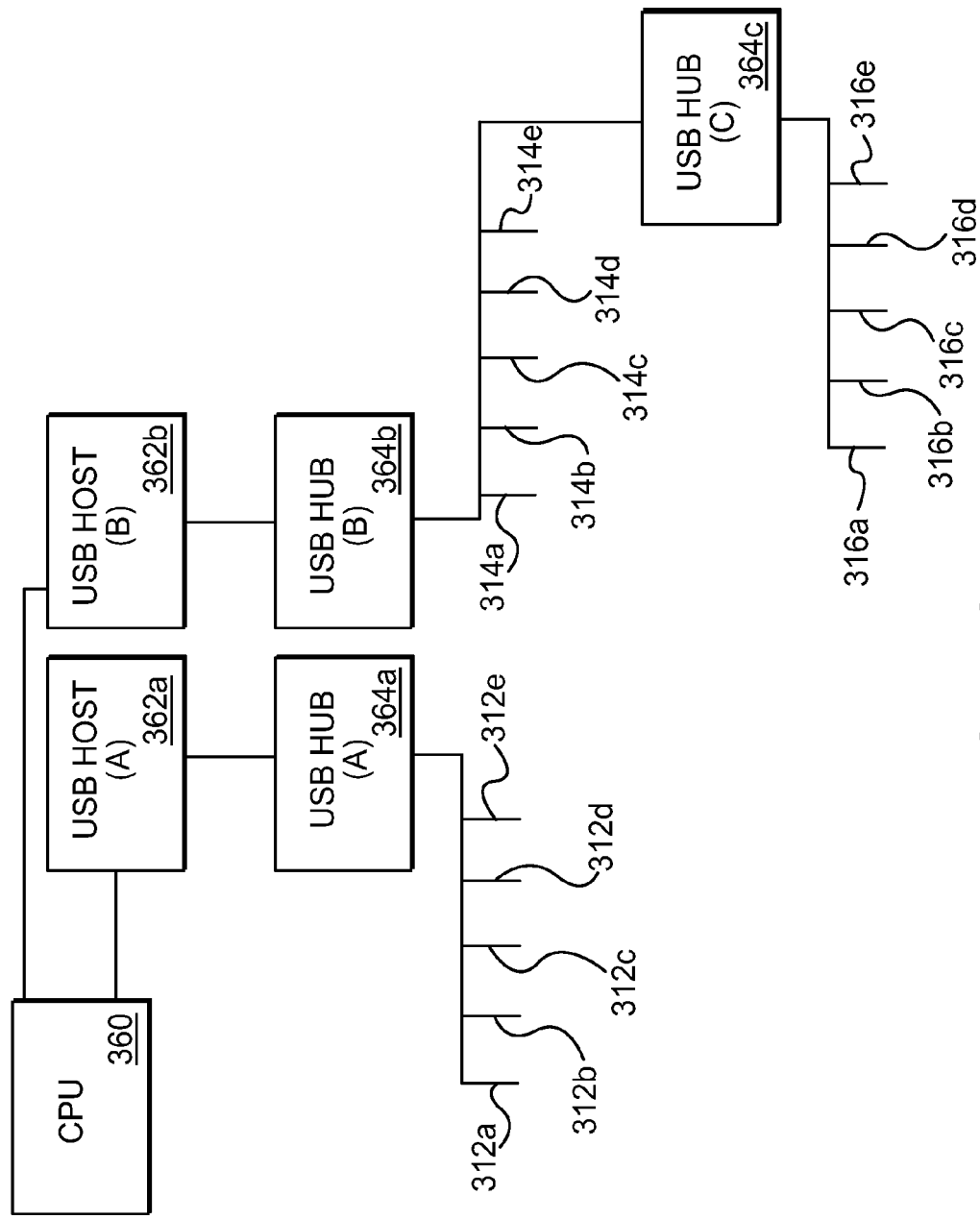

The USB design incorporates four (4) conductors. Of these four (4) conductors, two (2) conductors are employed to transfer electrical power and two (2) conductors are employed to transfer data. The FIGS. 3B and 3C represent the transfer of binary encoded information (data) between the CPU 360 and a USB host 362a, 362b, and the transfer of binary encoded information (data) between a USB host 362a, 362b and a USB end point 312a-312e and 314-314e respectively. The transfer of electrical power to each USB end point does not occur along the same path as data, but such transfer of power to a USB end point is arranged via a power bus (not shown) which is separate from the data paths shown in FIGS. 3B and 3C.

In this embodiment, the first set of external device connectors 312a-312e are assigned to interface with devices that reside external to the apparatus configuration. As previously described, these external devices are not attached to module enclosures 210a that reside within an apparatus configuration within which the PACC 210b resides. These external device connectors function as standard USB end points, meaning that no more than about 0.5 amperes of current is permitted to flow to an "external device" through this particular USB end point (connector).

When an external device is electrically connected to one of these external device USB end point connectors 312a-312e, the USB host component 362a detects such an electrical connection event, permits 100 milliamps of electrical current to flow to the external component, and initiates a USB protocol session with that component. During the USB protocol session, information is exchanged between the USB host 362a and the external device. During the USB protocol session, the external device identifies itself by communicating to at least one of a vendor identification value and a product identification value and negotiates USB connection parameters, including a maximum amount of current that the device will be allowed to draw from the PACC 210b during its normal operation.

In accordance with USB standards, the device is permitted to draw up to about 500 milliamperes of current during its normal operation. If during the USB protocol session, the device does not communicate a vendor identification value and a product identification value that represents a device permitted to interoperate within the integrated apparatus, then the device has failed to successfully complete the USB protocol session and as a result, the PACC 210b will terminate transfer of electrical power to the device. Hence, the device is denied electrical power from the PACC 210b.

Conversely, if the device communicates a vendor identification value and a product identification value that represents a device permitted to interoperate within the integrated apparatus, then power continues to be transferred in an uninterrupted fashion to the device during its normal operation. Hence, interoperation between the PACC 210b and the device is permitted or denied based upon successful transfer of at least one of a valid vendor identification value and a valid product identification value.

Within this embodiment, the second set of connectors 314a-314e are assigned to interface with internal components that reside within the integrated apparatus within which the PACC 210b resides. These internal components are typically embedded or attached to module enclosures attached to and reside internal to the apparatus configuration. These internal component connectors 314a-314e function as non-standard and extra functioning USB end points that can optionally supply electrical current substantially in excess of 500 milliamperes. When an internal component, such as a module attached or embedded component, is electrically connected to one of these internal USB end point connectors 314a-314e, the USB host component 362b detects such an event, and permits 100 milliamps of electrical current to initially flow to the component, and initiates a USB protocol session with that component. During the USB protocol session, information is exchanged between the USB host 362b and the internal component.

As described above in association with external devices, during the USB protocol session, the internal component identifies itself by communicating at least one of a vendor identification value and a product identification value and negotiates USB connection parameters, including a maximum amount of current that the device will be allowed to draw from the PACC 210b during its normal operation. As an exception to USB standards, the device is permitted to draw substantially in excess of 500 milliamperes of current during its normal operation.

As described above in association with external devices, if during the USB protocol session, the internal component does not communicate a vendor identification value and a product identification value that represents a component permitted to interoperate within the integrated apparatus, then the component has failed to successfully complete the USB protocol session and as a result, the PACC 210b will terminate transfer of electrical power to the internal component. Hence, the internal component is denied electrical power from the PACC 210b.

Conversely, if the internal component communicates a vendor identification value and a product identification value that represents a device permitted to interoperate within the integrated apparatus, then power continues to be transferred in an uninterrupted fashion to the device during its normal operation. Hence, interoperation between the PACC 210b and the internal component is permitted or denied based upon at least one of the vendor identification value and the product identification value.

During the USB protocol session, the internal component negotiates USB connection parameters, including a maximum amount of current that the device will be allowed to draw from the PACC 210b via the internal USB connector 314a-314e. In some embodiments, the internal component is allowed to draw up to about 1500 milliamperes of current from the PACC 210b via one of the USB connectors 314a-314e.

Upon successfully completing the USB protocol session, a communications protocol such as, for example, Welch Allyn Communications Protocol (WACP) session may be initiated to further exchange WACP related information between software executing on the PACC 210b and software executing on the internal component. In some embodiments, during the WACP session, the internal component transfers (communicates) a global unique identifier (GUID) via the USB connection that further identifies the internal component to software executing within the PACC 210b.

If the internal component fails to successfully perform within the communications protocol session, the PACC 210b will terminate transfer of information with the internal component and will continue to provide only electrical power to the device. Conversely, if the internal component continues to successfully perform within the communications protocol session, then power and information transfer continue in an uninterrupted fashion to the internal component during its normal operation.

The PACC 210b receives electrical power transferred from a separate power supply (not shown). In some embodiments, the separate power supply includes an alternating current (AC) to direct current (DC) transformer disposed within an end cap 272b. In some embodiments, the transformer (not shown) supplies 15 volts of voltage and 4 amperes of current to the PACC 210b. Because the PACC 210b has a limited total current that it can supply at any one time, in some circumstances, the PACC 210b may not be able to supply a particular amount of current requested by a particular internal component or requested by a external device USB through a particular end point connection 312a-312e, 314a-314e.

The PACC 210b is designed to supply a limited maximum total amount of current at any one point in time. For example, 500 milli-amperes of current were requested to be supplied to each of the ten (10) USB connectors 312a-312e, 314a-314e at a particular point in time, then the PACC 210b would be required to supply 5 amperes of total current at that one point in time.

In some circumstances, the cumulative demand for current from the connectors 312a-314e may exceed a maximum amount of current that can be supplied by the PACC 210b at a particular point in time. In this circumstance, software executing on the CPU 360 within the PACC 210b can optionally cause one or more USB end points to not be supplied a requested amount of current in order to supply current to other USB end points.

In some circumstances, the USB host 362a, 262b can transmit via the USB protocol to the internal component or external device, a notice (status information) that an amount of current requested by the component or device cannot be supplied to the component or device at that particular time. As a follow up action, the amount of current supplied through a USB end point 312a-312e, 314a-314e to the component or device is reduced for a period of time until further notice (status information) is transmitted from the USB host 362a, 362b to the USB end point supplying current to a component or device.

At a later point in time, a further notice (status information) can be transmitted from the USB host 362a, 362b to the component or device indicating that more current or sufficient current to satisfy the requested current is available. For example, this status information can be communicated to a module 210b via an internal USB connector 314a-314e, indicating that more current and/or the total requested current is currently available. As a responsive action, the amount of current drawn by the module component or device and supplied through a USB end point 312a-312e, 314a-314e to the module component or device is raised accordingly.

In some circumstances, the software can direct the USB host 362a, 362b to transmit a command through a particular USB end point 312a-312e, 314a-314e to a receiving internal component or external device to cause that component or device to transition to a sleep mode. Such a transition can occur from another mode, such as from a normal mode of operation to the sleep mode. While operating in sleep mode, the component or device requires and draws a substantially lower amount of current than an amount of current drawn during its normal operation.

At a later point in time, the software can direct the USB host 362a, 362b to transmit a command through a particular USB end point 312a-312e, 314a-314e to the receiving internal component or external device to cause that component or device to transition to normal operation when an amount of current sufficient to support the normal operation of the component or device becomes available.

FIG. 3C illustrates a simplified block diagram of some of the internal components of a second embodiment of the power and computing component (PACC) 310. Like the embodiment of FIG. 3B, the internal components include the (CPU) 360 interfacing with two (2) USB host components 362a-362b which each interface with USB hub component 364a and 364b respectively, which each interface with the five (5) USB end point connectors 312a-312e and five (5) USB end point connectors 314a-314e, respectively.

Unlike the embodiment of FIG. 3B, the end point connectors 312a-312e and 314a-314e are all assigned to interface with internal components and to function as non-standard and extra functioning USB end points that can optionally supply electrical current substantially in excess of 500 milli-amperes. Furthermore, one (1) of the end point connectors 312a-312e and 314a-314e is assigned to interface with a third USB hub 364c instead of interfacing with an internal component or an external device. The third USB hub 364c interfaces with five (5) USB end points 316a-316e, which are not included within the embodiment of FIG. 3B and are assigned to function as standard USB end points 316a-316e and to interface with external devices.

In accordance with the arrangement of USB components within this embodiment, the USB standard permits a USB hub 364a-364c to interface with another USB hub as if it were a USB end point. Consequently, a plurality of USB hubs can be interfaced and nested among other USB end points in this fashion in accordance with the USB standard.

Figure 3D:
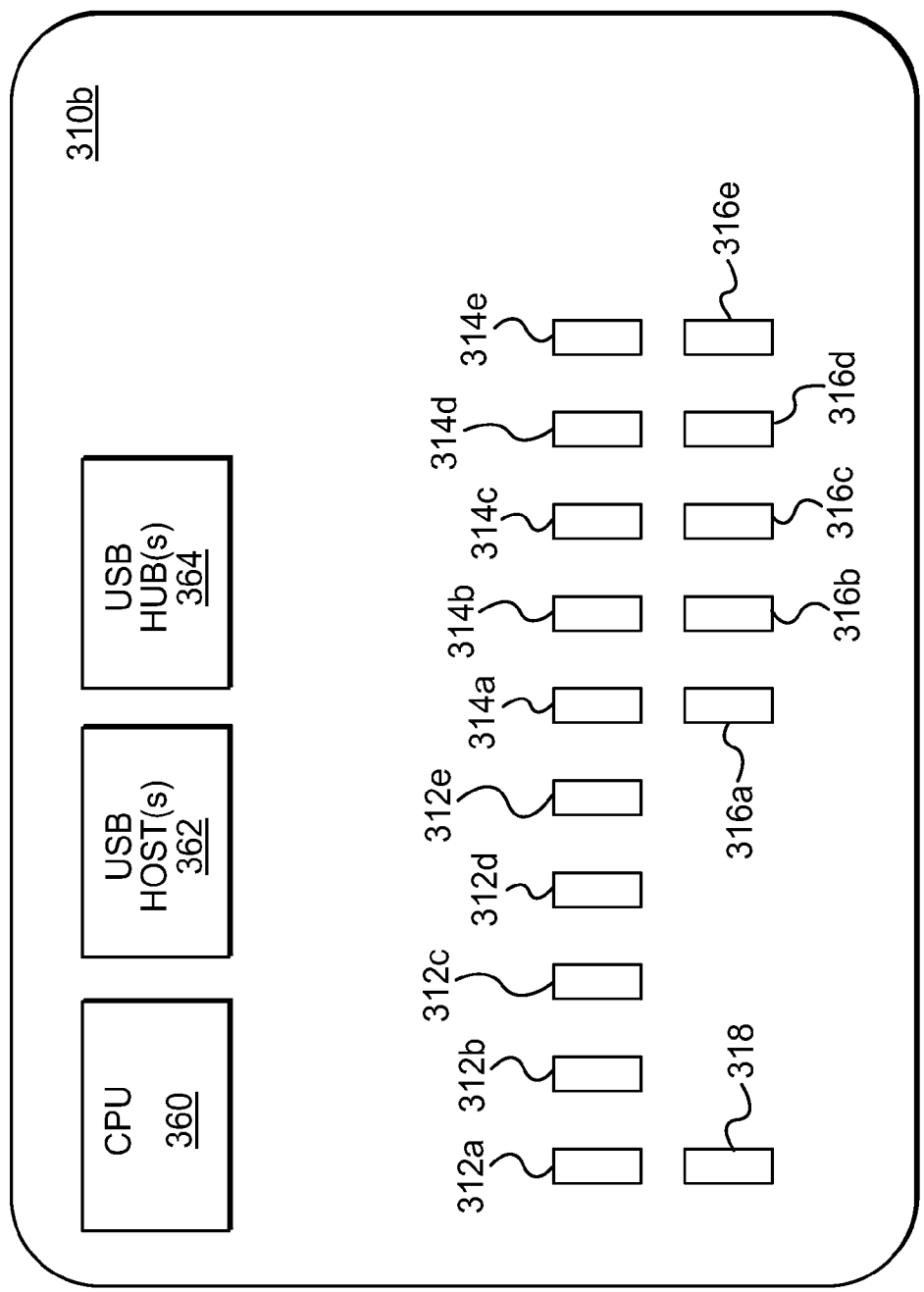

FIG. 3D illustrates a simplified view of a second embodiment of the PACC 310 implemented within an electronic circuit board. Like the PACC 210b of FIG. 3A, the PACC 310 includes a plurality of USB end point connectors 312a-312e and 314a-314e. Unlike the PACC 210b, the PACC 310 further includes an additional plurality of USB end point connectors 316a-316e. The USB end point connectors 312a-312e, 314a-314e and 316a-316e assigned in accordance with the diagram of FIG. 3C.

The second embodiment also includes a special USB receiving end point 318. As opposed to other USB end points (end point connections) 312a-312e, 314a-314e and 316a-316e designed to transmit electrical power, the USB end point 318 is designed to receive power and to transfer data to another host device, such as a personal computer. In such a scenario, the integrated apparatus is configured to act as a USB slave device to another device, such as a personal computer.

The PACC 310 implemented on a circuit board 312 is appropriate for incorporation into the mobile frame apparatus (MF) 110 of FIGS. 1A-1F. The circuit board 312 resides within a cavity (not shown) of the MF 110. The cavity enables a USB cable connection between each USB end point 312a-312e and each module 112-116 that resides within the MF 110.

As opposed to the linear arrangement of frame attached modules shown in FIG. 2E, and later shown in FIGS. 4A and 5A, the modules of the MF 110 are not all arranged along one line. For example, module 112 of the MF is not arranged along a same line as modules 114 and 116. Also, there is no frame attached and packaged PACC 210b within then MF 110. Instead, the MF 110 includes an embedded and non-separately packaged PACC 310 implemented as a circuit board.

Each USB end point connection to a module can include a 5 volt to 5 volt isolation transformer (not shown) that resides within the module. This transformer provides galvanic protection to a user and/or patient that may come into physical contact with the module. The transformer provides protection from a possible malfunction in the apparatus that could cause excessive voltage and current to discharge from the apparatus and cause possible injury to the user or patient.

Figure 3E:
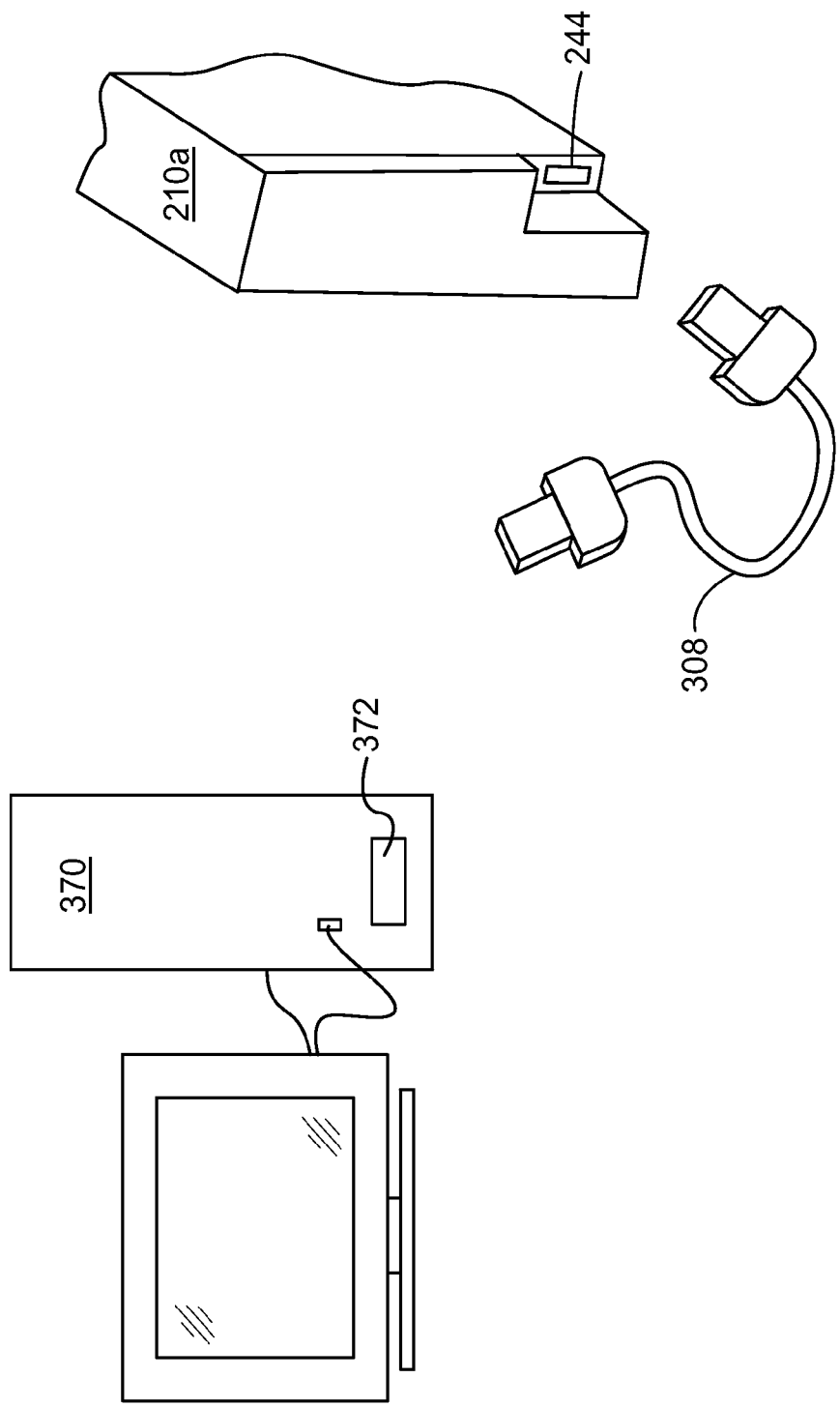

FIG. 3E illustrates a commercially available computer functioning as a power and computing component (PACC) via a standardized electrical interface provided by the computer. As shown, a computer 370 can function to test and operate one or more HCE modules 210a. The USB cable 308 can establish an electrical connection between a USB connector 372 and the USB connector 244 of the module 210a. Such a USB connector 372 is typically standard on many personal computers can connect to the USB cable 302.

As shown, the standardized electrical interface may be provided as a feature of a commercially available computer, so that the computer can function as an embodiment of the power and computing component. Many module embedded components, prior to being embedded into a module structure in accordance with the invention, could have been embedded within other prior art health-care equipment and supplied data and/or power from other than a standardized electrical interface.

In many embodiments, the module structure substantially encloses the module embedded component 280. In other embodiments of the invention, the module embedded component 280 can be removed from the module structure 210 and supplied via a standardized electrical interface in accordance with the invention.

The module embedded component can optionally include software for interoperation with the power and computing component. The software executing within the module embedded component operated in accordance with a software interface to enable a software connection between the power and computing component and the module embedded component. The software connection involves the execution of a communications protocol stack, such as for example, the Welch Allyn Communications Protocol stack. The software connection supported by and dependent upon the electrical (power and data) connection. In the embodiments shown, the electrical (power and data) connection is an USB end point connection.

Overall, the aforementioned use of the USB and its surrounding design and implementation provide an embodiment of a power and data transfer mechanism between a source of electrical power and at least one module component that resides internal to an apparatus, or to a device that resides external to an apparatus. That source of electrical power can be as convenient as a widely available personal computer or a wall outlet AC-DC transformer with a USB connection that can plug into a wall outlet.

FIGS. 4A-4D illustrate views of an integrated desk top mounted configuration 410. This configuration 410 includes a plurality of health-care equipment (HCE) modules 412-418 each designed to interoperate with a respective peripheral component 422-428 (see FIG. 4B).

Figure 4A:
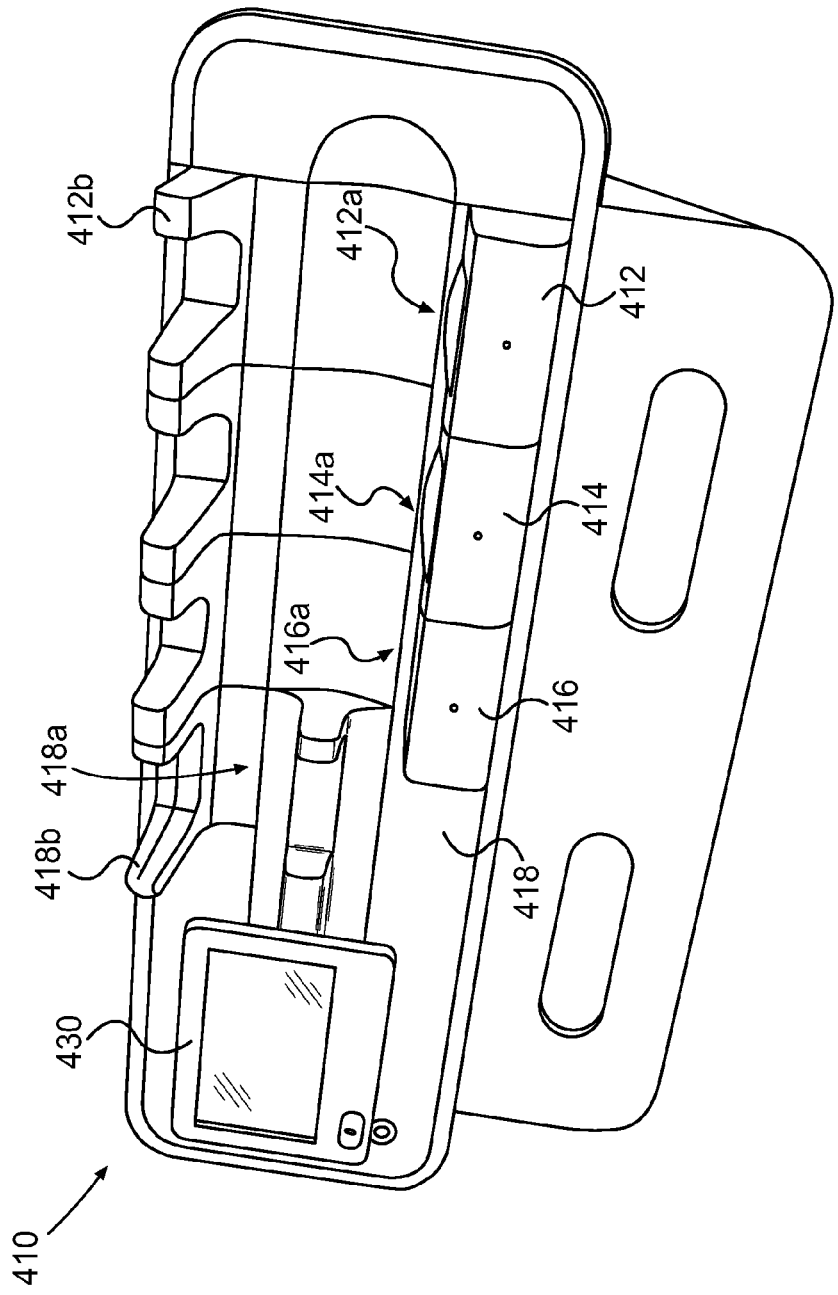
FIGS. 4A-4D illustrate views of an assembled desk top mounted configuration including a plurality of health-care equipment modules and peripheral components.

FIG. 4A illustrates a front side perspective view of an embodiment of a desktop configuration 410. As shown, the desktop configuration 410 includes four (4) HCE module enclosures 412-418 that each face and are each accessible from a front side of the apparatus 410. Each of these four (4) HCE modules 412-418 are designed to provide physical support to a peripheral component (see FIG. 4B). Physical support is provided via a docking cradle type of mechanical interface, also referred to herein as a docking station, or cradle 412-418.

The cradles 412-418 each include side protrusions, such as the side protrusion 412b and 418b, for example, that assist with providing physical support to a peripheral component 422-428 (see FIG. 4B) disposed within each respective cradle 412-418. Some of the cradles 412 and 414 each include a rectangular-shaped well opening 412a and 414a (shown in FIG. 2B, for example), respectively. The cradle 416 includes a circular well shaped opening 416a (shown in FIG. 2B, for example), respectively. The cradle 418a does not include a well.

In some embodiments, each cradle 412-418 further provides an electrical interface via an electrical connector (not shown) within each respective well to a peripheral component mechanically engaged with the cradle 412-418 via the well. The electrical interface being designed to transfer electrical power from the cradle 412-418 to the peripheral component. In some embodiments, the electrical interface further provides for transfer of data between the cradle 412-418 and the peripheral component, for example, by employing a USB interface between the cradle 412-418 and the peripheral component. Some peripheral components require no electrical power from a source external to the peripheral component, and may be self powered via an internal battery. Other peripheral components may not require any electrical power.

An electronic display screen (EDS) 430 is disposed to the left side of the module enclosure 418. The EDS 430 is designed to be touch sensitive and to provide a user interface to a user of the integrated apparatus 410 via electronic display of text and graphics. The EDS 430 is designed to interoperate with a PACC (see FIG. 2D) that resides internal to the apparatus 410. In some embodiments, the EDS is an LCD display screen. The display screen shown has a diagonal dimension of 8.9 inches.

Figure 4B:
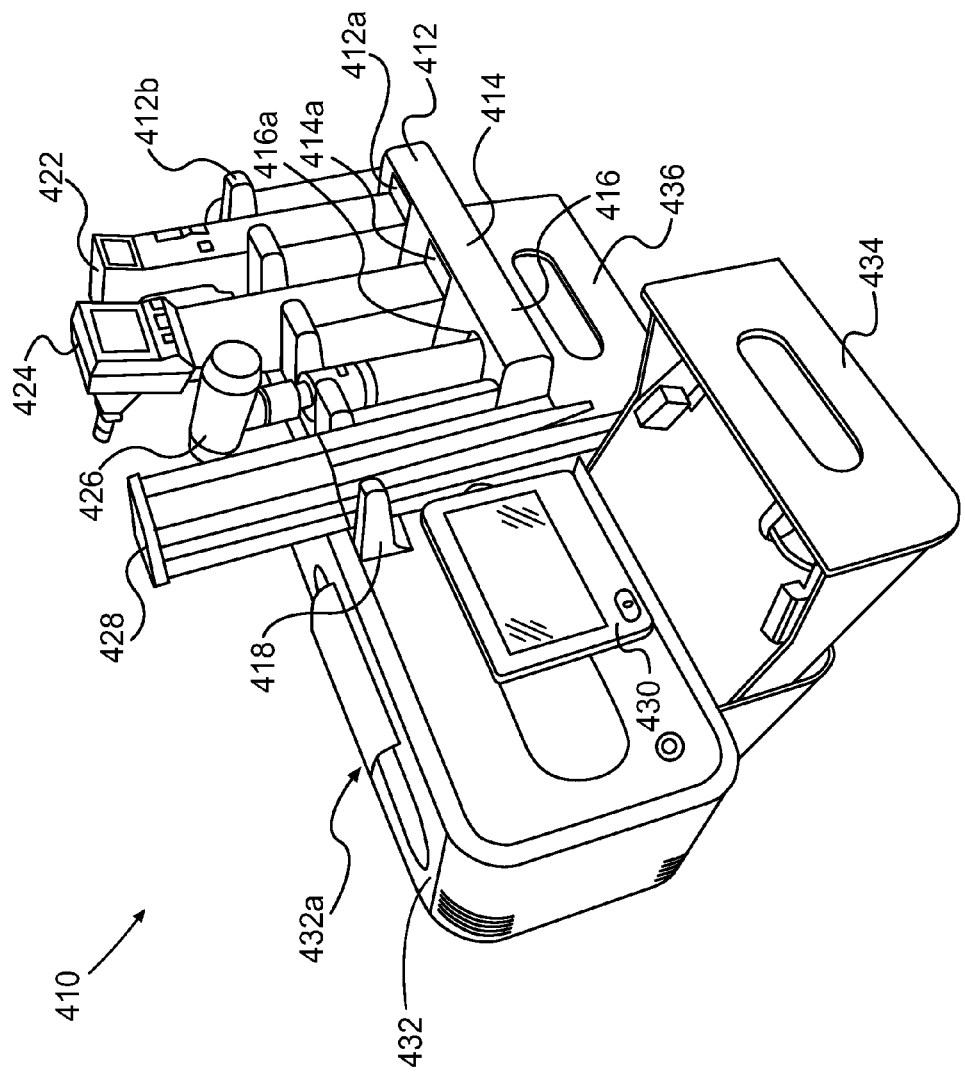

FIG. 4B illustrates a front side perspective view of the embodiment of FIG. 4A including hand held peripheral components 422-428 disposed within the cradles 412-418. Each cradle 412a-418a is manufactured as at least a portion of a customized face plate attached to each respective module enclosure.

As shown, a hand held component 422, is an audiometer 422 employed for measuring the acoustic sensitivity of a patient's ear, while the hand held component 424 is a tympanometer 424 employed for applying pressure to measure properties of an ear drum. Peripheral component 426 is an otoscope 426, which is a hand held sensory device employed for visual inspection of an ear or a nose cavity of a patient. Peripheral component 428 is an otoscope tip dispenser 428, designed to store and dispense tips designed to attach onto an otoscope 426.

The peripheral components 422-426 are classified as medical diagnostic instruments. Many other types of medical instruments can be integrated as a peripheral component that functions within a module. Such medical instruments include a rhinoscope, a laryngnoscope, an anoscope, an audiometer, a tympanometric instrument, a thermometer, and a vaginoscope, for example. In other embodiments, some modules function as non-electrical (mechanical only) devices. For example, a module can be implemented as a mechanical blood-pressure measuring device, a dispenser, a storage unit, and a cup holder.

A printer module 432 is located above the EDS 430. Printing can be initiated and controlled via the user interface provided by the EDS 430. The printer module 432 outputs printed paper through an external opening 432a located along the top side of the integrated apparatus 410. A pair of drawers 434, 436 are disposed on a lower side of the integrated apparatus 410. The drawers 434, 436 can be utilized for storage of items, typically related to the function of the HCE modules disposed within the apparatus 410.

Figure 4C:
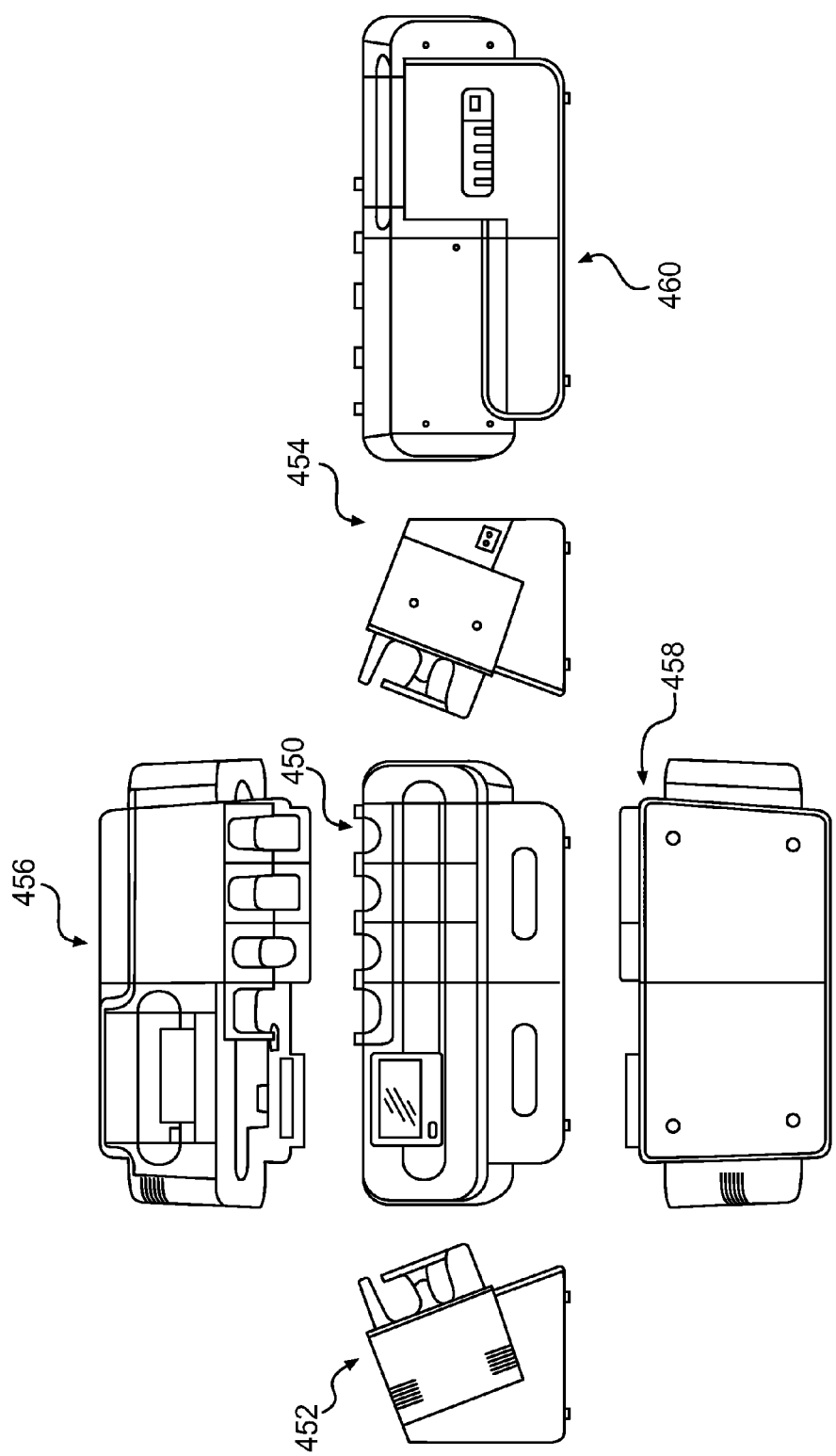

FIG. 4C illustrates a variety of views of the embodiment of a desktop configuration 410. View 450 illustrates the front side of the desktop configuration apparatus 410 like that shown in FIG. 4A, while view 452 illustrates the left side of the apparatus 410. View 454 illustrates a right side of the apparatus 410. View 456 illustrates an upper side of the apparatus 410, view 458 illustrates a lower side of the apparatus 410, and view 460 illustrates a rear side of the apparatus 410.

Figure 4D:
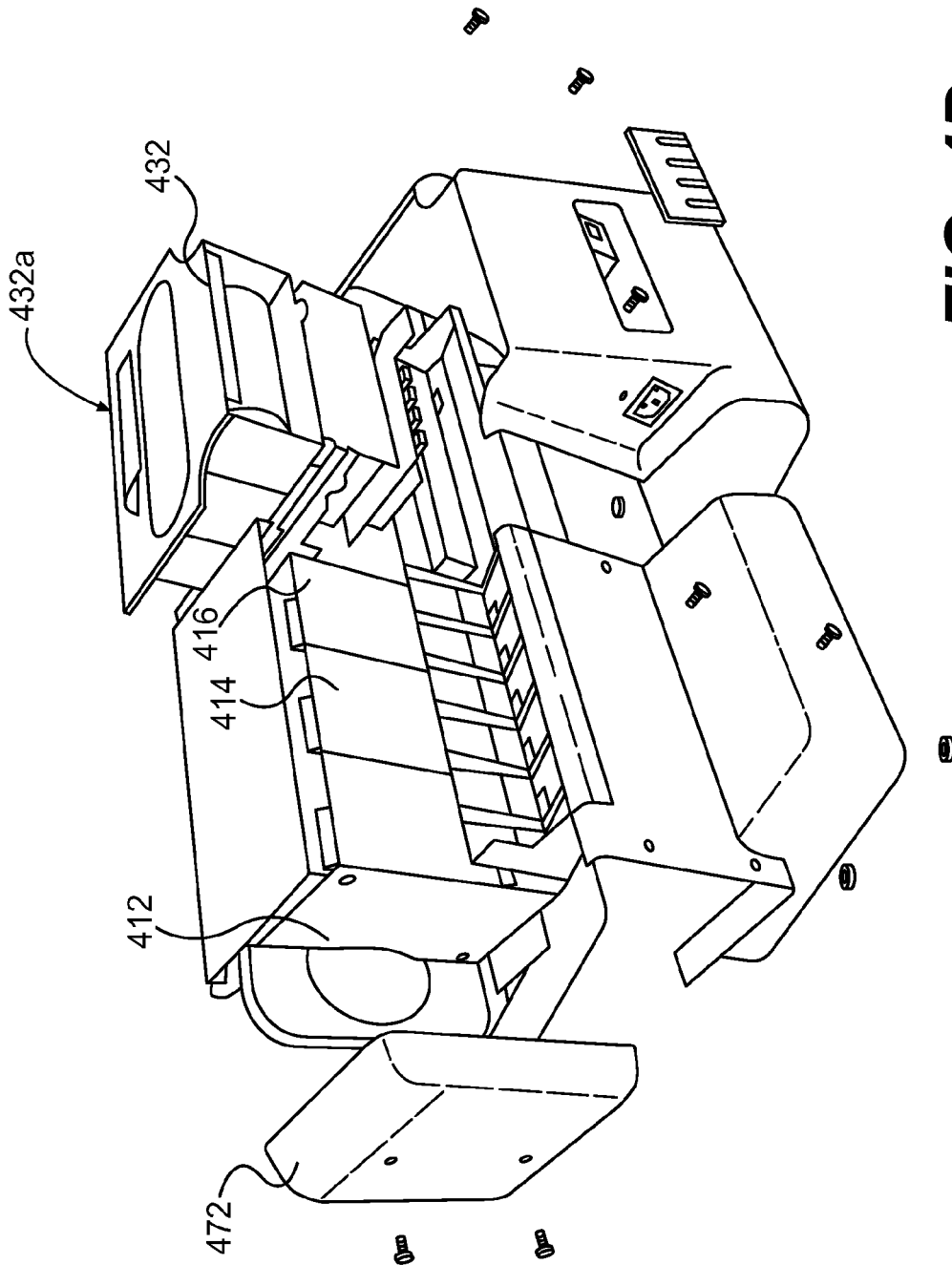

FIG. 4D illustrates a rear side exploded view of the desktop apparatus 410. A rear-side view of the module enclosures 412, 414 and 416 is shown. Also, a rear-side view of the printer 432 and its opening 432a is also shown. A right end cap 472 is also shown.

FIGS. 5A-5D illustrate views of an integrated wall mounted configuration 510. This configuration 510 includes a plurality of five (5) health-care equipment modules 512-520 each designed to interoperate with a respective peripheral component 422-428 (see FIG. 5B).

Figure 5A:
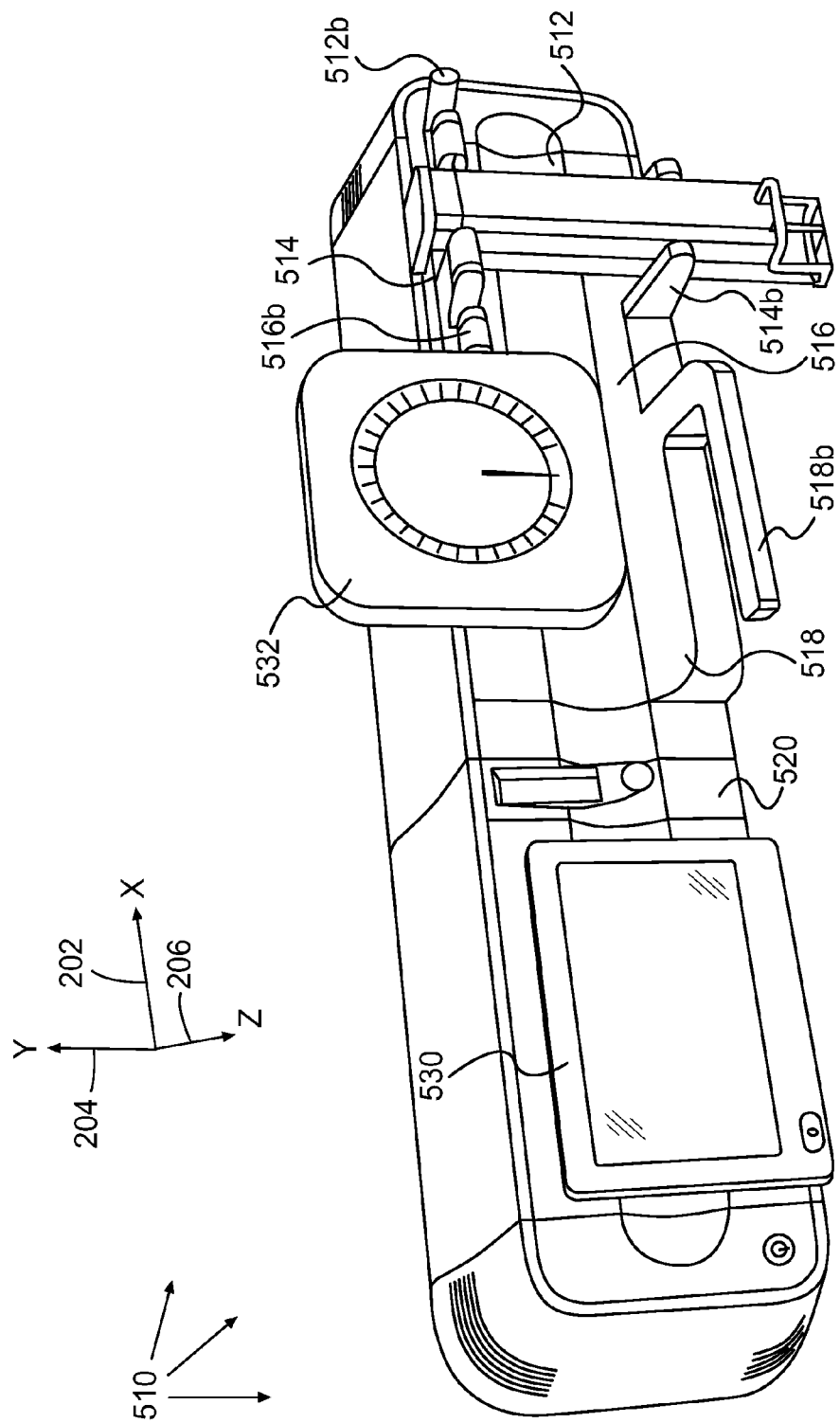
FIGS. 5A-5D illustrate views of an integrated wall mounted configuration. This configuration includes a plurality of five (5) health-care equipment modules each designed to interoperate with a respective peripheral component.

FIG. 5A illustrates a front side perspective view of an embodiment of a wall mounted configuration. As shown, the wall mounted configuration 510 includes four (4) HCE module enclosures 512-520 each accessible from a front side of the apparatus 510. Each of these four (4) HCE modules 512-520 is designed to provide some type of physical support to a hand accessible component (see FIG. 5B). Physical support for each hand accessible component is provided via supporting protrusions (512b-518b) that extend as a portion of the face plate of each module enclosure 512-518.

The module enclosures 512-516 are shown as having approximately the same dimensions. The width dimension of module enclosure 518, which is defined as being a dimension parallel to the X axis 202 and a supporting rail (not shown) within the apparatus 510, is substantially larger, about 3 times larger (wider) in dimension than the width dimension of each if the module enclosures 512-516. The module enclosure 520 is a temperature measuring module, like the temperature measuring module 112 shown in FIG. 1A. Also, a blood-pressure meter 532 is mounted onto the module enclosure 518. Hand accessible components designed to interoperate with the blood pressure meter 532 are shown in FIG. 5B.

An electronic display screen (EDS) 530, like that shown in FIG. 4B, is disposed to the left side of the module enclosure 520. The EDS 530 is larger and has a diagonal dimension of 7 inches and includes a larger pixel display area, than the EDS 430 of FIG. 4A. Like the EDS 430, the EDS 530 may be designed to be touch sensitive and provide a user interface to health care providers using the integrated apparatus 510 via electronic display of text and graphics. The EDS 530 is designed to interoperate with a power and computing component (not shown) that resides internal to the apparatus 510. In some embodiments, the EDS is an LCD display screen.

Figure 5B:
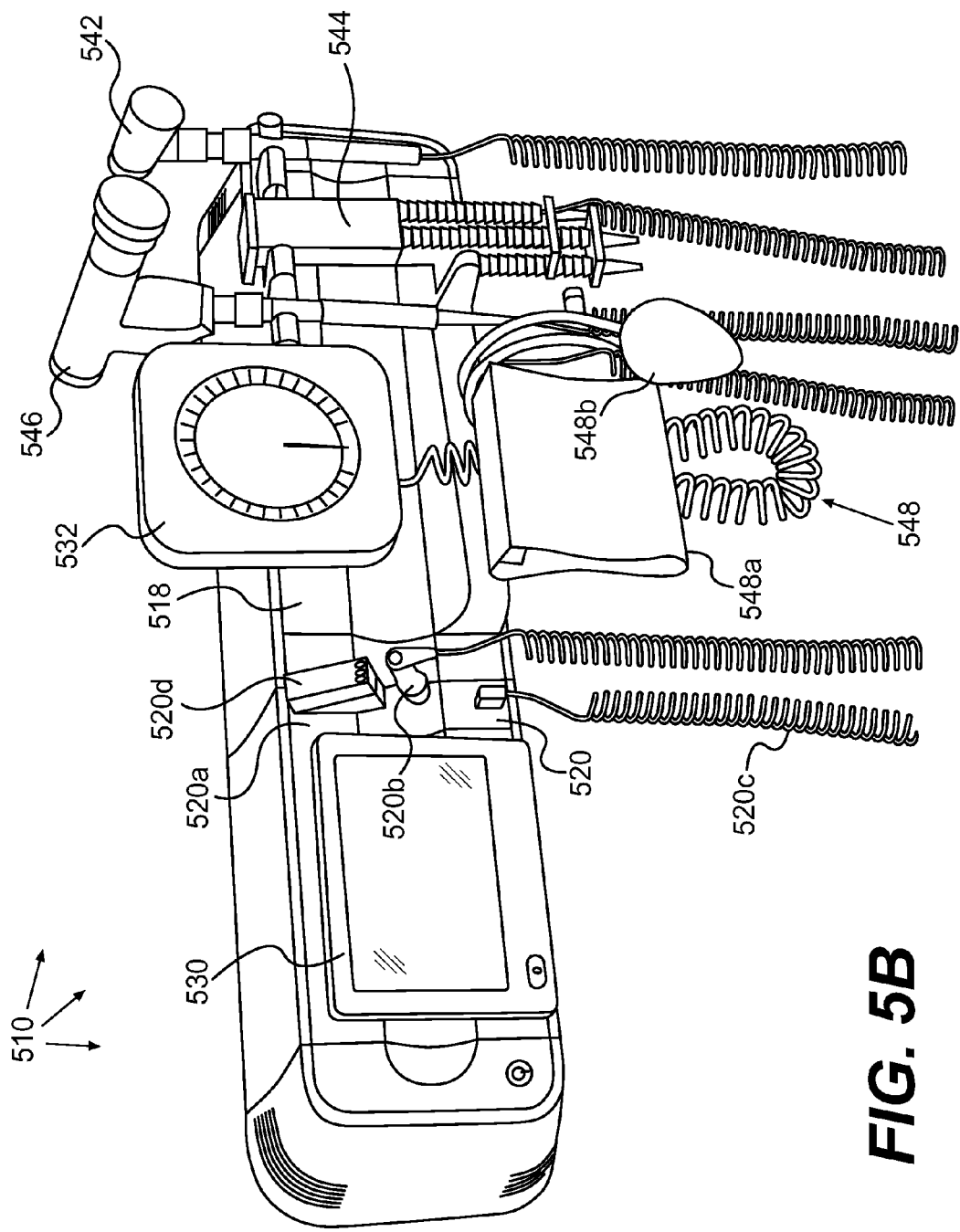

FIG. 5B illustrates a front side perspective view of the embodiment of FIG. 5A including hand accessible components 542-548 disposed within the support structures such as the protrusions 512b-518b (see FIG. 5A). Each support structure 512b-518b is manufactured as a portion of a customized face plate attached to each respective module enclosure 512-518.

As shown, a hand accessible component 542 is an otoscope 542 employed for visual inspection of body cavities, such as an ear or nose cavity of a patient. Hand accessible component 544 is an otoscope tip dispenser 544 designed to store and dispense tips designed to attach onto an otoscope 426. The hand accessible component 546 is an ophthalmoscope 546 employed for visual inspection of the eye, and hand accessible component 548 is a non-invasive blood pressure measuring device 548, which includes a blood pressure cuff 548a, pressure bulb 548b and pressure meter 548c.

As described in FIG. 1A, the temperature measurement module 520 is designed to measure body temperature of a patient and includes a front panel (face plate) 520a, having an outer surface accessible from the front side of the wall mounted configuration apparatus 510. The front panel 112*a* includes access to a well (not shown) storing a removable probe (not shown) attached to a probe handle 520*b* (shown). The probe and its attached probe handle are tethered to the module 520 via an insulated conductor 520*c*. A probe cover dispenser 520*d* is designed to store a collection of disposable probe covers each dimensioned to be disposed over the removable probe.

Figure 5C:
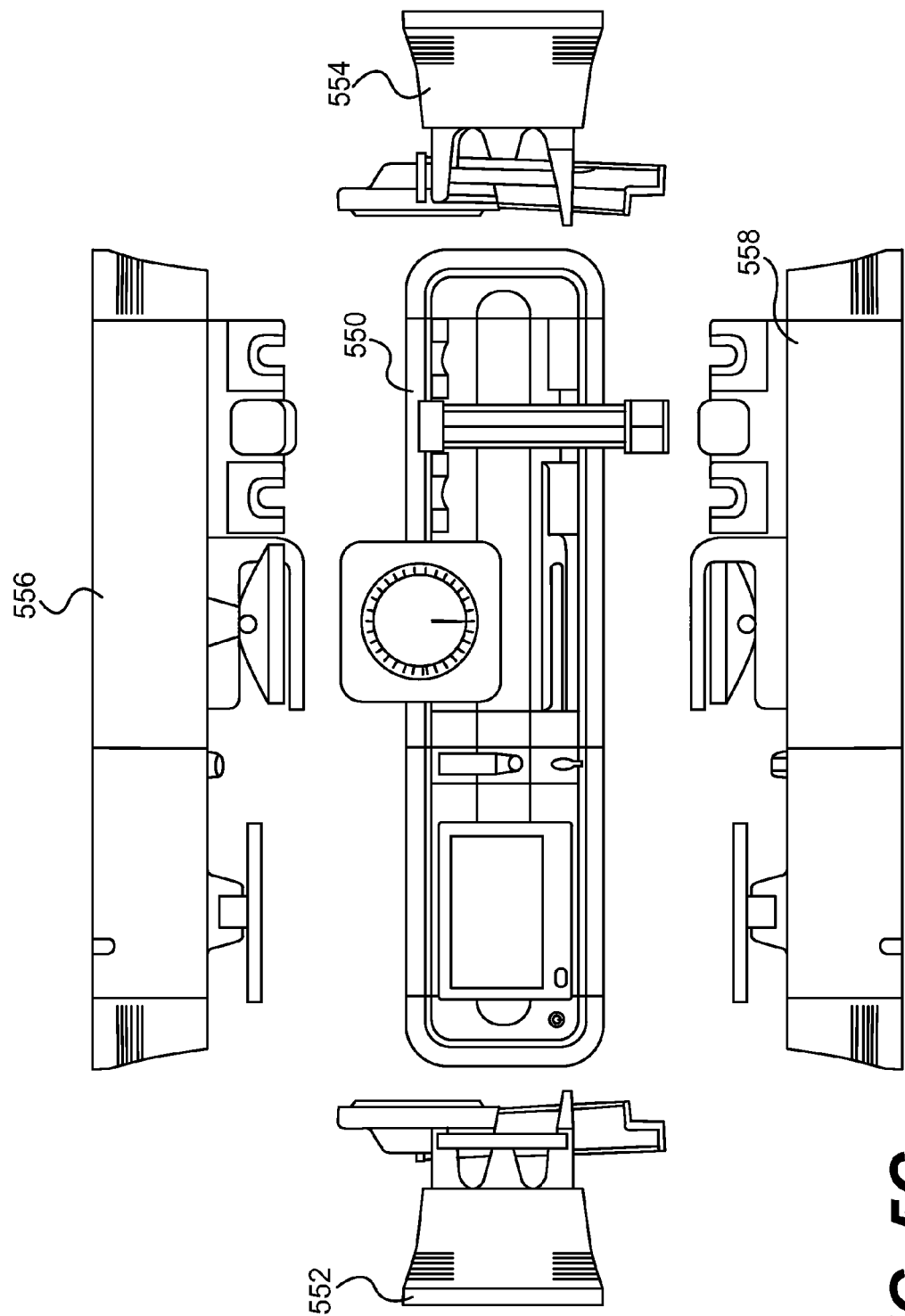

FIG. 5C illustrates a variety of views of the embodiment of the wall mounted configuration 510 of FIGS. 5A-5B. View 550 illustrates the front side of the wall mounted configuration apparatus 510 like that shown in FIG. 5A, while 552 illustrates the left side of the apparatus 510. View 554 illustrates a right side of the apparatus 510, view 556 illustrates an upper side of the apparatus 510, and view 558 illustrates a bottom side of the apparatus 510.

Figure 5D:
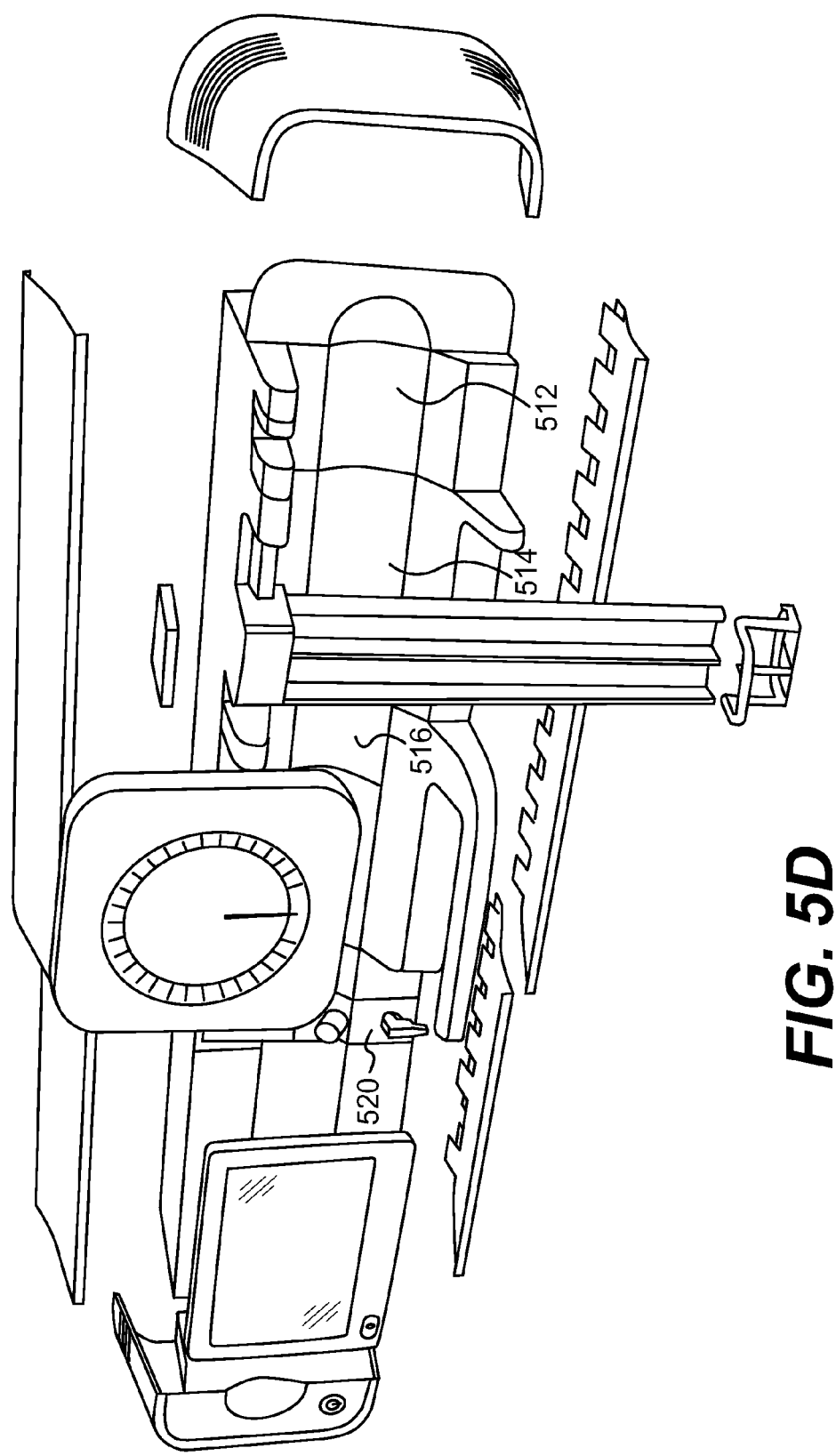

FIG. 5D illustrates a front side exploded view of the wall mounted apparatus 510. A front-side view of each of the module enclosures 512, 514 and 516 is shown. Also, a rear-side view of the printer 432 and its opening 432*a* is also shown.

FIGS. 6A-6H each illustrate embodiments of a socket module structure 610, also referred to herein as a socket module enclosure 210, shown in various states of assembly. A socket module structure 610 is similar to the module structure 210 of FIG. 2A in that it possesses overall exterior dimensions and features that enable it to attach to a frame, such as the frame 260 of FIG. 2E, for example. The socket module 610 differs from the module structure 210 of FIG. 2A by being designed to receive a portable component, also referred to herein as a portable insert, or a plug. The portable insert is designed to be received into an internal cavity within the module structure 610 (see FIG. 6C).

FIG. 6A illustrates a front perspective view of an embodiment of a single slot socket module enclosure 610. As shown, the socket module enclosure 610 is of a generally rectangular shape and includes an open front side lacking a face plate. Like the module enclosure 210, the socket module enclosure 610 includes an upper forward flange 622*a* and a lower forward flange 622*b*. Unlike the module enclosure 210, the upper forward flange 622*a* and the lower forward flange 622*b* do not reside on a face plate, but instead reside on the socket module enclosure 610. A rear side of the socket module enclosure 610 (not shown here) is located opposite to the front side. An upper rear flange 620*a* and a lower rear flange 620*b* are located proximate to and/or along the rear side of the socket module enclosure 610. Unlike the module enclosure 210, the socket module enclosure 610 does not include a recessed portion notched out from the overall shape of the socket module enclosure, such as the recessed portion 218 shown in FIG. 2A.

Figure 6B:
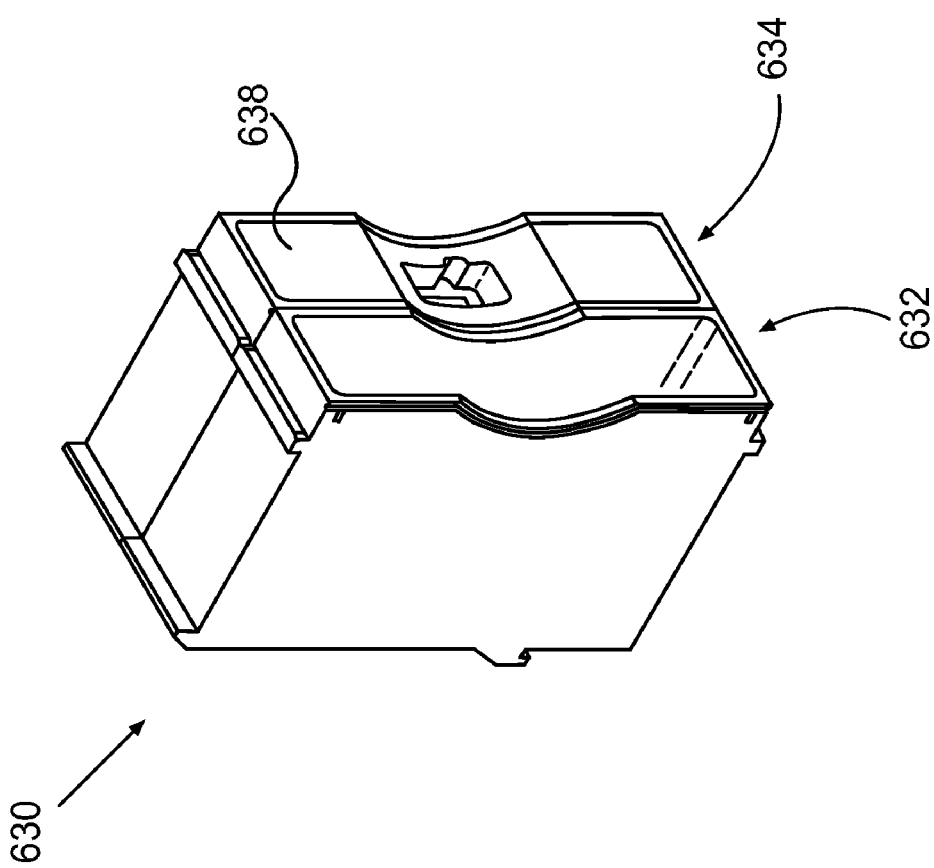

FIG. 6B illustrates a front perspective view of a double slot socket module enclosure 630 including an attached portable insert 638. As shown, a first (left most) slot 632 is shown as being empty (unoccupied) and a second (right most) slot 634 is shown as being occupied and including a portable insert 638 residing within it. As shown, when the portable insert 638 is fully inserted within a slot 634, the portable insert 638 mechanically and electrically attaches to the socket module enclosure 630 via engagement between an electrical connector (not shown) located along the rear interior surface (not shown) of the slot 634 and an electrical connector located along the rear exterior surface (not shown) of the portable insert 638.

Figure 6C:
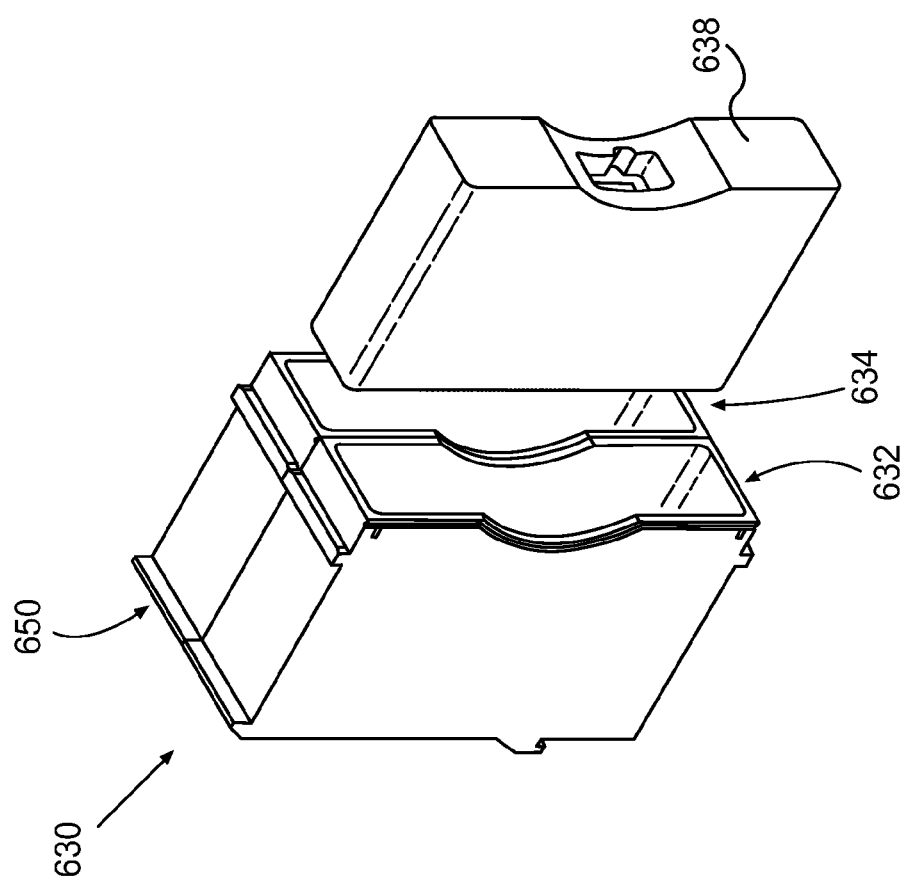

FIG. 6C illustrates a front perspective view of a double slot socket module enclosure 630 and a detached portable insert 638. As shown, a first (left most) slot 632 and second (right most) slot 634 are shown as being empty (unoccupied). As shown, the portable insert 638 is fully withdrawn from the slot 634, and the portable insert 638 is mechanically and electrically detached from the socket module enclosure 630.

Figure 6D:
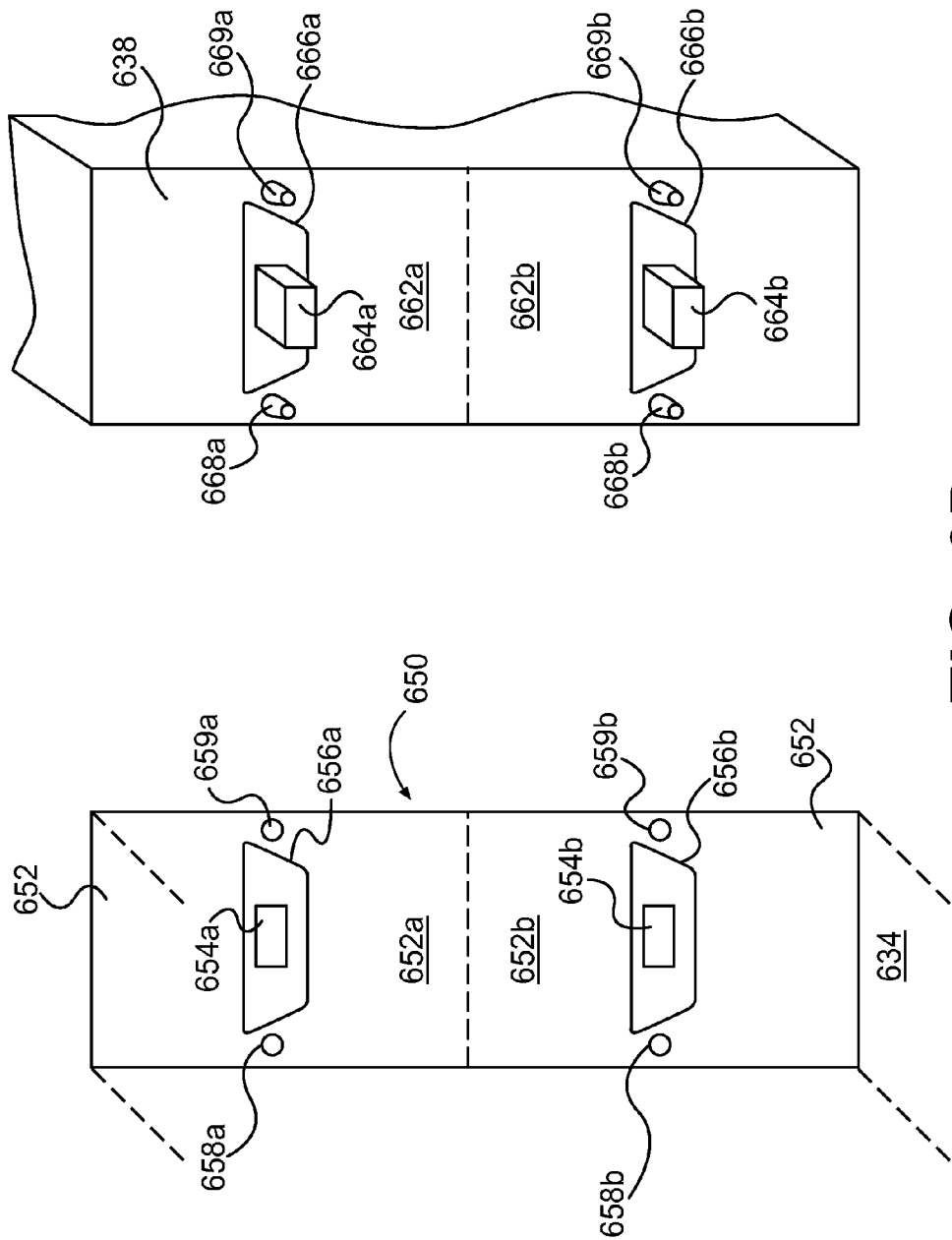

FIG. 6D illustrates a perspective view of a power and data connection between the portable insert 638 and slot 634 of socket module 630. A rear interior surface 652 of slot 634 is divided into an upper section 652*a* and a lower section 652*b*. The upper section 652*a* occupies an upper half and the lower section 652*b* occupies a lower half of rear interior surface 652 of the slot 634. The rear interior surface 652 faces in an opposite direction relative to the rear exterior surface 650 of a rear wall of the slot 634 receiving the portable insert 638.

Each section 652*a*, 652*b* includes a female USB connector 654*a* and 654*b* respectively. The USB connector 652*a* is centered within section 652*a* and the USB connector 652*b* is centered within section 652*b*. Each USB connector 654*a* and 654*b* is surrounded by a perimeter wall 656 having a shape like that of a RS-232 "D connector". Either side of the perimeter wall 656 has a cylindrical cavity 658*a*, 658*b* designed to receive a tapered protrusion associated with a complementary male USB connector.

A rear exterior surface 662 of portable insert 638 is divided into an upper section 662*a* and a lower section 662*b*. The upper section 652*a* occupies an upper half and the lower section 652*b* occupies a lower half of rear exterior surface 662 of the portable insert 638.

Each section 662*a*, 662*b* includes a male USB connector 664*a* and 664*b* respectively. The male USB connector 664*a* is centered within section 662*a* and the male USB connector 664*b* is centered within section 662*b*. Each male USB connector 664*a* and 664*b* is surrounded by a perimeter wall 666*a* and 666*b* respectively, having a shape like that of a RS-232 "D connector". Either side of the perimeter wall 666*a*-666*b* has a tapered protrusion 668*a* and 669*a* in section 662*a* and 668*b*, 669*b* in 662*b* each designed to engage an inner surface of the cavity 659*a* and 658*a* of section 652*a* and 659*b* and 658*b* of section 652*b*, respectively. The cavities 668*a*, 669*a*, 668*b* and 669*b* are also referred to herein as pilot holes. Hence, 668*a* and 669*a* engage 659*a* and 658*a* respectively and 668*b* and 669*b* engage 659*b* and 658*b* respectively.

When the portable insert 638 is fully inserted into slot 634, the male USB connector 664*a* engages female USB connector 654*a* and the male USB connector 664*b* engages female USB connector 654*b*. Accordingly, perimeter wall 666*a* will engage and surround perimeter wall 656*a* and perimeter wall 666*b* will engage and surround perimeter wall 656*b*. Tapered protrusion 668*a* and 669*a* will each engage an inner surface of each of the cavities 659*a* and 658*a* respectively, and tapered protrusion 668*b* and 669*b* will each engage an inner surface of each of the cavities 659*b* and 658*b* respectively, and also referred to as pilot holes 658*a*, 658*b*, 659*a* and 659*b*.

Accuracy of the connection can be supported by tight tolerances between the dimensions of the interior of the slot 634 and the exterior dimension of the portable insert 638. In some embodiments, the tolerances require that the height of the interior of the slot 634 to be equal to or less than 2 millimeters larger than the height of the exterior of the portable insert 638. Likewise, the tolerances require that the width of the interior of the slot 634 to be equal to or less than 2 millimeters wider than the width of the exterior of the portable insert 638.

In some embodiments, a compartment (not shown) between the rear wall 652 of slot 634 and the rear outer surface 650 (rear exterior side of the socket module) (not shown here) can allow for a volume of space to electrically connect each interior female USB connector that receives each male USB connector 664*a*, 664*b* of the portable insert 638, to each of two (2) exterior female USB connectors residing along the rear exterior surface 650 (not shown here) to each receive a male USB connector from a separate USB cable (not shown) from the PACC 210b. For a socket module embodiment, no notch to receive an exterior USB cable is employed, and instead, the shape of the socket module is rectangular. In other embodiments, one exterior female USB connector can be connected to one interior female USB connector where the module is configured to include only one full height portable insert.

Figure 6E:
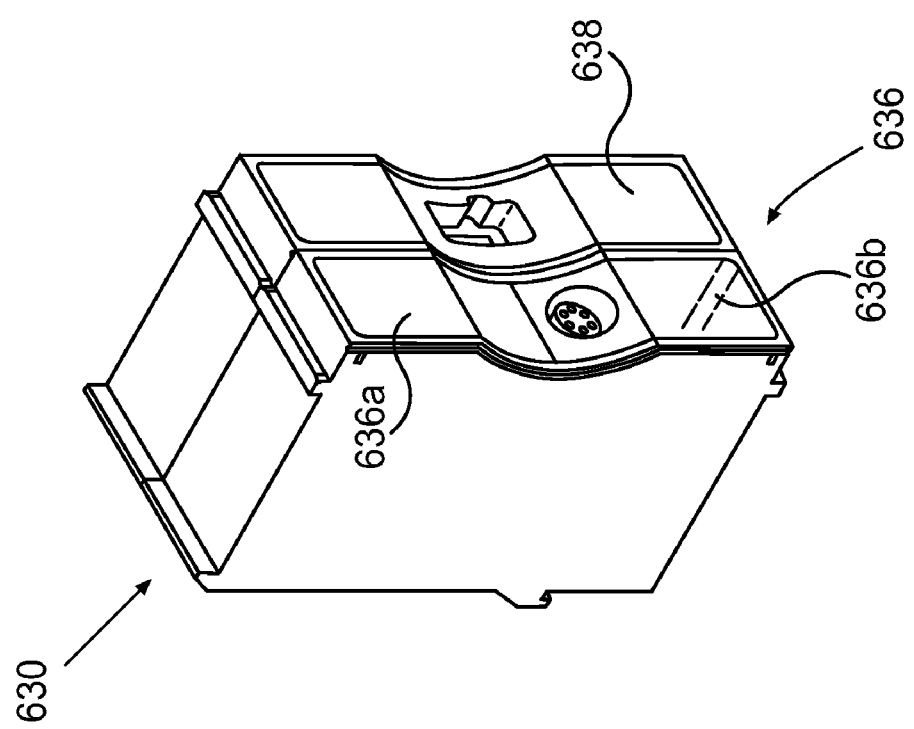

FIG. 6E illustrates a front perspective view of a double slot socket module enclosure 630 that includes attached portable inserts 636 and 638. As shown, when the portable insert 636 and 638 are fully inserted within each respective slot 632 and 634, each insert 636, 638 mechanically and electrically attaches to the socket module enclosure 630 via engagement between an electrical connector (not shown) located along the rear interior surface (see 652 of FIG. 6D) of each respective slot 632, 634 and an electrical connector located along the rear exterior surface (see 662 of FIG, 6D) of each respective portable insert 636, 638.

The portable insert 636 occupies a full slot 632, and the portable insert 636 is actually a combination of two (2) half-height inserts, namely an upper half-portable insert 636a and a lower-half portable insert 636b. Each half-height portable insert 636a, 636b includes a exterior male USB connector along its rear exterior surface as shown in FIG. 4D (see 662a, 662b of FIG. 4D) and designed to engage a female USB connector along a rear interior surface of the slot 632 as shown in FIG. 4D (see 652a, 652b of FIG. 4D).

A half-height portable insert enables functionality to be more densely packed into one (1) slot. As described above, each half-height portable insert has an electrical power and data connection within each slot 632. Hence, each slot 632 provides two (2) electrical power and data connections for one full-height portable insert, or one (1) electrical power and data connection for each of one half-height portable insert.

Figure 6F:
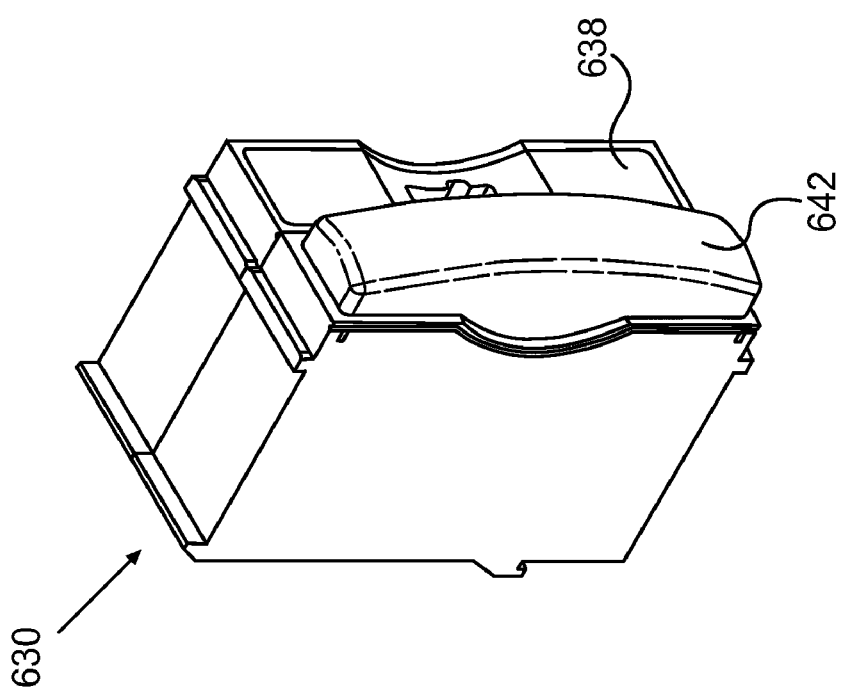

FIG. 6F illustrates a front perspective view of a double-slot socket module enclosure 630 that includes one (1) full-height extended portable insert 642 and the full-height non-extended portable insert 638. As shown, the portable insert 642 is fully inserted within slot 632 and portable insert 638 is fully inserted within slot 634.

The full-height portable insert 642 is designed to extend beyond the front side of the socket module enclosure 630, and is referred to as an extended portable insert 642. An extended portable insert enables more volume to be allocated to a particular portable insert within a slot 632 of fixed size. In some circumstances, more volume may be required to support functionality, such as to perform a particular physiological measurement, that otherwise cannot be provided by an un-extended full height portable insert.

Figure 6G:
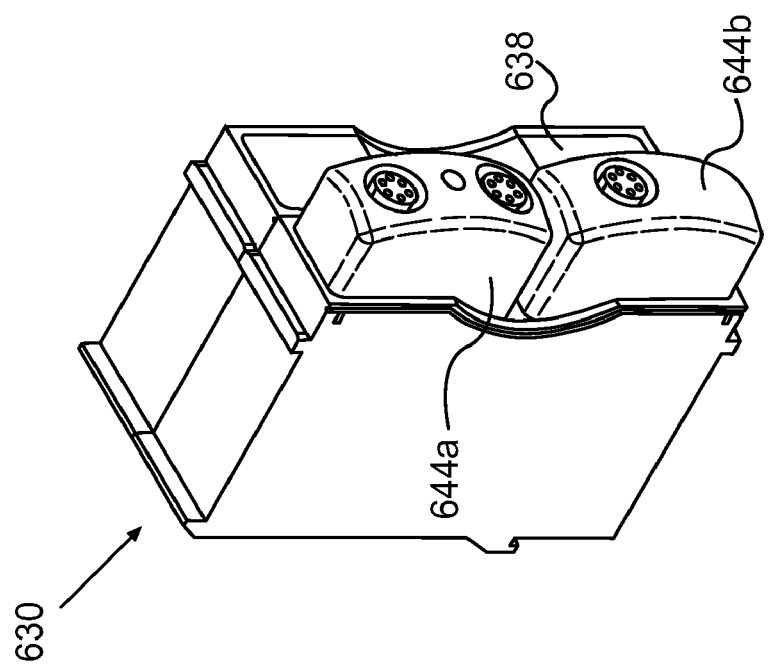

FIG. 6G illustrates a front perspective view of a double-slot socket module enclosure 630 that includes two (2) half-height extended portable inserts 644a, 644b and the full-height non-extended portable insert 638. As shown, the portable inserts 644a and 644b are fully inserted within slot 632 and portable insert 638 is fully inserted within slot 634.

The half-height portable inserts 644a, 644b are designed to extend beyond the front side of the socket module enclosure 630, and are referred to as extended portable inserts 642a and 642b. Extended portable inserts enable more volume to be allocated to a particular portable insert. In some circumstances, more volume may be required to support functionality, such as to perform a particular physiological measurement, that otherwise could not be provided by an unextended half-height portable insert.

Figure 6H:
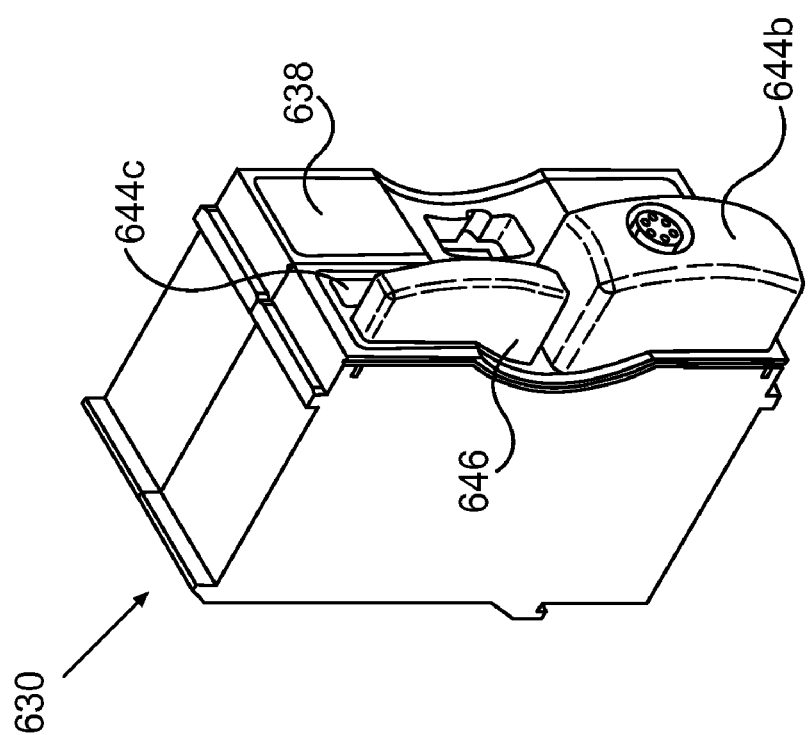

FIG. 6H illustrates a front perspective view of a double-slot socket module enclosure 630 that includes two (2) half height extended portable inserts 644b, 644c and the full height non-extended portable insert 638. As shown, the portable inserts 644b and 644c are fully inserted within slot 632 and portable insert 644 is fully inserted within slot 634.

The half height extended portable insert 642c functions as a socket, like the socket module 630 that it is inserted into, and this insert 642c is designed to receive another type of insertable component 646, which is an edge card type of connector 646. The extended portable insert 642c is also referred to herein as a sub-socket and the insertable component 646 is also referred to herein as a sub-insert.

FIGS. 7A-7F illustrate views of an integrated bed-mounted module apparatus configuration 710. This type of apparatus configuration is just one example of how health-care equipment (HCE) modules, whether of a non-socket or socket type, can be integrated into other objects, such as furniture, that exist within a health care facility. Some of these objects, such as a portable (rolling) bed apparatus, are portable and can travel with a health care facility patient. Hence, any physiological parameter monitoring function provided by HCE modules embedded in such objects can accompany and/or travel with a health care patient within the health care facility.

FIG. 7A illustrates a hand-held frame apparatus 720 integrated within and attached to a head board 718 portion of a bed apparatus. This configuration 710 includes a plurality of two (2) health-care equipment (HCE) modules 722-724 integrated into a hand held frame apparatus 720 integrated into bed headboard 718. Each HCE module 722-724 is configured to provide specialized support for the provision of health care, including the measurement of physiological parameters.

As shown, the modules 722-724 are integrated into a hand held frame apparatus 720, also referred to herein as a holding unit 720, that has an attached handle 726. The modules 722-724, the frame apparatus 720 and the handle 726 are designed to be attached to each other as one unit and to be attached to or removed from the head board 718 as one unit. Upon removal from the head board 718 the frame apparatus 720 is designed to be held in one hand via the handle 726 of the frame 720.

The particular head board 718 shown is manufactured by the Hill-Rom Corporation of Batesville, Ind. The head board 718 is generally planar in shape, and has been modified (adapted) to receive the hand held frame 720 at a lower portion (corner) of a left hand side vertical edge of the bed head board 718, as shown in this figure. Notice that the head board is shown from a viewing perspective of its outside surface in FIGS. 7A-7C, and shown from a viewing perspective of its inside surface in FIGS. 7E-7F.

Figure 7B:
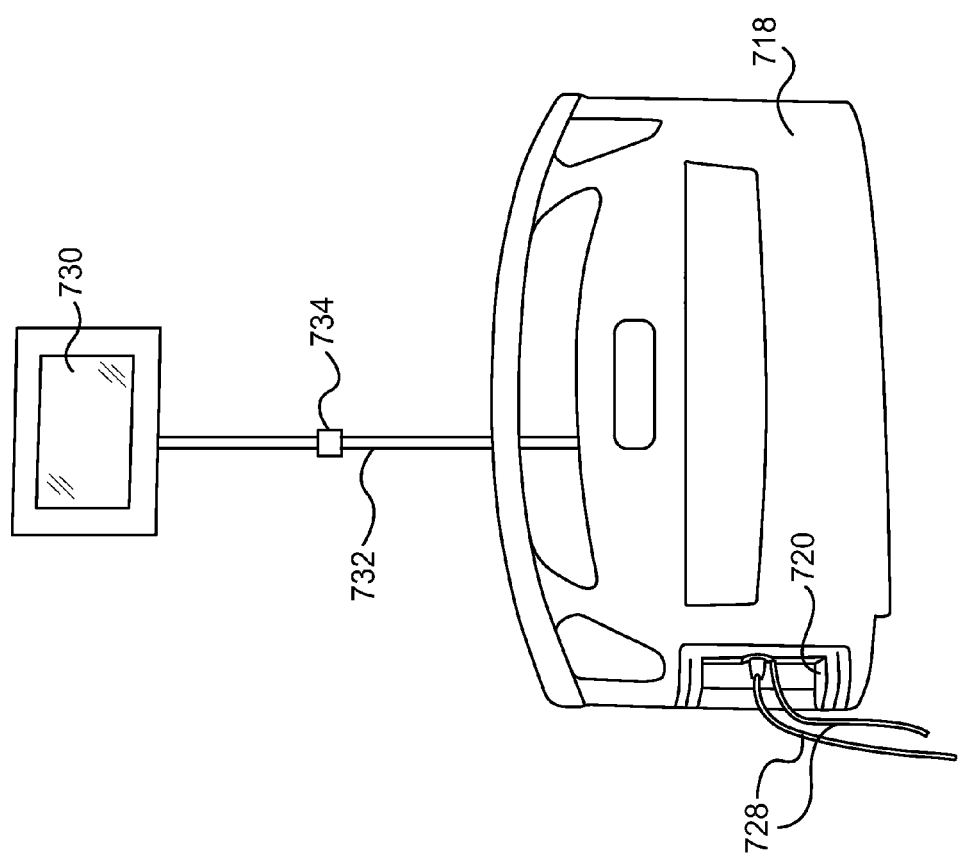
Figure 7D:
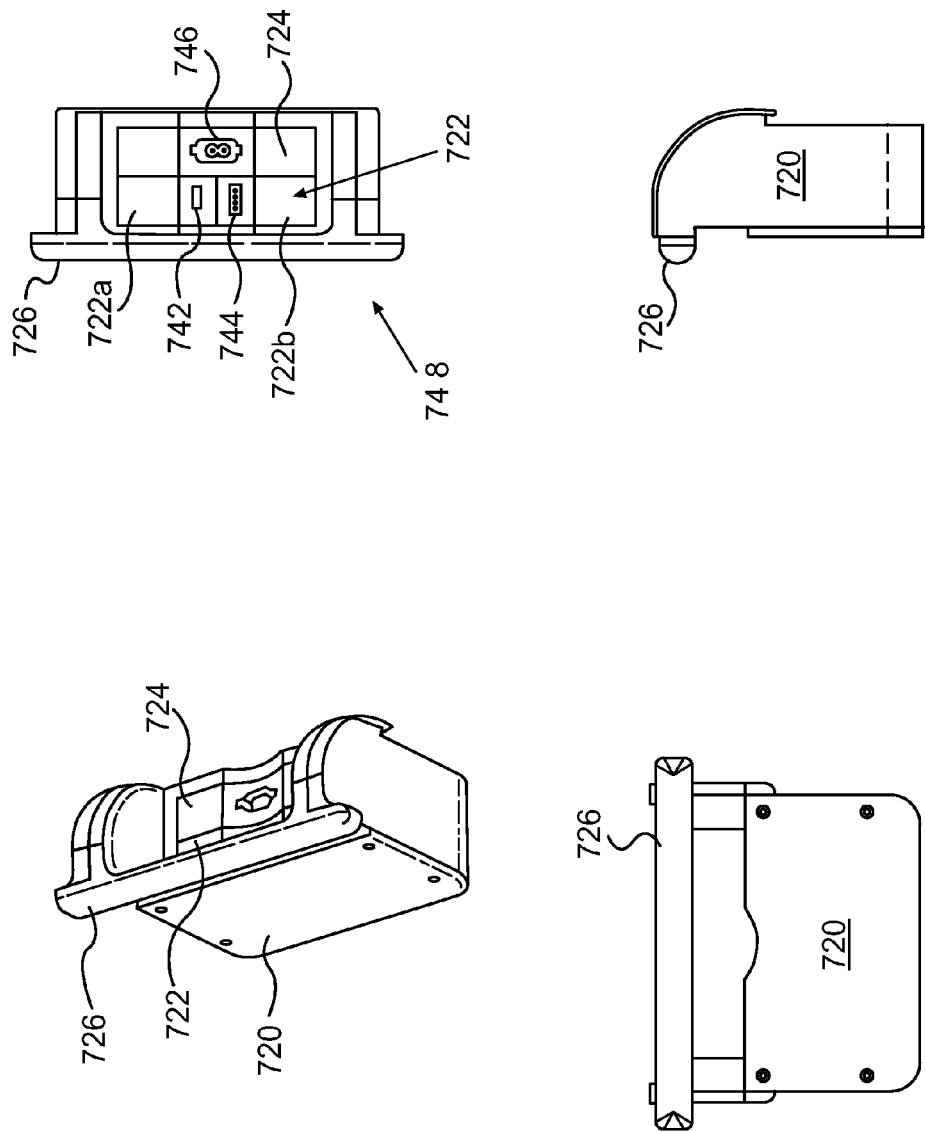
Figure 7E:
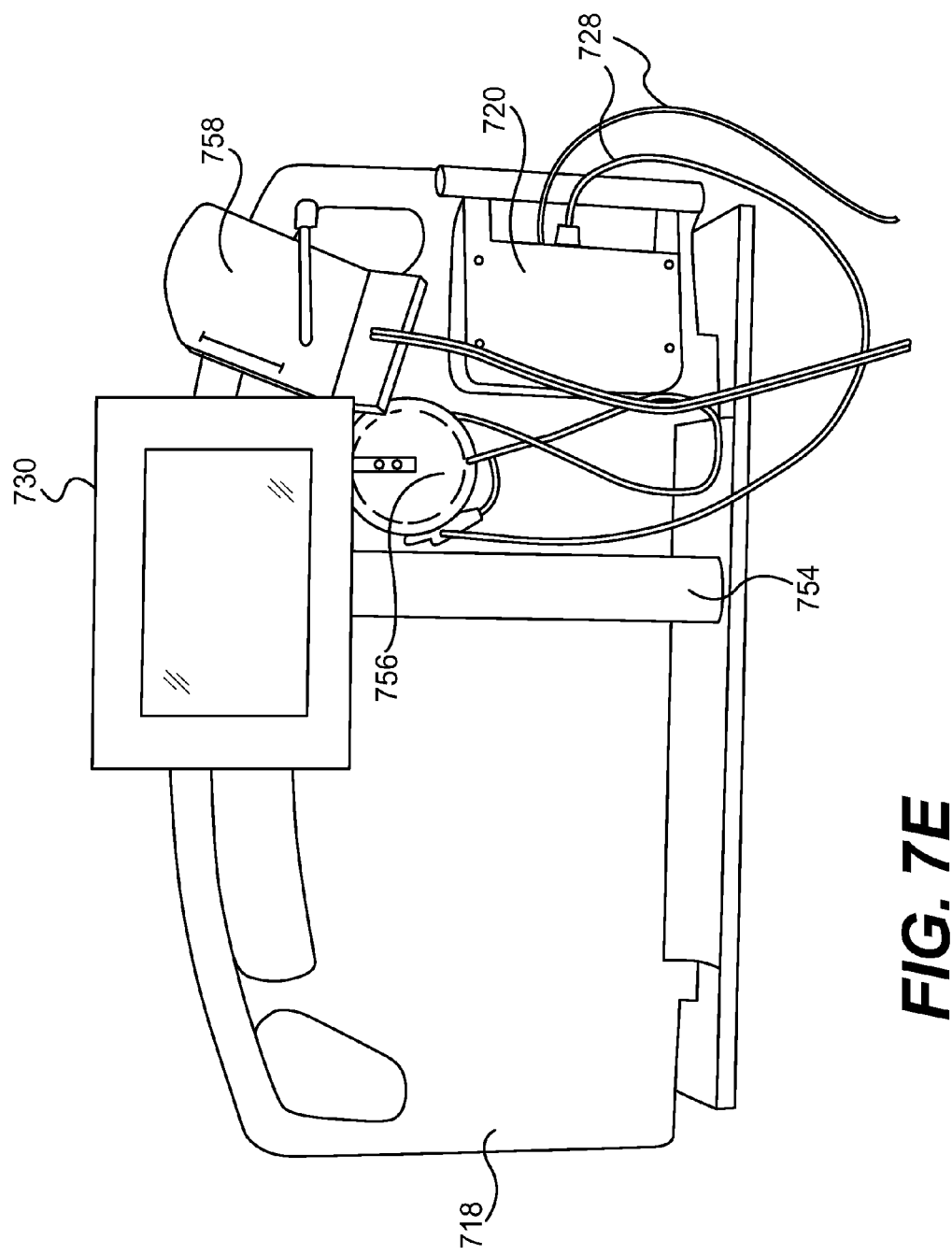
Figure 7F:
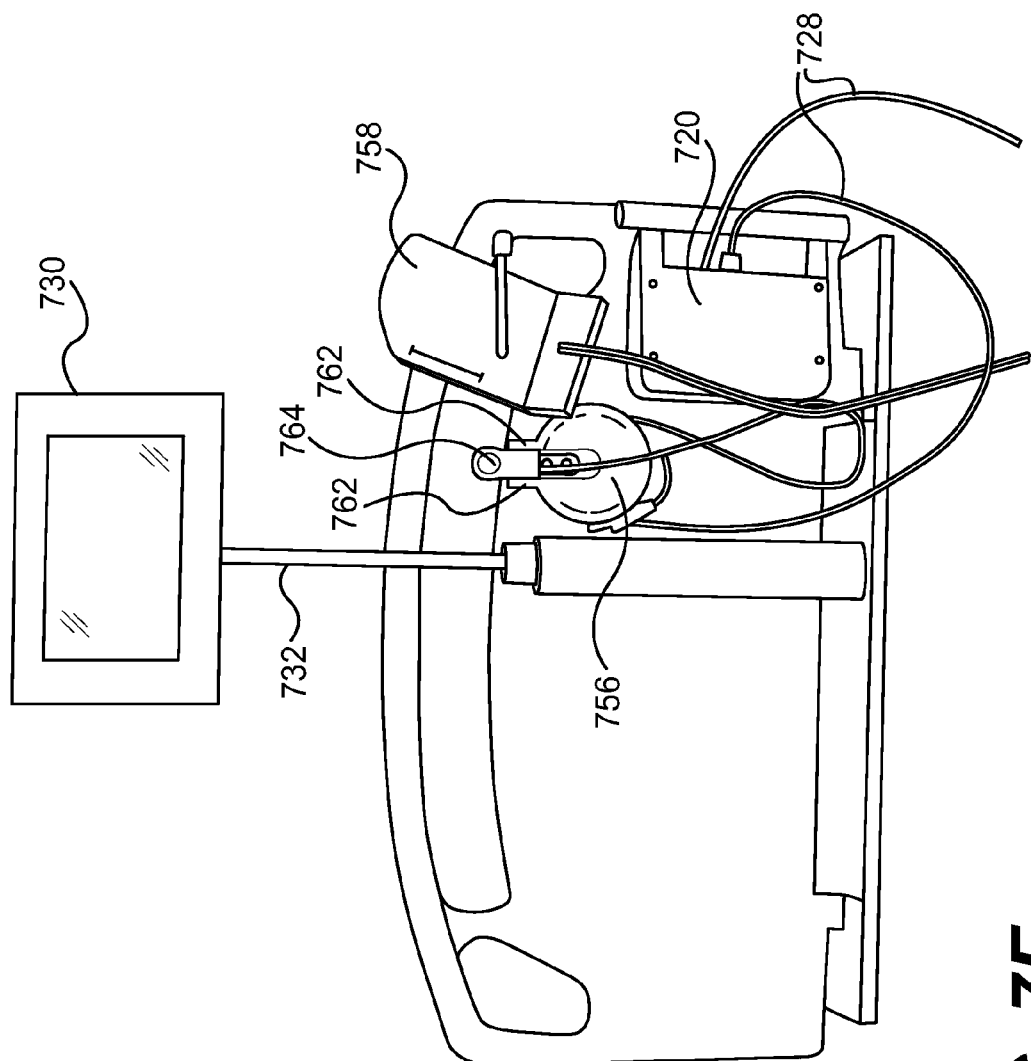

FIG. 7B illustrates the hand held frame apparatus 720 attached to the bed apparatus 718 and further attached via cables 728 to other peripheral components (Shown in FIGS. 7E and 7F). This figure also shows a user interface monitor 730 disposed above the bed apparatus 718 via a support pole 732.

The support pole 732 has a telescopic structure that includes multiple pole segments that each have a different inner diameter that enable two (2) adjacent pole segments to overlap and slide relative to each other. The length of the support pole 732 can fixed and secured via a pole clamp 734 located at an intersection between to adjacent pole segments.

FIG. 7C illustrates a hand-held frame apparatus 720 of FIG. 7B detached from the bed apparatus 718 and suspended in the air while being held in one hand. The hand-held frame apparatus 720 is configured to be detached from a first bed including the headboard 718 and attached (transferred) to another second bed (not shown) including the headboard, in circumstances for example, when transferring a patient from the first bed to the second bed. While transferring the apparatus 720 between different beds, the peripheral components (not shown) may be detached from the apparatus 720 to allow for more freedom of movement of the apparatus 720 during the transfer of the apparatus 720 between the different beds.

FIG. 7D illustrates an isolated view of the apparatus 720. The viewing perspective 728 provides a close and front view of the HCE modules 722 and 724 that reside within the apparatus 720. As shown, upon close inspection of the module 722 which occupies a full slot of the apparatus 720, the module 722 is actually a grouping of two (2) half height modules 722*a* and 722*b*.

The half-height module 722*a* is an electrocardiogram (EKG) module that includes a female USB connector 742. The USB connector 742 is configured to receive a USB cable having a male USB connector (not shown) attached to an electrocardiogram (EKG) peripheral component, referred to as a "puck" (not shown). The puck is attached to a plurality of wires and electrode contacts designed to be attached to a patient being monitored under the control of the electrocardiogram module 722*a*.

The half-height module 722*b* is an SPO2 module that includes a female serial (9-pin) connector 744. The connector 744 is configured to receive a serial cable having a male (9-pin) serial connector (not shown) attached to an SPO2 measuring peripheral component, referred to as an SPO2 "clip" (not shown). The SPO2 clip is attached to a patient being monitored under the control of the SPO2 module 722*b*.

The full-height module 724 is a blood pressure measurement module that includes a pneumatic hose connector 746 to a blood pressure cuff (see FIGS. 7E-7F). The connector 744 is configured to receive at least one pneumatic hose (not shown here) (see FIGS. 7E-7F) attached to the blood pressure cuff. The blood pressure cuff is attached to a patient being monitored under the control of the SPO2 module 722*b*.

Other views within this figure show the hand held frame apparatus from various viewing perspectives. In this embodiment, the apparatus 720 includes a battery so that it is self powered. In other embodiments, the apparatus is configured to receive power provided from the bed apparatus. In yet other embodiments, the apparatus is configured as a portable insert to that it can be inserted into a bed apparatus adapted to provide a socket slot, as described in FIGS. 6A-6H.

FIG. 7E illustrates a view of an inside surface of the bed head board 718 attached to the hand held frame apparatus 720 and attached to the user interface monitor 730 disposed above the bed apparatus 718. A support tube 754 is configured to surround and support the support pole 732 which is not visible in the figure (see FIG. 7F). A cable spool 756 and a blood pressure cuff 758 are also attached to the inside surface of the bed head-board 718. The blood pressure cuff 738 is attached via a pneumatic cable 728 attached to the module 724 which is located within the hand-held frame 720.

FIG. 7F illustrates a view of an inside surface of the bed head-board 718 attached to the hand-held frame 720 and attached to the user interface display monitor 730 disposed higher above the bed apparatus 718. A support tube 754 is configured to surround and support the support pole 732 which is shown as being extended higher above the bed head board 718 than shown in FIG. 7E.

The support pole 732 is constructed like a common telescopic tripod support pole where it expands and contracts in a telescoping like fashion. Expansion and contraction of the support pole 732 is arrested via one or more friction clamps 734 located at different locations along the pole 732 (see FIG. 7B).

The cable spool 756 is designed to store cable not immediately required to be in use. As shown, the cable spool 756 is being employed to store cable attached to the SPO2 measurement module 722*b* of the hand held frame apparatus 720. The cable spool 756 includes at least one protrusion 762 designed to engage the SPO2 clip 764 when it is not in use.

As shown in the aforementioned FIGS. 7A-7F, a healthcare equipment module adapted to be integrated into the structure of a bed (bed frame) while the module is configured to perform measurement of a physiological parameter. The bed is adapted to incorporate the module within an existing volume of space occupied by the bed and without substantially protruding from the volume of space occupied by the bed before the bed is adapted to incorporate the module. The module is removably attachable from the bed and carriable via employment of one hand.

The bed frame can be further adapted to incorporate an electronic display device and a supporting pole for the device. Optionally, the pole is configured to have a telescoping structure for adjustable expansion and contraction of the pole in order to adjust a position of the display device. The bed frame can be adapted to incorporate a cable management device to store excess cable that not in use at a particular time. One or more cables can be each connected a module incorporated into the bed frame.

The hand-held frame apparatus 720 can be integrated into other objects, such as desks, chairs, tables, and sofas employed to provide support for health care patients. The invention is not intended to be limited by the specific embodiments described herein and can be applied in may foreseeable variants that provide benefits to the health care industry.

FIGS. 8A-8E illustrate views of a pole mounted and bed frame attached module apparatus configuration 810. The pole mounted apparatus configuration 810 includes a combination of the mobile frame configuration (MF) 110 of FIGS. 1A-1F and a pole 812 attached to a bottom side of the MF 110. The pole 812 is also attached to a portion of a bed frame 816 via attachment 814. Like the embodiment shown in FIGS. 7A-7F, this embodiment enables health care monitoring equipment to accompany and/or travel with a health care patient within the health care facility, while the patient is lying on or proximate to the bed frame 816.

Figure 8A:
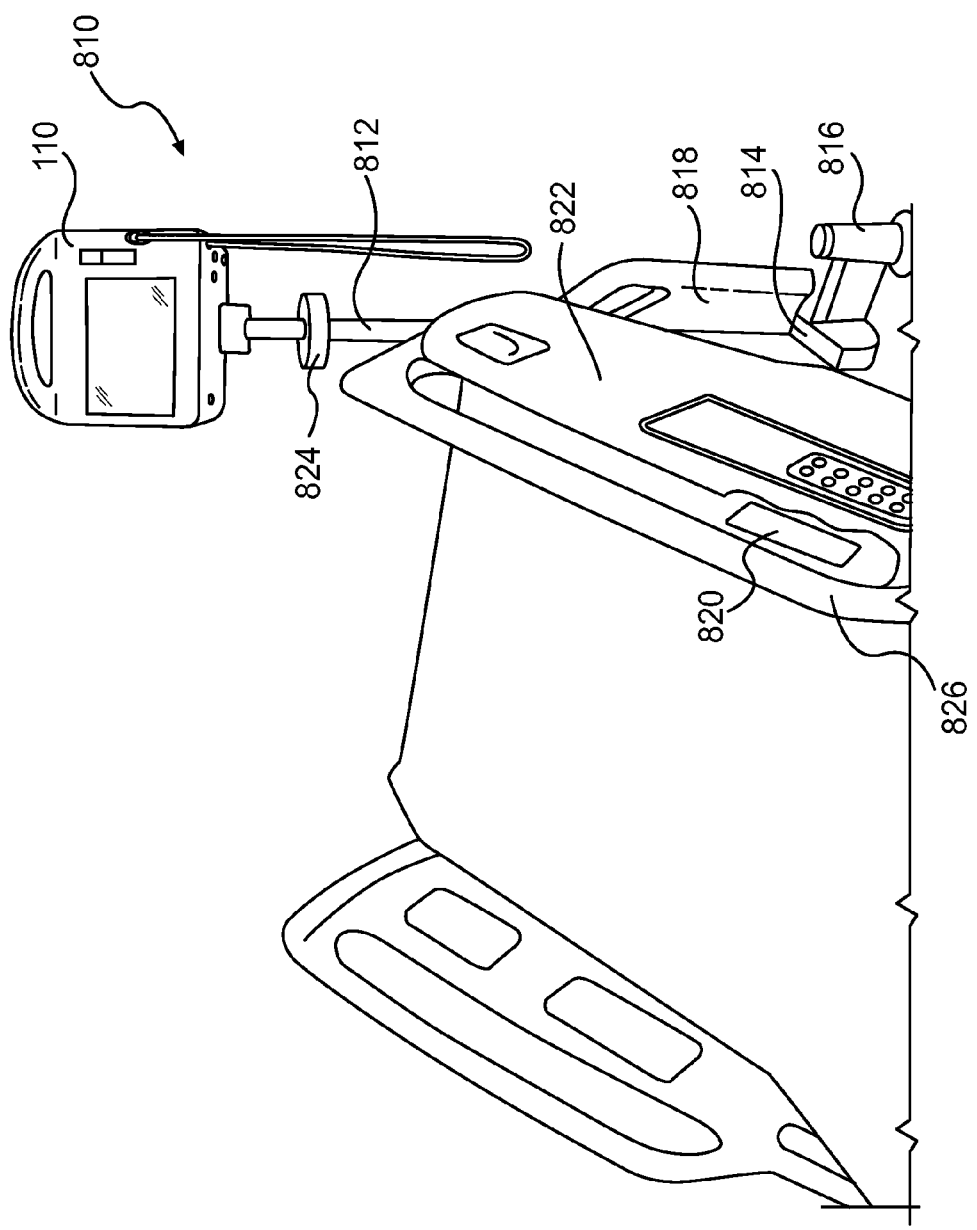

FIG. 8A illustrates the apparatus configuration 810 as it is attached to a bed frame 816 via an attachment 814 located proximate to a corner of the head board 818 of the bed frame 816. The pole 812 is positioned and dimensioned so that an adjustable portion 822 of the bed frame 816 can be adjusted (tilted) within a range of angles without being obstructed by the apparatus 810. The pole 812 includes a pole adjustment handle 824 that enables the pole and the attached MF portion 110 of the apparatus 810 to be rotated along a vertical axis (not shown) parallel to a long dimension of the pole 812.

A side rail attached module apparatus 820 is shown as being disposed within an opening of a side rail 826 of the bed frame 816. As shown, the apparatus 820 is friction fitted within the opening of the side rail 826. In other embodiments, clamps or straps can be employed to rigidly attach the apparatus 820 to the side rail 826.

The side-rail attached apparatus 820 is configured to function in the same manner as the hand-held bed frame apparatus 720 (see FIGS. 7A-7F). The side rail apparatus 820 is configured to include two (2) modules. Optionally one or both of these modules are socket modules (not shown) each configured to receive at least one portable insert.

As shown here, the side-rail apparatus 820 is a plastic prototype markup having the dimensions of another prototype (see side rail apparatus 910 of FIG. 9A) configured to include one or more actual HCE modules. Employment of the side-rail apparatus 820, as opposed to employment of the head board embedded apparatus 720 for a particular be frame, enables removal of the head board 818 without disconnecting or moving cables, in order to slide a patient from the bed apparatus 816 along the side of the bed frame 816 having a removable head board 818.

In some embodiments, the side rail apparatus 820 and the MF 110 of the pole supported apparatus 810 each include an external power and data connector (not shown), such as a USB connector, and are connected via a USB cable (not shown) to enable the side-rail apparatus 820 to receive electrical power from the pole supported apparatus 810 via the USB cable.

FIG. 8B illustrates the apparatus configuration 810 while the adjustable portion 822 of the bed frame 816 is adjusted (tilted) to an angle substantially parallel to the floor upon which the bed frame 816 is supported. The bed frame 816 shown is adjustable between about a zero degree angle (parallel to the floor) (shown here) and to an upright angle within proximity of a 90 degree angle (not shown).

Figure 8E:
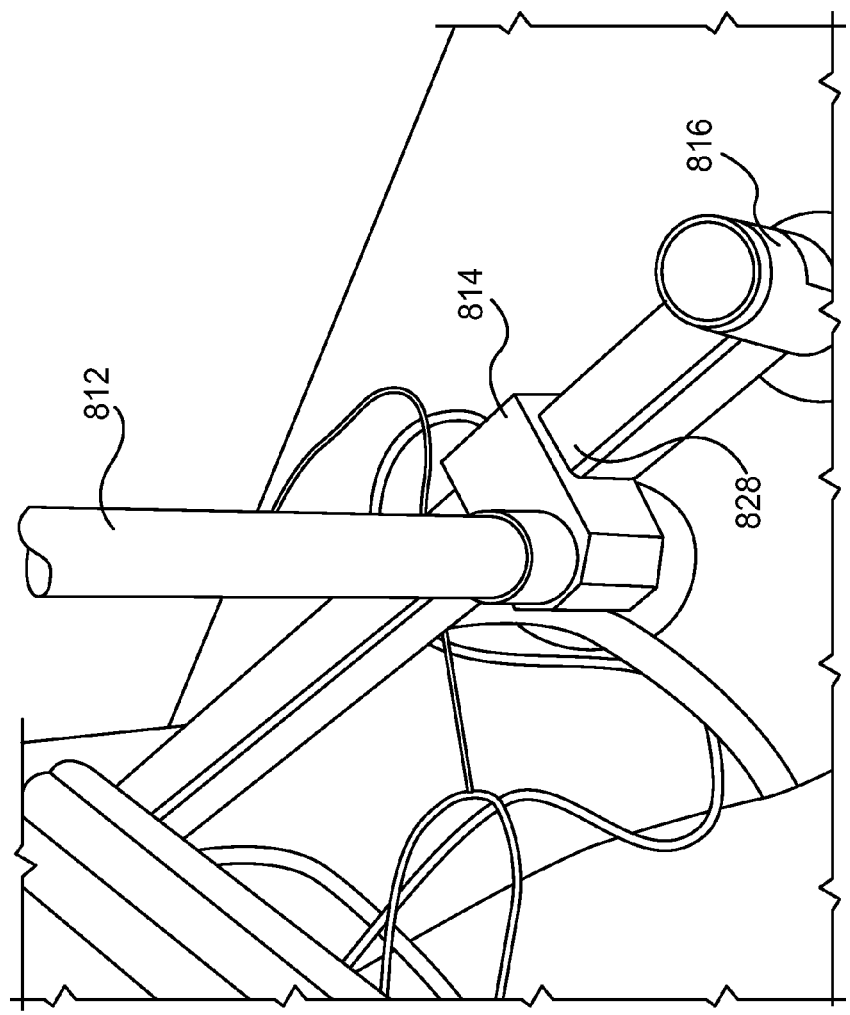

FIGS. 8C-8E each illustrate a closer view of the attachment 814 between the pole 812 and the bed frame 816. FIGS. 8C-8D illustrate the attachment 814 to the bed frame 816 while the head board 818 is also attached to the bed frame 816. FIG. 8E illustrates the attachment 814 to the bed frame 816 while the head board 818 is not attached to the bed frame 816.

As shown, the attachment 814 is a clamping mechanism that substantially surrounds and friction fitted around a horizontal bar 828 of the bed frame 816 (see FIG. 8E). The horizontal bar 828 has a rectangular cross-section (not shown) substantially surrounded by the attachment clamp 814. A wing-nut screw mechanism (not shown) can further employed to turn into a threaded hole within the clamp 814 and to press against the horizontal bar 828 to created a tighter grip between the clamp 814 and the bar 828.

The pole mounted and bed frame attached apparatus 810 does not substantially protrude from a horizontal cross section of the bed frame 816 parallel to the floor (surface of the earth). In other words, the apparatus 810 protrudes vertically above the bed apparatus but does not substantially protrude horizontally away from the bed to substantially maintain a "foot print" of the bed apparatus within a health care facility. Likewise, the hand held side rail attached apparatus 820 does not substantially protrude outside of a horizontal cross section of the bed frame 816 and further, does not protrude vertically above the existing bed frame 816.

As described above, the (HCE) modules are attached to and interoperate with a frame configured to be a desktop configuration, a wall-mounted configuration, a mobile configuration or a hand-carriable configuration. Each of the configurations is operable without requiring modification to any of the mechanical interface, the electrical interface or the software interface between a module and a frame to which the module is attached.

FIGS. 9A-9E illustrate views of a side rail attached module apparatus 910. A side rail attached module apparatus 910 is shown as being disposed within an opening of a side rail 826 of the bed frame 816. As shown, the apparatus 910 is attached to the side rail 826 via a plate and two (2) screws (see FIG. 9E). In other embodiments, the apparatus is friction fitted within the opening of the side rail 826. In other embodiments, clamps or straps can be employed to rigidly attach the apparatus 820 to the side rail 826.

The side rail attached apparatus 910 is configured be hand held when unattached to the side rail 826 and is configured to function in the same manner as the hand held bed frame apparatus 720 (see FIGS. 7A-7F). As shown, the side rail apparatus 910 is configured to include one (1) module. Optionally and as shown, this module is a socket module configured to receive at least one portable insert 912.

Employment of the side rail apparatus 910, as opposed to employment of the head board embedded apparatus 720 for a particular bed frame, enables removal of the head board 818 without disconnecting or moving cables, in order to slide a patient from the bed apparatus 816 along the side of the bed frame 816 having a removable head board 818.

In some embodiments, the side rail apparatus 910 and the MF 110 of the pole supported apparatus 810 each include an external power and data connector (not shown), such as a USB connector, and are connected via a USB cable (not shown) to enable the side rail apparatus 910 to receive electrical power from the pole supported apparatus 810 via the USB cable.

Figure 9B:
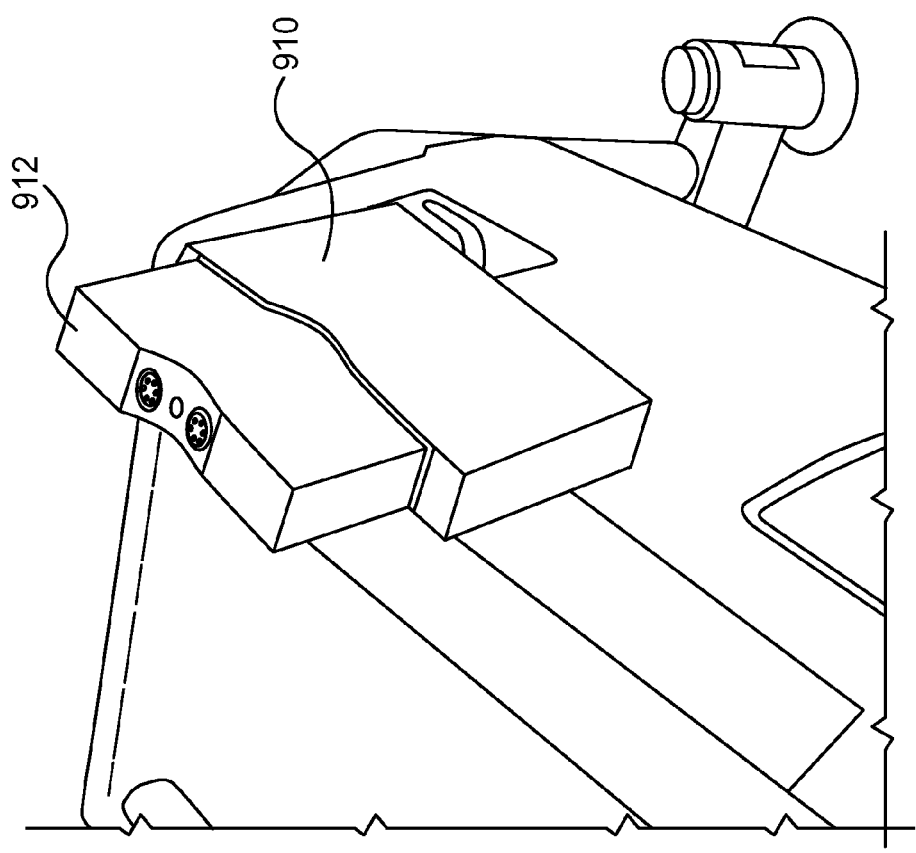
Figure 9C:
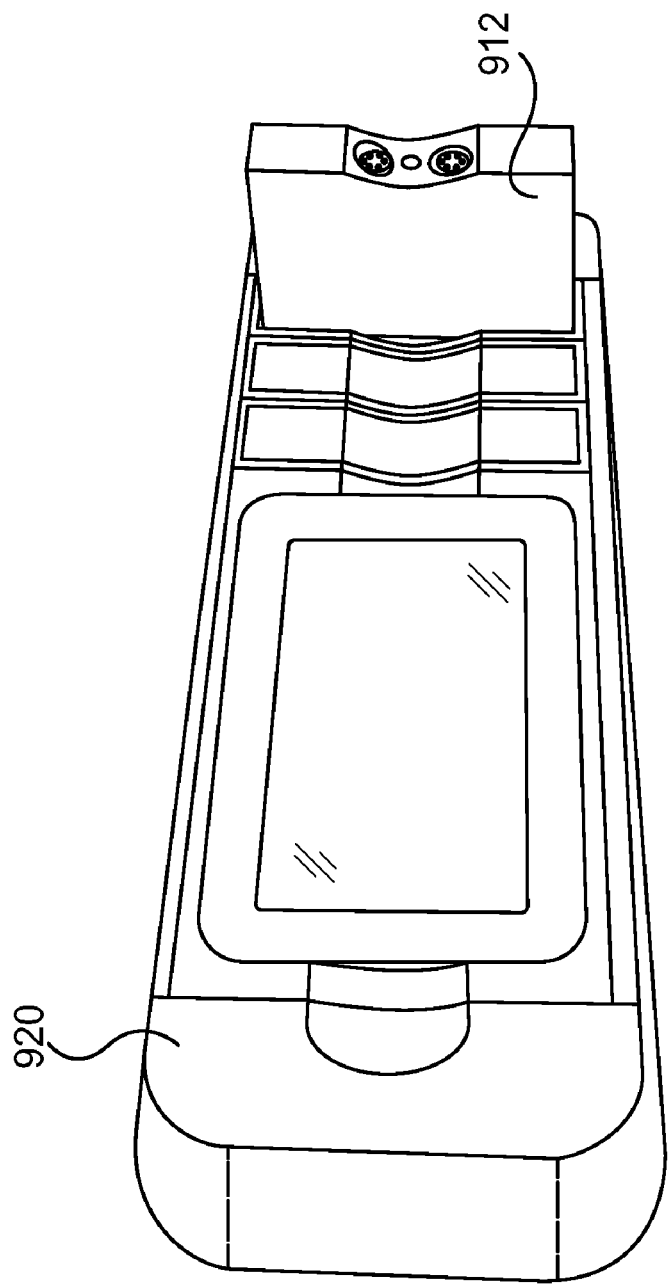
Figure 9D:
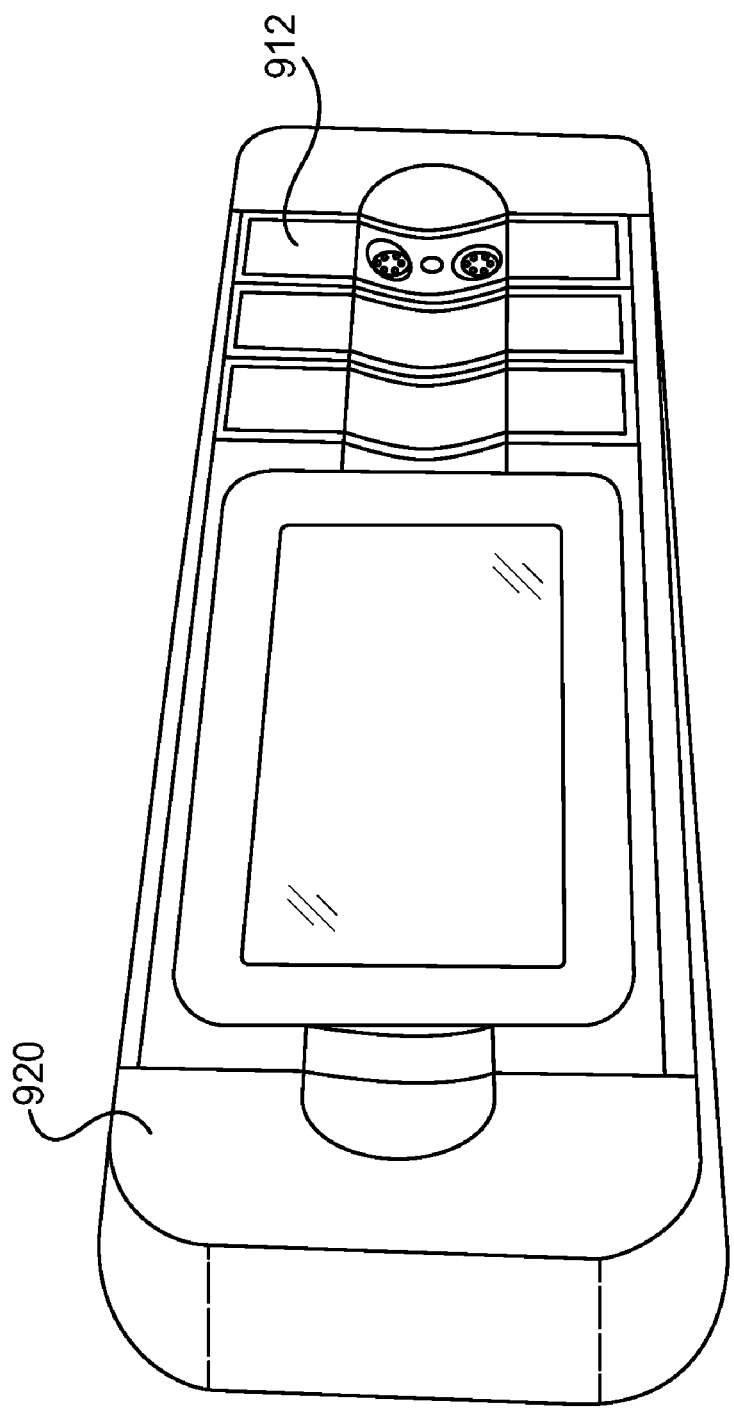

FIG. 9B illustrates the portable insert 912 being removed from the side rail apparatus 910. FIG. 9C illustrates the portable insert 912 as being partially inserted into a wall apparatus 920. The wall apparatus 920 is a different configuration as compared to the wall apparatus 510 of FIGS. 5A-5D. FIG. 9D illustrates the portable insert 912 being fully inserted into the wall apparatus 920.

Figure 9E:
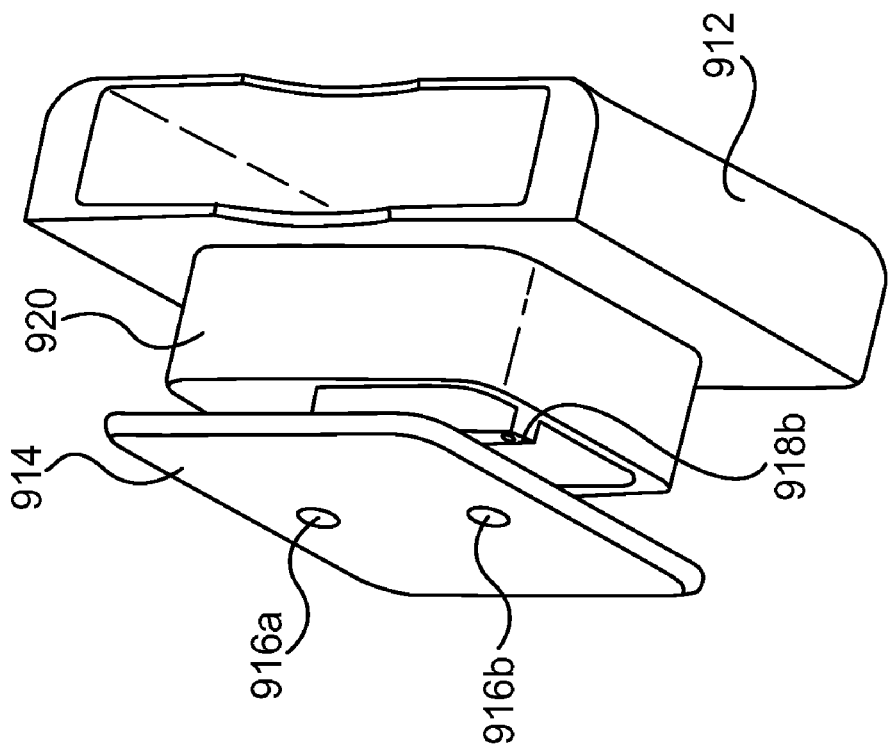

FIG. 9E illustrates a bed bracket 920 for physically attaching the side rail apparatus 910 to the side rail 826 of the bed frame 816 (see FIG. 9A). As shown, the bracket 920 includes screw holes 918*a* (not shown) and 918*b* (shown) that receive two (2) screws (not shown) passed through holes 916*a*-916*b* of a plate 914. When attached to the side rail 826 (not shown), the side rail 826 is disposed between the plate 914 and the bracket 920 so that the side rail 826 is "sandwiched" and pressed between the plate and the bracket 920 when the two (2) screws are tightened.

Hence, health care information gathered from the side rail apparatus 910 via the portable insert 912 can be transferred to other module configurations, such as the wall mounted module apparatus 920.

Figure 10A:
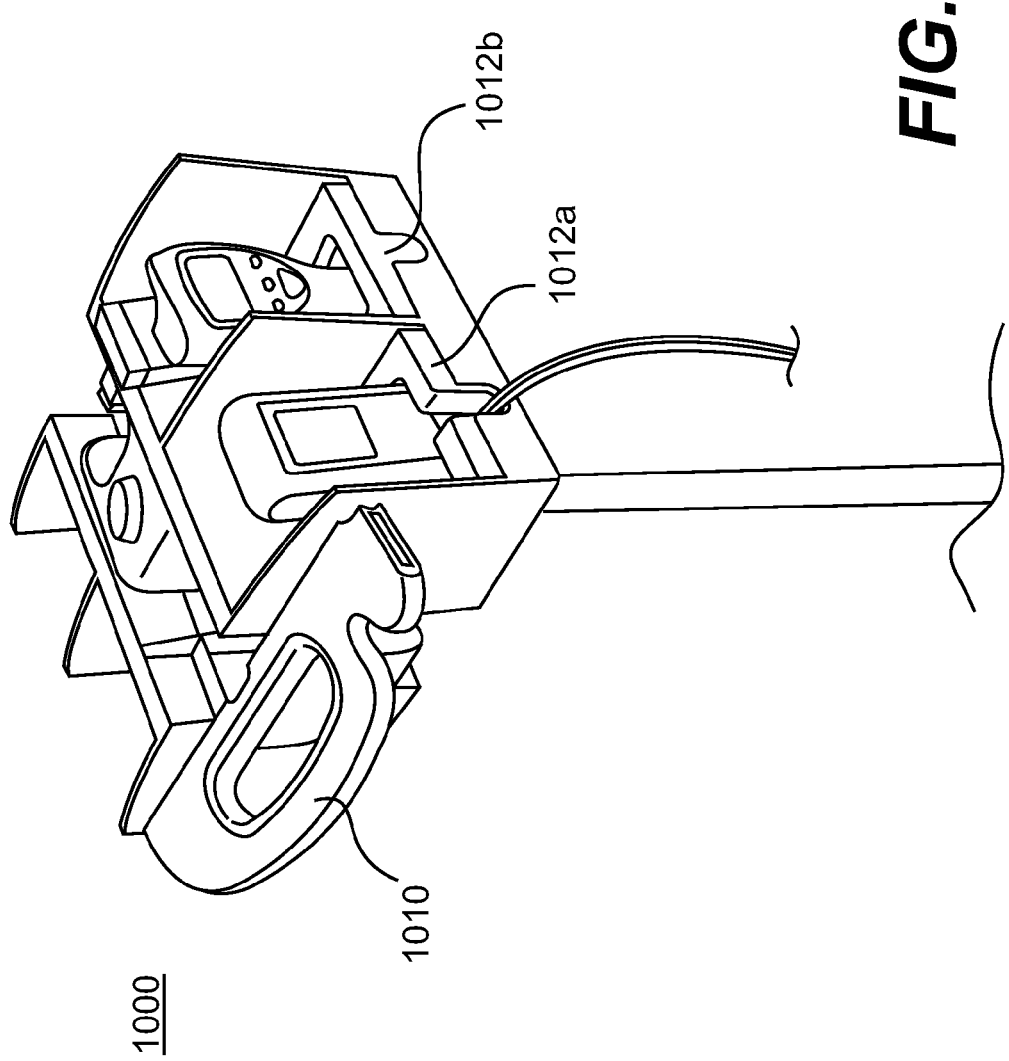
FIGS. 10A-10D illustrate views of a variety of alternative embodiments of frame supporting structures, health-care equipment modules and peripheral components.

FIGS. 10A-10F illustrate views of a variety of alternative embodiments of frame supporting structures, health-care equipment modules and peripheral components. FIG. 10A illustrates a mobile wheel mounted cart 1010 configuration 1010 that provides mechanical, electrical and software interface support for hand held sensor devices each stored (docked) within a well 1012*a*-1012*b*. Each well 1012*a*-1012*b* is implemented as a module enclosure that has a mechanical and electrical interface with the cart 1010.

Figure 10B:
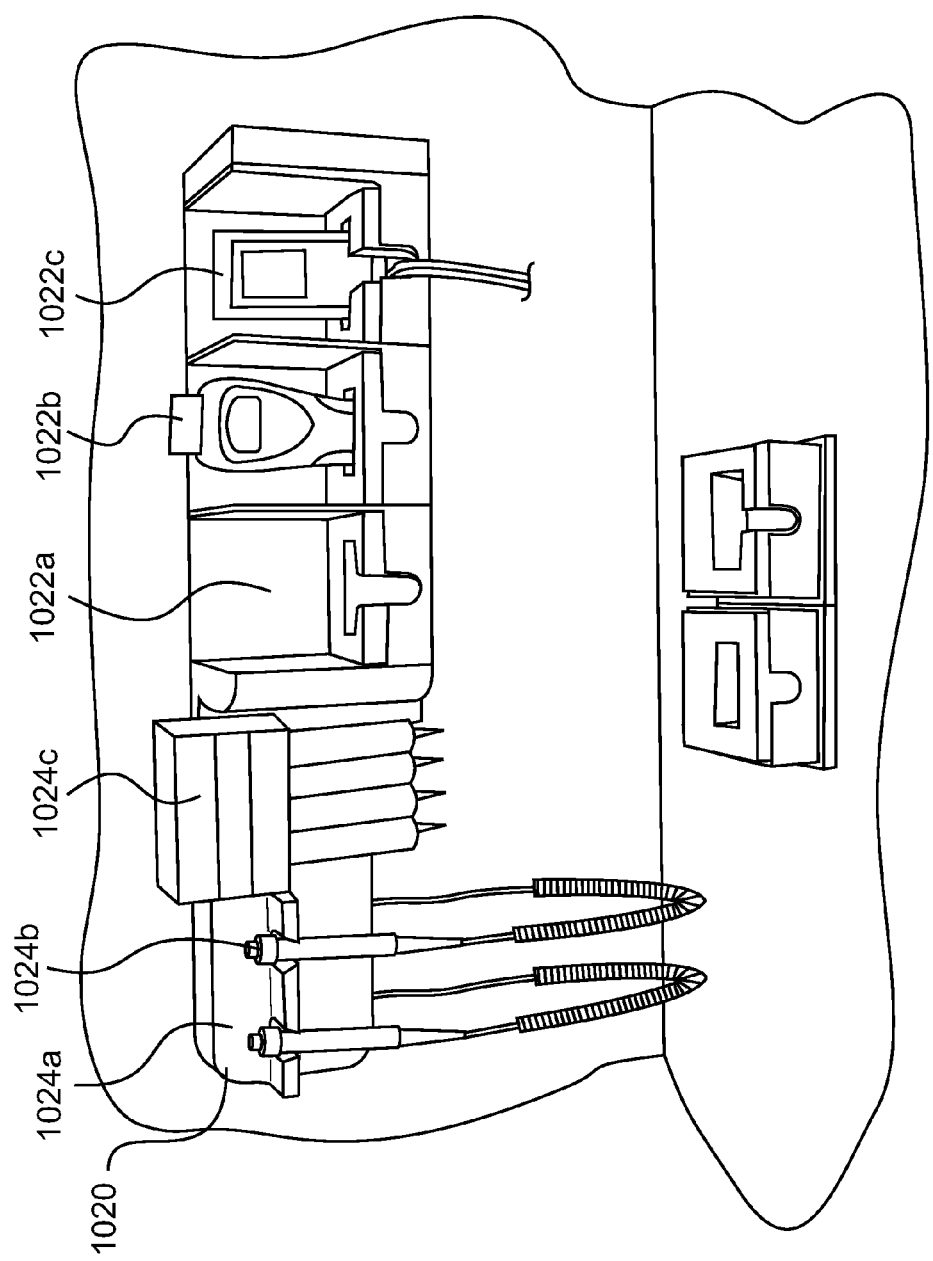

FIG. 10B illustrates a wall mounted 1010 configuration 1020 that provides mechanical, electrical and software interface support for hand held sensor devices each stored (docked) within a well 1022*a*-1022*b*. Each well 1012*a*-1012*b* is implemented as a module enclosure that has a mechanical and electrical interface with the cart 1010. Module enclosures 1024*a*-1024*c*, like those shown in FIGS. 5A-5D are also included in this wall mounted configuration 1020.

Figure 10C:
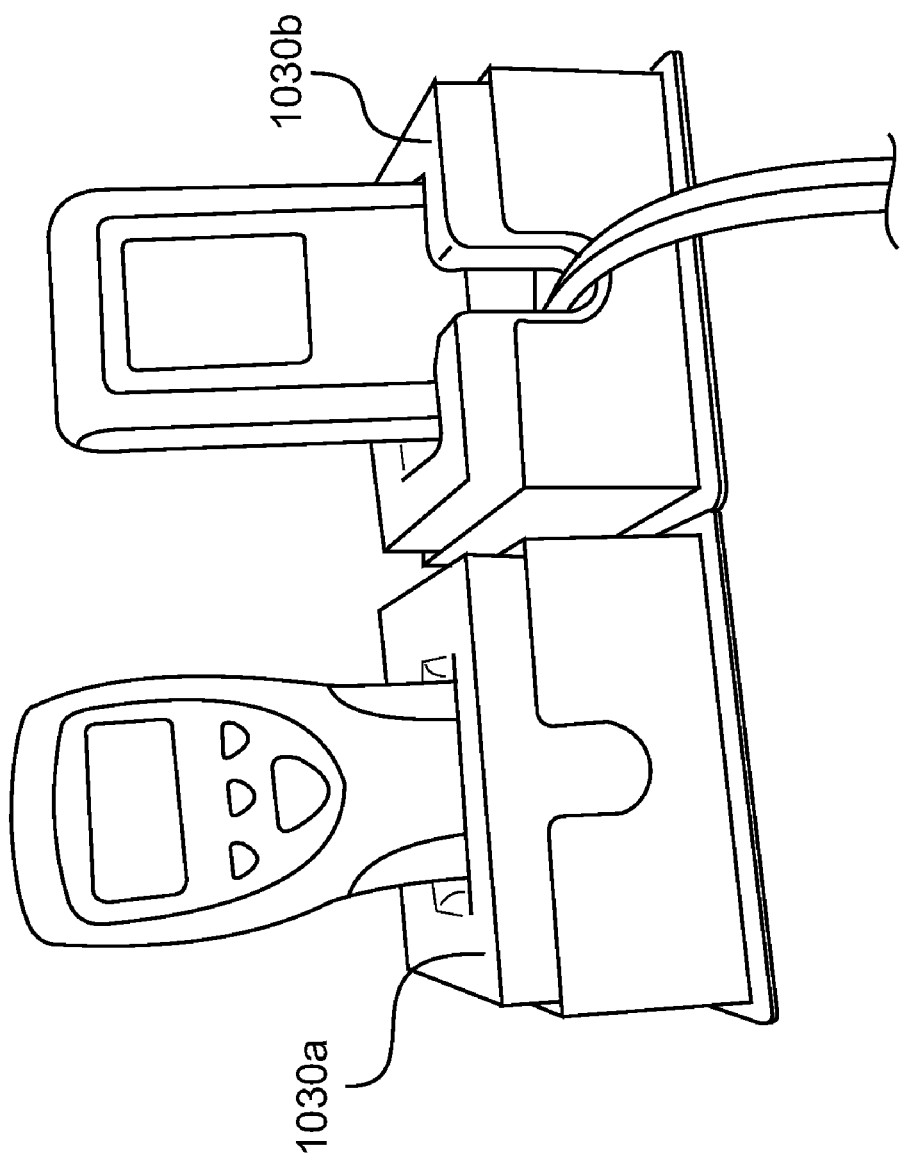

FIG. 10C illustrates a close up view of two (2) desktop mounted modules. As shown, the modules 1030*a* and 1030*b* are supported on top of a desktop surface without mechanical attachment to a supporting structure like that shown in FIGS. 2D-2E.

Figure 10D:
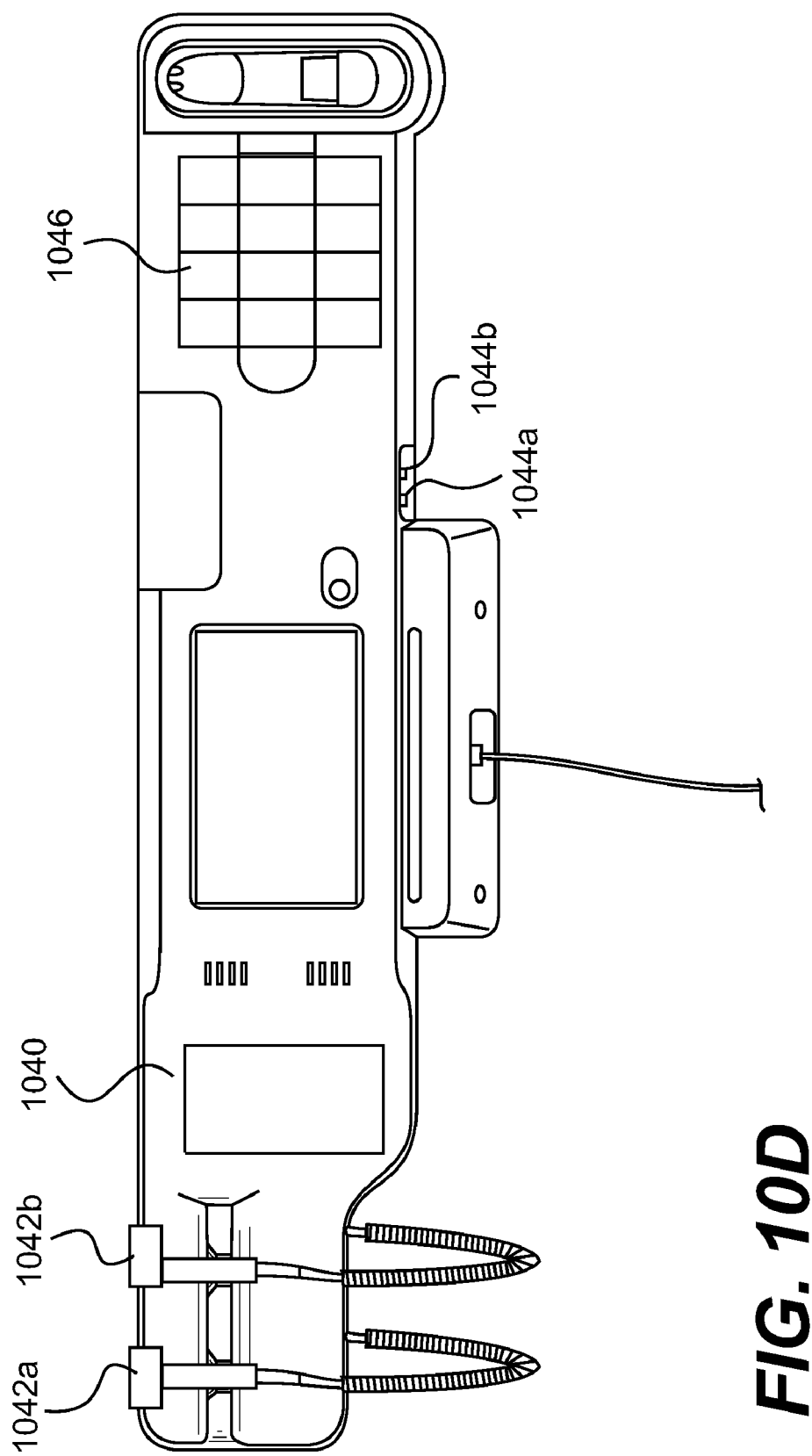

FIG. 10D illustrates an embodiment of a wall mounted configuration 1040 that provides a mechanical, electrical and software interface for a variety of hand held sensor devices. As shown, how each module enclosure is disposed within this configuration 1040 varies widely. Regardless, an electrical and software interface for each module is consistent throughout this configuration 1040.

For example, an ophthalmoscope 1042a and an otoscope 1042b are each accommodated, each without a respective well, on the left side of the wall mounted configuration 1040. An SPO2 module connection 1044a and a blood pressure (BP) measurement module connection 1044b are embedded into and accommodated on a lower side of the wall mounted configuration 1040. Also, four (4) forward facing modules slots 1046a-1046d are accommodated proximate to a right side of the configuration 1040. Additionally, an infrared (IR) thermometer is accommodated on a far right side of the wall mounted configuration 1040.

While the present invention has been explained with reference to the structure disclosed herein, it is not confined to the details set forth and this invention is intended to cover any modifications and changes as may come within the scope and spirit of the following claims.

What is claimed is:

1. A frame for integrating a plurality of health-care equipment modules, the frame comprising:
    a supporting structure providing a mechanical interface including at least one rail that is oriented substantially parallel to a supporting axis and configured for engagement with each of a plurality of modules at one time, each of the plurality of modules including an embedded component; and
    an electrical interface between a computing component and the embedded component,
    wherein the computing component is configured for providing a software interface enabling a software connection between the computing component and the embedded component, the software interface configured to establish interoperation between the computing component and the embedded component, and
    wherein at least one of electrical power and data is configured to be transferred between the computing component and the embedded component via at least one of the electrical interface and the software interface.

2. The frame of claim 1 wherein the data transfer mechanism includes a universal serial bus (USB), a universal serial bus (USB) host and a universal serial bus (USB) hub, and a universal serial bus (USB) module end-point connection.

3. The frame of claim 1 wherein the module is configured to input information from a sensory device.

4. The frame of claim 3 wherein the sensory device is configured for measurement of a physiological parameter.

5. The frame of claim 3 wherein the sensory device is a hand-held device.

6. The frame of claim 5 wherein the hand-held device is a medical diagnostic instrument.

7. The frame of claim 2, wherein the universal serial bus (USB) module end-point connection is for connection to the embedded component.

8. The frame of claim 7 wherein a universal serial bus (USB) cable provides the universal serial bus (USB) module end point connection, the universal serial bus (USB) cables having a first end electrically attached to the universal serial bus (USB) host via the universal serial bus (USB) hub and a second end electrically attached to the universal serial bus (USB) module end-point connection.

9. The frame of claim 2 wherein the universal serial bus (USB) module end-point connection supplies voltage within universal serial bus (USB) standards while supplying current substantially in excess of universal serial bus (USB) standards.

10. The frame of claim 2 wherein the computing component is electrically attached to a non-module universal serial bus (USB) hub connection accessible from an exterior of the frame and from an exterior of a module mechanically attached to the frame via the supporting structure.

11. The frame of claim 10 wherein the non-module universal serial bus (USB) hub connection supplies voltage and current within universal serial bus (USB) standards and wherein the universal serial bus (USB) module end-point connection supplies voltage within universal serial bus (USB) standards while simultaneously supplying current substantially in excess of universal serial bus (USB) standards.

12. The frame of claim 11 wherein the computing component transmits a command at least through one of a non-module universal serial bus (USB) host to an external component or the universal serial bus (USB) to the embedded component, to transition to a sleep mode.

13. The frame of claim 11 wherein the universal serial bus (USB) module end-point connection is designed to supply voltage between 4.75 volts and 5.25 volts and designed to supply current at a rate greater than or equal to 1.5 amperes.

14. The frame of claim 2 wherein the software interface executes a protocol communicating at least one of a vendor-identification value and product-identification value from the embedded component to the computing component via the universal serial bus (USB) module end point connection.

15. The frame of claim 2 wherein the computing component and the universal serial bus (USB) end-point module connection is isolated via a five-volt to five-volt isolation transformer.

16. The frame of claim 1 wherein the frame is further configured to be one of a desktop configuration, a wall configuration, a mobile configuration, a hand-carriable configuration, or a bed configuration.

17. The frame of claim 16 wherein each of the desktop configuration, the wall configuration, the mobile configuration, the hand-carriable configuration, and the bed configuration interoperate with equipment modules without modification to the mechanical interface, the electrical interface, or the software interface of the module.

18. The frame of claim 16 wherein the module is configured to be attached and detached from any one of the desktop configuration, the wall configuration, the mobile configuration, the hand-carriable configuration, and the bed configuration.

19. The frame of claim 1 further comprising an enclosure for the module, the enclosure having a discrete width corresponding to an integer number of multiple units of width, the discrete width corresponding to a width of the module.

20. The frame of claim 1 wherein the module is configured as a docking station for a hand-held device.

21. The frame of claim 20 wherein the module is a docking station for at least one of an otoscope, an ophthalmoscope, a rhinoscope, a laryngnoscope, an anoscope, a audiometer, a tympanometric instrument, a thermometer, and a vaginoscope.

22. The frame of claim 1 wherein the module is at least one of a blood pressure measuring module and a pulse oximetry measurement module.

23. The frame of claim 1 wherein the electrical interface is provided as a feature of a commercially available computer, whereby the computer can function as the computing component.

24. A frame for integrating a plurality of health-care equipment modules, the frame comprising:
- a supporting structure configured for a mechanical interface design including at least one rail that is oriented substantially parallel to a supporting axis and configured for engagement with each of a plurality of modules at one time, each of the plurality of modules having various widths, dimensioned to engage the supporting structure, and dimensioned to enclose an embedded component; and
- an electrical interface providing at least one of electrical power and data transfer between a computing component and each embedded component, and
- wherein the computing component is configured for providing a software interface for enabling a software connection between the computing component and each embedded component having an electrical interface providing data transfer.

25. The frame of claim 24 wherein the plurality of modules are adjacent to each other.

26. The frame of claim 24 wherein the software interface is configured to permit or deny interoperation between the computing component and each embedded component.

27. A frame for integrating a plurality of health-care equipment modules, the frame comprising:
- a supporting structure having a mechanical interface design including at least one rail that is oriented substantially parallel to a supporting axis and configured for engagement with each of a plurality of modules at one time,
- each of the plurality of modules comprising an embedded component for facilitating determination of a least one of a plurality of physiological parameters;
- each of the plurality of modules having a height dimension and a depth dimension that are each perpendicular to a supporting axis of said modules and substantially uniform in size between each of said modules, and where each of said modules has a width dimension parallel to said supporting axis and where said width dimension is not restricted to being substantially uniform and can vary substantially between each of said modules, so that one of said modules can comprise an embedded component of substantially different type or size relative to another embedded component comprised within another of said modules;
- an electrical interface providing at least one of electrical power and data transfer between a computing component and each embedded component, and
- wherein the computing component is configured for providing a software interface including execution of a communications protocol that is configured to establish interoperation between the computing component and the embedded component, and
- wherein at least one of electrical power and data is configured to be transferred between the computing component and the embedded component via at least one of the electrical interface and the software interface.

28. A frame of claim 27 where each of said modules has two substantially planar surfaces that are substantially parallel to each other and perpendicular to said supporting axis.

29. A frame for integrating a plurality of health-care equipment modules, the frame comprising:
- a supporting structure providing a mechanical interface including at least one rail that is oriented substantially parallel to a supporting axis and configured for engagement with each of a plurality of modules at one time, each of the plurality of modules including an embedded component; and
- an electrical interface between a computing component and the embedded component, and
- wherein the computing component is configured for providing a software interface configured to establish interoperation between the computing component and the embedded component, and
- wherein at least one of electrical power and data is configured to be transferred between the computing component and the embedded component via at least one of the electrical interface and the software interface, and
- wherein the software interface includes execution of a communications protocol that enables the embedded component to identify itself to the computing component by communicating at least one of a vendor-identification value and a product-identification value to the computing component.

30. The frame of claim 29 wherein the computing component performs a decision to permit or deny interoperation between the computing component and the embedded component and wherein the decision is based upon at least one of the vendor-identification value and the product-identification value.

31. The frame of claim 30 where the computing component is implemented as an embedded component within at least one of the plurality of modules.

* * * * *